(12) United States Patent
Papkoff et al.

(10) Patent No.: US 12,144,834 B2
(45) Date of Patent: Nov. 19, 2024

(54) METHODS AND COMPOSITIONS FOR TREATING GASTROINTESTINAL AND INFLAMMATORY DISORDERS

(71) Applicant: Xbiome Inc., New York, NY (US)

(72) Inventors: Jackie Papkoff, San Francisco, CA (US); Jun Ma, San Francisco, CA (US)

(73) Assignee: Xbiome Inc., New York, NY (US)

( * ) Notice: Subject to any disclaimer, the term of this patent is extended or adjusted under 35 U.S.C. 154(b) by 454 days.

(21) Appl. No.: 16/570,428

(22) Filed: Sep. 13, 2019

(65) Prior Publication Data

US 2020/0215129 A1 Jul. 9, 2020

Related U.S. Application Data

(60) Provisional application No. 62/782,666, filed on Dec. 20, 2018, provisional application No. 62/747,391, filed on Oct. 18, 2018, provisional application No. 62/734,495, filed on Sep. 21, 2018, provisional application No. 62/730,792, filed on Sep. 13, 2018.

(51) Int. Cl.
| | | |
|---|---|---|
| *A61K 35/742* | (2015.01) | |
| *A61K 35/00* | (2006.01) | |
| *A61K 35/741* | (2015.01) | |
| *A61K 47/26* | (2006.01) | |
| *A61P 1/04* | (2006.01) | |

(52) U.S. Cl.
CPC ............ *A61K 35/741* (2013.01); *A61K 47/26* (2013.01); *A61P 1/04* (2018.01); *A61K 2035/115* (2013.01)

(58) Field of Classification Search
None
See application file for complete search history.

(56) References Cited

U.S. PATENT DOCUMENTS

| | | | |
|---|---|---|---|
| 6,861,053 B1 | 3/2005 | Lin et al. | |
| 7,101,565 B2 | 9/2006 | Monte | |
| 7,115,200 B2 | 10/2006 | Ackermanns et al. | |
| 7,232,656 B2 | 6/2007 | Balasubramanian et al. | |
| 7,718,608 B2 | 5/2010 | Lin et al. | |
| 7,835,871 B2 | 11/2010 | Kain et al. | |
| 7,960,120 B2 | 6/2011 | Rigatti et al. | |
| 7,998,474 B2 | 8/2011 | Kelly | |
| 8,197,805 B2 | 6/2012 | Lin et al. | |
| 8,906,668 B2* | 12/2014 | Henn ................... | A61K 9/0053 435/252.4 |
| 9,066,962 B2 | 6/2015 | Pimentel et al. | |
| 9,314,489 B2 | 4/2016 | Kelly et al. | |
| 9,371,510 B2 | 6/2016 | Moore | |
| 9,415,079 B2 | 8/2016 | Honda et al. | |
| 9,421,230 B2 | 8/2016 | Honda et al. | |
| 9,433,652 B2 | 9/2016 | Honda et al. | |
| 9,494,587 B2 | 11/2016 | Goletz et al. | |
| 9,610,307 B2* | 4/2017 | Berry ................... | A61K 35/741 |
| 9,623,055 B2 | 4/2017 | Nieuwdorp et al. | |
| 9,642,882 B2 | 5/2017 | Honda et al. | |
| 9,827,276 B2 | 11/2017 | Honda et al. | |
| 9,907,755 B2 | 3/2018 | Kabadi et al. | |
| 9,937,211 B2 | 4/2018 | Kelly et al. | |
| 10,022,406 B2 | 7/2018 | Borody | |
| 10,028,980 B2 | 7/2018 | Sadowsky et al. | |
| 10,058,574 B2 | 8/2018 | Grant et al. | |
| 2005/0266069 A1* | 12/2005 | Simmons ............... | A23L 29/065 424/93.45 |
| 2005/0281775 A1* | 12/2005 | Carrington ............. | A61K 31/78 424/70.16 |
| 2006/0024681 A1 | 2/2006 | Smith et al. | |
| 2006/0292611 A1 | 12/2006 | Berka et al. | |
| 2007/0014362 A1 | 1/2007 | Cruz et al. | |
| 2009/0026082 A1 | 1/2009 | Rothberg et al. | |
| 2009/0127589 A1 | 5/2009 | Rothberg et al. | |
| 2010/0035252 A1 | 2/2010 | Rothberg et al. | |
| 2010/0137143 A1 | 6/2010 | Rothberg et al. | |
| 2010/0188073 A1 | 7/2010 | Rothberg et al. | |
| 2011/0009278 A1 | 1/2011 | Kain et al. | |
| 2011/0212079 A1* | 9/2011 | Mascarenhas ......... | A61P 29/00 514/17.7 |
| 2012/0178771 A1* | 7/2012 | Babul .................. | A61K 9/2054 514/282 |
| 2014/0335131 A1 | 11/2014 | Mazmanian et al. | |
| 2015/0037285 A1 | 2/2015 | Blaser et al. | |
| 2015/0037286 A1 | 2/2015 | Qin et al. | |
| 2015/0238545 A1 | 8/2015 | Borody | |
| 2016/0120915 A1 | 5/2016 | Blaser et al. | |

(Continued)

FOREIGN PATENT DOCUMENTS

| | | |
|---|---|---|
| WO | WO-2004085628 A1 | 10/2004 |
| WO | WO-2016033439 A2 | 3/2016 |

(Continued)

OTHER PUBLICATIONS

Assembly Biosciences, pp. 1-2, Jan. 27, 2016.*
Udayappan et al. NPJ Biofilms and Microbiomes, 2(1): 1-10, 2016.*
Bircher et al. Microb. Biotechnol. 11(4): 721-733, Epub Apr. 17, 2018.*
Arief et al., Benef Microbes. 6(4):603-13 (2015).
Baars et al., Microorganisms 3(4): 641-666 (2015).
Bisborough et al., Am J Gastroenterol Suppl 3:27-37 (2016).

(Continued)

*Primary Examiner* — S. Devi

(74) *Attorney, Agent, or Firm* — Barnes & Thornburg LLP; Aisha R. Hasan

(57) ABSTRACT

The disclosure relates generally to bacterial strains and bacterial strain mixtures, e.g., *Eubacterium, Bacteroides*, and *Roseburia* bacterial strains and mixtures thereof. The disclosure further relates to methods of using bacterial strains and bacterial strain mixtures for treating a gastrointestinal disorder, e.g., ulcerative colitis, an inflammatory disorder, and/or dysbiosis.

24 Claims, 19 Drawing Sheets

Specification includes a Sequence Listing.

(56) References Cited

U.S. PATENT DOCUMENTS

| | | |
|---|---|---|
| 2016/0199424 A1 | 7/2016 | Berry et al. |
| 2016/0243172 A1 | 8/2016 | Cook et al. |
| 2016/0271188 A1 | 9/2016 | Berry et al. |
| 2016/0271189 A1 | 9/2016 | Cutcliffe et al. |
| 2016/0310545 A1 | 10/2016 | Moore |
| 2016/0375065 A1 | 12/2016 | Mazmanian et al. |
| 2017/0020932 A1 | 1/2017 | Cutcliffe et al. |
| 2017/0027996 A1 | 2/2017 | Cutcliffe et al. |
| 2017/0100442 A1 | 4/2017 | Gamble et al. |
| 2017/0143774 A1 | 5/2017 | Mulder et al. |
| 2017/0151291 A1 | 6/2017 | Henn et al. |
| 2017/0224744 A1 | 8/2017 | Ning et al. |
| 2017/0246214 A1 | 8/2017 | Sadowsky et al. |
| 2017/0252378 A1 | 9/2017 | Sadowsky et al. |
| 2017/0252381 A1 | 9/2017 | Ning et al. |
| 2017/0296596 A1 | 10/2017 | Allen-Vercoe et al. |
| 2017/0319627 A1 | 11/2017 | Sadowsky et al. |
| 2017/0326184 A1 | 11/2017 | Patterson et al. |
| 2018/0015130 A1 | 1/2018 | Berry et al. |
| 2018/0071344 A1 | 3/2018 | Berry et al. |
| 2018/0087094 A1 | 3/2018 | Klumpp et al. |
| 2018/0092949 A1 | 4/2018 | Sokol et al. |
| 2018/0117097 A1 | 5/2018 | Chatila et al. |
| 2018/0117099 A1 | 5/2018 | Chatila et al. |
| 2018/0133265 A1 | 5/2018 | Stevenson |
| 2018/0140648 A1 | 5/2018 | Segal et al. |
| 2018/0146681 A1 | 5/2018 | Clube |
| 2018/0185421 A1 | 7/2018 | Kakihana et al. |
| 2018/0193391 A1 | 7/2018 | Sefik et al. |
| 2018/0243350 A1 | 8/2018 | Raa et al. |
| 2018/0250350 A1 | 9/2018 | Sokol et al. |
| 2018/0256652 A1 | 9/2018 | Borody |
| 2018/0274036 A1 | 9/2018 | Van Den Brink et al. |
| 2018/0353554 A1 | 12/2018 | Henn et al. |
| 2019/0247367 A1* | 8/2019 | Goldfeld ............... A61P 31/18 |
| 2020/0376044 A1* | 12/2020 | Han .................. A61K 35/741 |

FOREIGN PATENT DOCUMENTS

| | | |
|---|---|---|
| WO | WO-2017053544 A1 | 3/2017 |
| WO | WO-2017102816 A1 | 6/2017 |
| WO | WO-2017146580 A1 | 8/2017 |
| WO | WO-2017172894 A2 | 10/2017 |
| WO | WO-2017205302 A1 | 11/2017 |
| WO | WO-2017218889 A1 | 12/2017 |
| WO | WO-2018057914 A1 | 3/2018 |
| WO | WO-2018064165 A2 | 4/2018 |
| WO | WO-2018065132 A1 | 4/2018 |
| WO | WO-2018075886 A1 | 4/2018 |
| WO | WO-2018094190 A2 | 5/2018 |
| WO | WO-2018106844 A1 | 6/2018 |
| WO | WO-2018136884 A1 | 7/2018 |
| WO | WO-2018140931 A1 | 8/2018 |
| WO | WO-2018152306 A1 | 8/2018 |
| WO | WO-2019028402 A1 | 2/2019 |
| WO | WO-2019157566 A1 | 8/2019 |

OTHER PUBLICATIONS

Charrier et al., Microbiology, 152: 179-185 (2006).
Chassaing et al., Curr Protoc Immunol.;104:Unit 15.25 (2014).
Comstock et al., BioEssays, 25: 926-929 (2003).
Dolan et al., PLoS One. 7(10): e47300 (2012).
Doria et al., N Engl J Med 368(19):1845 (2013).
Duncan et al., Applied and Environmental Microbiology, 69(2): 1136-1142 (2003).
Duncan et al., Applied and Environmental Microbiology, 70(10): 5810-5817 (2004).
Duncan et al., Int. J. Syst. Evol. Microbiol., 56: 2437-2441 (2006).
Ellington et al., Clin Microbiol Infect. 23(1):2-22 (2017).
Engels et al., Front Microbiol. 7(713): 1-12 (2016).
Fiorucci et al., Br. J. Pharmacol. 150:996-1002 (2007).
Genin et al., BMC Cancer 15:577 (2015).
Hall et al., Journal of Pediatric Surgery 48:353-358 (2013).
Hiippala et al., Nutrients, 10(988): 1-23 (2018).
Hoeppli et al., Front Immunol 6:61 (2015).
Husain et al., Microb Genom. 3(11) (2017).
International Search Report for PCT/US2019/051064, mailed Jan. 22, 2020 (5 pages).
Kassinen et al., Gastroenterology, 133(1): 24-33 (2007).
Koh et al., Cell 165(6):1332-1345 (2016).
Kole et al., Curr Top Microbiol Immunol. 380:19-38 (2014).
Krause et al., Nature Communications 6: 7055 (2015).
Lee and Hase, Nat Chem Biol 10(6):416-424 (2014).
Li and He, World J Gastroenterol. 10(5):620-5 (2004).
Louis et al., FEMS Microbiology Letters, 294: 1-8 (2008).
Michielan et al., Mediators Inflamm. 2015:628157 (2015).
Nielsen et al., Gut, 38:414-420 (1996).
Nys et al., Nat Rev Gastroenterol Hepatol. (7):395-401 (2013).
Ostvik et al., Clin Exp Immunol. 173:502-511 (2013).
Patterson et al., Frontiers in Immunology, 8(1166): 1-14 (2017).
Pontier et al., J. Pharm. Sci., 90(10): 1608-19 (2001).
Poxton et al., J. Med. Microbiol., 46: 85-91 (1997).
Pryde et al., FEMS Microbiology Letters, 217: 133-139 (2002).
Puleston et al., Cold Spring Harb Protoc; doi:10.1101/pdb.top070391.
Pumbwe et al., Microb Pathog. 43(2-3):78-87 (2007).
Reeves et al., J. Bacteriol., 179(3): 643-649 (1997).
Renye Jr. et al., Biotechnol Lett. (11):1947-1954 (2016).
Rutgeerts et al., N Engl J Med. 353(23):2462-76 (2005).
Seo et al., Sci. Rep 7(1):851 (2017).
Seth and Taga, Front Microbiol. 5:350 (2014).
Shetty et al., Genome Announc., 5(43): e01167-17 (2017).
Shetty et al., Int J Syst Evol Microbiol. 68:3741-3746 (2018).
Siguier et al., FEMS Microbiology Reviews, 38(5): 865-891 (2013).
Sim et al., J. Vis. Exp. (112), e54128 (2016).
Spinler et al., Anaerobe. 14(3):166-71 (2008).
Stallhofer et al., Inflamm Bowel Dis 21(10):2327-2340 (2015).
Steinbach et al., Inflamm Bowel Dis. 20(1):166-175 (2014).
Sudhakaran et al., Genes Nutr., 8(6): 637-48 (2013).
Tilg et al., Gut, 0: 1-2 (2013).
Travis et al., Genome Announc., 3(6): 01286-15 (2015).
Ungaro et al., Lancet 389(10080):1756-1770 (2017).
Wilson et al., PLoS Pathog. (8): e1002171 (2011).
Written Opinion for PCT/US2019/051064, mailed Jan. 22, 2020 (9 pages).
Wu et al., PLoS ONE 7:e37572 (2012).
Wu et al., Science, 350(6256): 1-21 (2015).
Xu et al., Science, 299(5616): 2074-2076 (2003).
Yin et al., Front Immunol. 2018; 9: 1512 (2018).

* cited by examiner

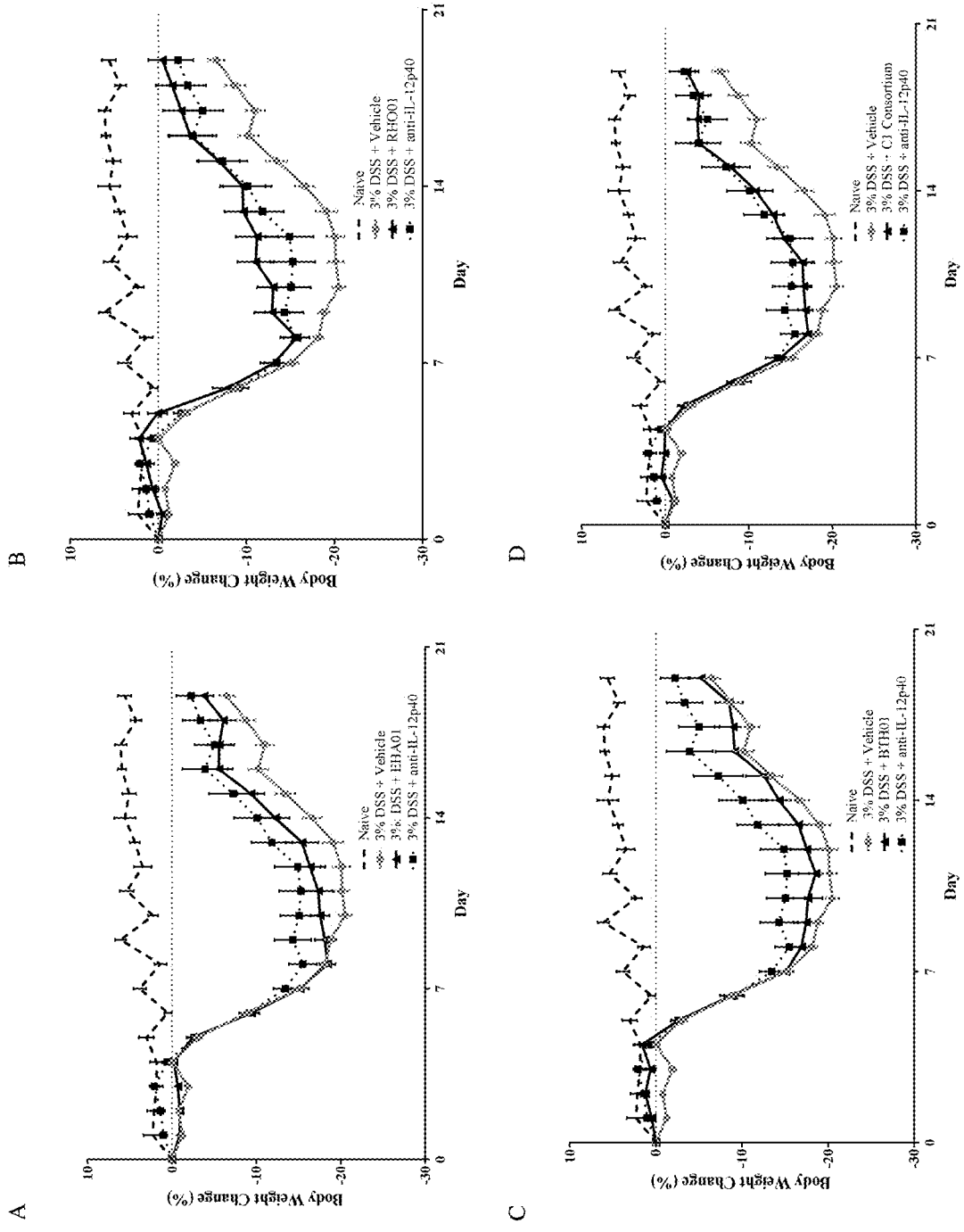
FIG. 13A-D

FIG. 13E-F
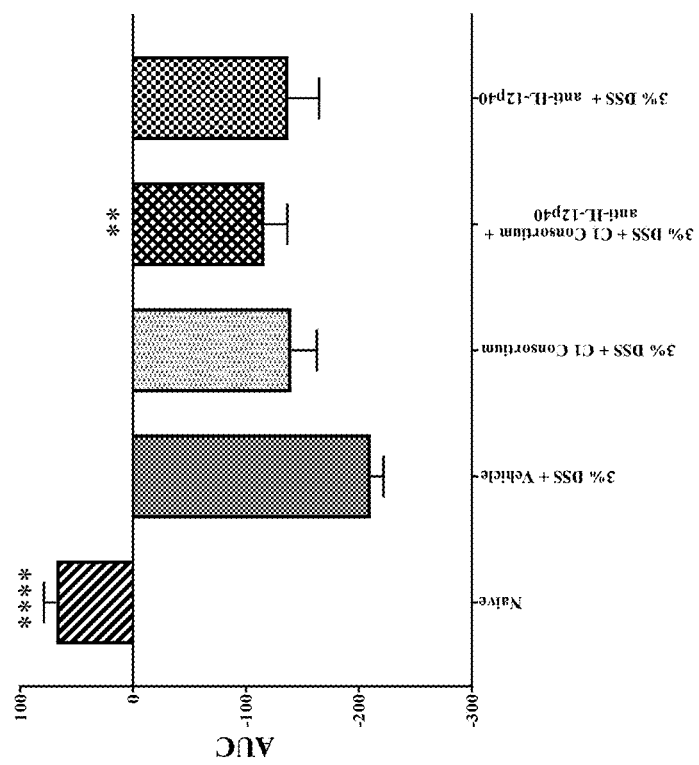
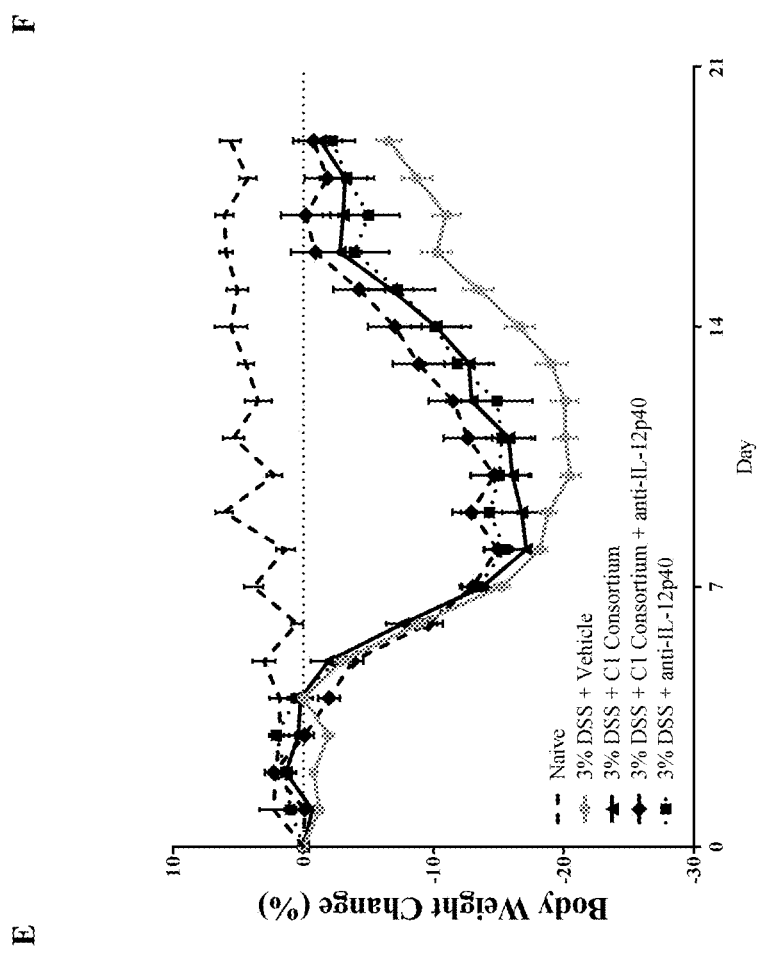

Figure 14
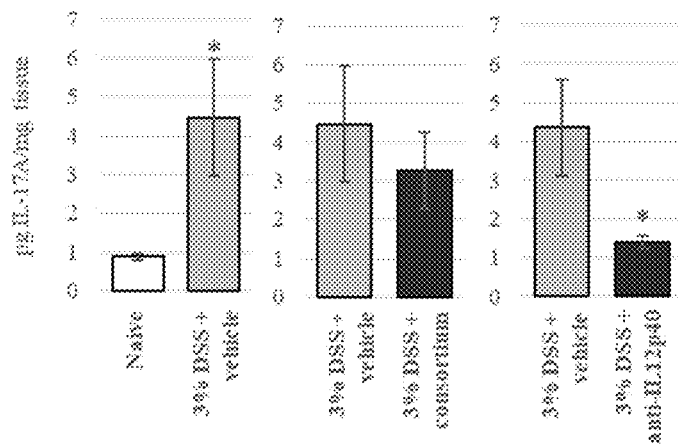
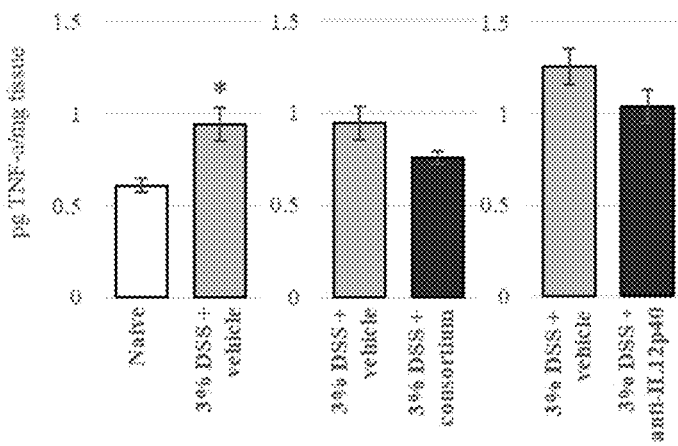
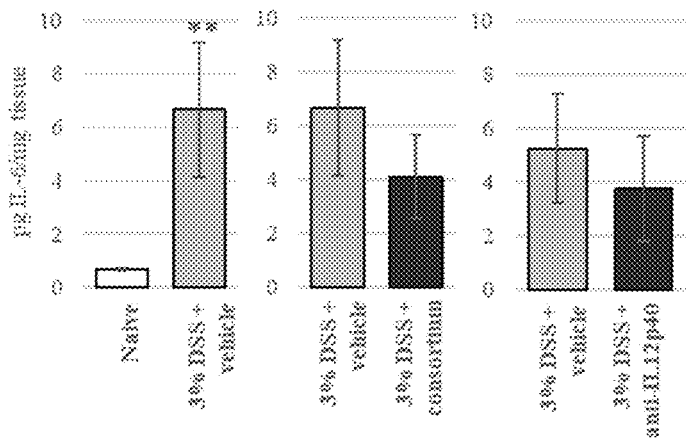

Figure 15
A
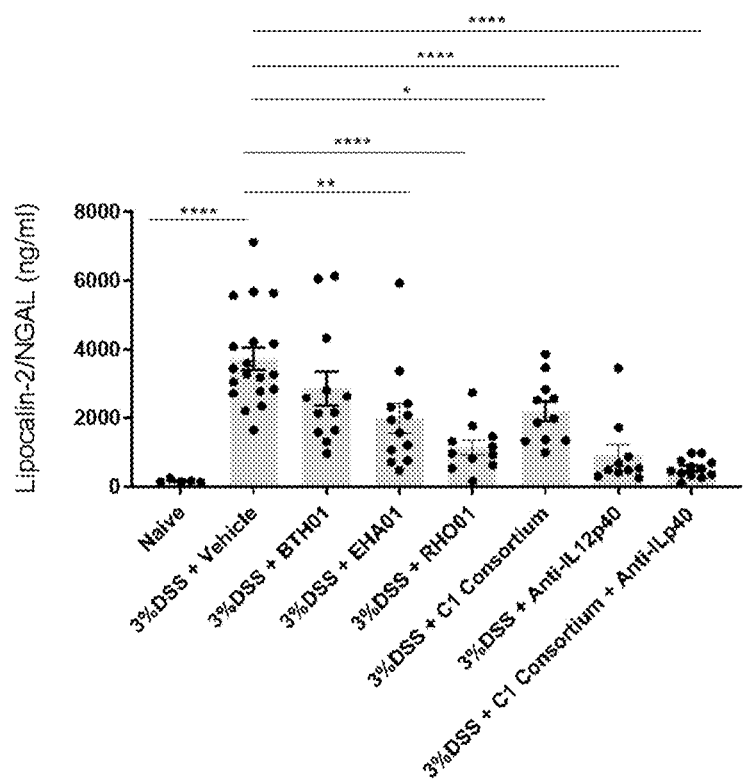
B
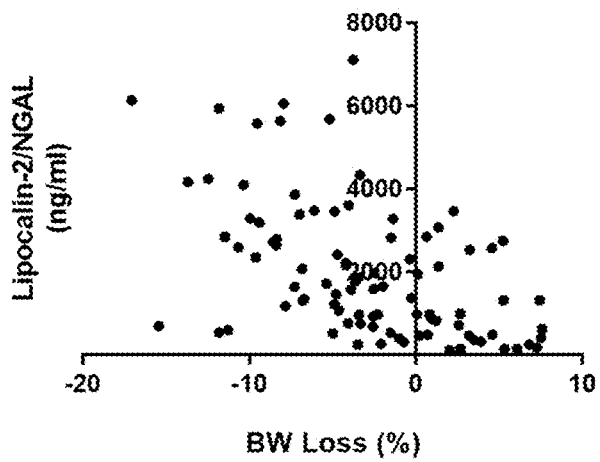

METHODS AND COMPOSITIONS FOR TREATING GASTROINTESTINAL AND INFLAMMATORY DISORDERS

CROSS REFERENCE TO RELATED APPLICATIONS

This application claims the benefit of, and priority to, U.S. provisional patent application Ser. No. 62/730,792, filed Sep. 13, 2018, U.S. provisional patent application Ser. No. 62/734,495, filed Sep. 21, 2018, U.S. provisional patent application Ser. No. 62/747,391, filed Oct. 18, 2018, and U.S. provisional patent application Ser. No. 62/782,666 filed Dec. 20, 2018, each of which are hereby incorporated by reference herein in their entirety.

SEQUENCE LISTING

The instant application contains a Sequence Listing which has been filed electronically in ASCII format and is hereby incorporated by reference in its entirety. Said ASCII copy, created on Dec. 19, 2018, is named ASP-056_SL.txt and is 17,078,089 bytes in size.

BACKGROUND

The gastrointestinal tract (GI), as well as other organ systems, is a complex biological system that includes a community of many different organisms, including diverse strains of bacteria. Hundreds of different species may form a commensal community in the gastrointestinal tract and other organs in a healthy person. Moreover, microorganisms present in the gut not only play a crucial role in digestive health, but also influence the immune system.

A disturbance or imbalance in a biological system, e.g., the gastrointestinal tract, may include changes in the types and numbers of bacteria in the gut which may lead to the development of, or may be an indicator of, a disease state. Patients who suffer from certain diseases (e.g., gastrointestinal diseases) may have a microbiota spectrum that is different to that of healthy people. For example, ulcerative colitis (UC) is associated with an altered and imbalanced colonic microbial community structure (dysbiosis) with reduced bacterial species diversity and stability over time. In settings of such dysbiosis, microbiota functions can change, resulting in increased susceptibility to pathogens, altered metabolic profiles, or induction of proinflammatory signals that can result in local or systemic inflammation or autoimmunity.

Ulcerative colitis (UC), a form of inflammatory bowel disease (IBD), is an idiopathic, chronic, inflammatory disease that affects the colon. It is characterized by relapsing and remitting mucosal inflammation that starts in the rectum and reaches various extents of the proximal colon. Drugs that are used to treat UC include mesalamine, corticosteroids, oral immunosuppressive drugs, and monoclonal antibodies directed against TNF-α and α$\beta$7 lymphocyte integrin. Aminosalicylates (mesalamine, 5-ASA) are the standard-of-care in the treatment of mildly-to-moderately active UC. However, a significant number of mildly-to-moderately active patients with UC do not adequately respond to first-line treatment with mesalamine alone, necessitating the introduction of more toxic immunosuppressive medications. For example, systemic immune-suppressants, including biological drugs, are often used to treat patients suffering from moderate-to-severe UC who fail to adequately respond to mesalamine (5-ASA) therapy alone. Colectomy is needed in up to 15% of patients with UC (Ungaro et al., Lancet 389 (10080): 1756-1770 (2017)).

The inability of a significant number of patients suffering from gastrointestinal disorders to adequately respond to first-line treatment underscores the need in the art for pharmaceutical compositions and methods that can effectively treat this patient segment.

BRIEF SUMMARY

The disclosure relates generally to bacterial strains and bacterial strain mixtures, e.g., *Eubacterium, Bacteroides*, and *Roseburia* bacterial strains and mixtures thereof. Disclosed bacterial strains or bacterial strain mixtures are useful for treating gastrointestinal disorders and/or inflammatory disorders, including, for example, dysbiosis and/or immune mediated inflammatory disorders, such as ulcerative colitis, Crohn's disease, and other forms of inflammatory bowel disease (IBD).

For example, in one aspect, provided herein is a pharmaceutical composition comprising: a bacterial mixture comprising at least 2 bacterial species, each selected from the group consisting of: a *Bacteroides* species, a *Eubacterium* species, and a *Roseburia* species; and a pharmaceutically acceptable excipient. In certain embodiments, a contemplated bacterial mixture comprises a *Bacteroides* species, a *Eubacterium* species, and a *Roseburia* species. In certain embodiments, a contemplated bacterial mixture consists essentially of a *Bacteroides* species, a *Eubacterium* species, and a *Roseburia* species. In certain embodiments, the *Bacteroides* species of the bacterial mixture is *Bacteroides* thetaiotaomicron. In certain embodiments, the *Eubacterium* species of the bacterial mixture is *Eubacterium hallii*. In certain embodiments, the *Roseburia* species of the bacterial mixture is *Roseburia hominis*. In certain embodiments, a contemplated bacterial mixture is in lyophilized powder form. In certain embodiments, a disclosed bacterial mixture is capable of increasing production of at least one anti-inflammatory gene product, e.g., IL-10 and/or CCL-18 in a human cell, e.g., a THP-1 macrophage or a PBMC. In certain embodiments, a disclosed bacterial mixture is capable of reducing or attenuating production of at least one pro-inflammatory gene product, e.g., IL-6, IL-12, IL-17 and/or TNF-α in a human cell, e.g., a THP-1 macrophage or a PBMC. In certain embodiments, a disclosed bacterial mixture is capable of reducing or preventing disruption of, or increasing, barrier integrity of a human cell (e.g., an epithelial cell) monolayer, e.g., a HT29MTX-E12 cell monolayer treated with TNF-α. In certain embodiments, a disclosed bacterial mixture is capable of inducing or increasing autophagy in a human cell, e.g., a THP-1 macrophage. In certain embodiments, a disclosed bacterial mixture is capable of reducing or attenuating production of Lipocalin-2/NGAL in a cell, tissue or subject.

In another aspect, provided herein is a method of treating a gastrointestinal disorder in a subject in need thereof. A contemplated method comprises administering to the subject an effective amount of a disclosed pharmaceutical composition, pharmaceutical unit, or bacterial strain.

In some embodiments, the method comprises administering to the subject at least 2 bacterial strains, each selected from the group consisting of: a *Bacteroides* species strain, a *Eubacterium* species strain, and a *Roseburia* species strain. In certain embodiments, each bacterial strain is in lyophilized powder form.

Contemplated gastrointestinal disorders include, for example, dysbiosis and/or immune mediated inflammatory disorders, such as ulcerative colitis, Crohn's disease, and other forms of inflammatory bowel disease (IBD).

In another aspect, provided herein is a method of treating ulcerative colitis (UC) in a subject in need thereof. A contemplated method comprises administering to the subject an effective amount of a disclosed pharmaceutical composition, pharmaceutical unit, or bacterial strain. A contemplated subject may have had an inadequate response to an administration of a previous treatment for UC, e.g., mesalamine. For example, a contemplated subject may have previously been administered ≥2.4 g/day mesalamine orally for at least 8 weeks.

In another aspect, provided herein is a method of treating a dysbiosis in a subject in need thereof. A contemplated method comprises administering to the subject an effective amount of a disclosed pharmaceutical composition, pharmaceutical unit, or bacterial strain. In certain embodiments, the subject also has a gastrointestinal disorder.

In another aspect, provided herein is a method of modifying the gut microbiome of a subject in need thereof. A contemplated method comprises administering to the subject an effective amount of a disclosed pharmaceutical composition, pharmaceutical unit, or bacterial strain. In certain embodiments, the subject also has a gastrointestinal disorder.

In another aspect, provided herein is a method of treating an inflammatory disorder in a subject in need thereof. A contemplated method comprises administering to the subject an effective amount of a disclosed pharmaceutical composition, pharmaceutical unit, or one or more bacterial strains.

Contemplated methods may further comprise, e.g., administering a corticosteroid to a subject, pretreating a subject with an antibiotic, administering an antibiotic to a subject, or administering a prebiotic to a subject.

These and other aspects and features of the disclosure are described in the following detailed description and claims.

DESCRIPTION OF THE DRAWINGS

The disclosure can be more completely understood with reference to the following drawings.

FIG. 1A depicts the profile of strain BTH01. FIG. 1B depicts the profile of strain EHA01. FIG. 1C depicts the profile of strain RHO01. FIG. 1D depicts the profile of the consortium of strains BTH01+EHA01+RHO01. Levels of lactate, acetate, propionate and butyrate in batch culture supernatants of individual C1 strains as well a consortium of all three strains were analyzed by HPLC (ABPDU Berkeley CA). The average amounts of the SCFAs detected from two independent experiments are shown for individual strains BTH01 (A), EHA01 (B) and RHO01 (C) as well as a consortium of all three strains (D).

FIG. 2A depicts the profile of strains BTH01, EHA01 and RHO01 individually. FIG. 2B depicts the profile of the consortium of strains BTH01+EHA01+RHO01. At the indicated timepoints, samples were taken followed by transfer of portions of cultures to fresh medium for fed-batch culturing. Abundance represented as copy number/ml of sample for each strain was determined by species-specific qPCR for strains grown individually (2A) and in consortium (2B).

FIGS. 13A-13F depicts the effect of C1 bacterial consortium and individual strains on percent body weight change in a DSS-induced colitis mouse model. Groups of mice for naïve (N=5), individual test articles (N=12), consortium (N=24), consortium plus anti-IL-12p40 antibody (N=12) and vehicle control (N=20) were used in a standard DSS-induced colitis model. Mice were treated with 3% DSS in drinking water from days 0-5. Groups of mice were treated from days-1-19 daily with an oral dose of 3×10$^9$ VCC of each individual C1 bacterial strain, the C1 consortium containing each strain at 1×10$^9$ VCC or the C1 consortium containing each strain at 1×10$^9$ VCC plus anti-IL-12p40 antibody (at 10 mg/kg in PBS, dosed Q3D starting on Day 6 by IP). Groups of mice were administered PBS as a vehicle negative control or an antibody against IL-12p40 (Q3D IP) alone as a positive control for efficacy. A plot of daily body weight change over time (d0-19) for each test group is shown alongside naïve mice (dashed black), vehicle control (grey, circle) and anti-IL-12p40 (dotted black, square). (13A) EHA01, (13B) RHO01, (13C) BTH01, (13D) C1, and (13E) C1+anti-IL-12p40. (13F) AUC analysis of C1+anti-IL-12p40. Error bars are shown as SEM.

FIGS. 14A-14C depicts cytokine levels in colon tissue on day 19 of DSS-induced colitis. Cytokine levels were evaluated by ELISA after colon tissue homogenization in lysis buffer. Levels were normalized to mg of tissue analyzed. *p value≤0.05; **p value≤0.001; Mann-Whitney non-parametric test.

FIGS. 15A-15B depicts Lipocalin-2/NGAL levels in plasma on day 19 of DSS-induced colitis. Lipocalin-2/NGAL was evaluated by ELISA and levels were normalized to ml of plasma analyzed. Differences between groups of experiments were statistically determined by using one-factor ANOVA with a Tukey post hoc test. (A) Lipocalin-2/NGAL plasma levels; (B) Lipocalin-2/NGAL plasma levels versus body weight (BW) loss (%). (r=−0.5129; 95% confidence interval=−0.6502 to −0.3432; R2=0.2631; P value: P (two-tailed)=<0.0001; significant (alpha=0.05)).

DETAILED DESCRIPTION

Figure 1:
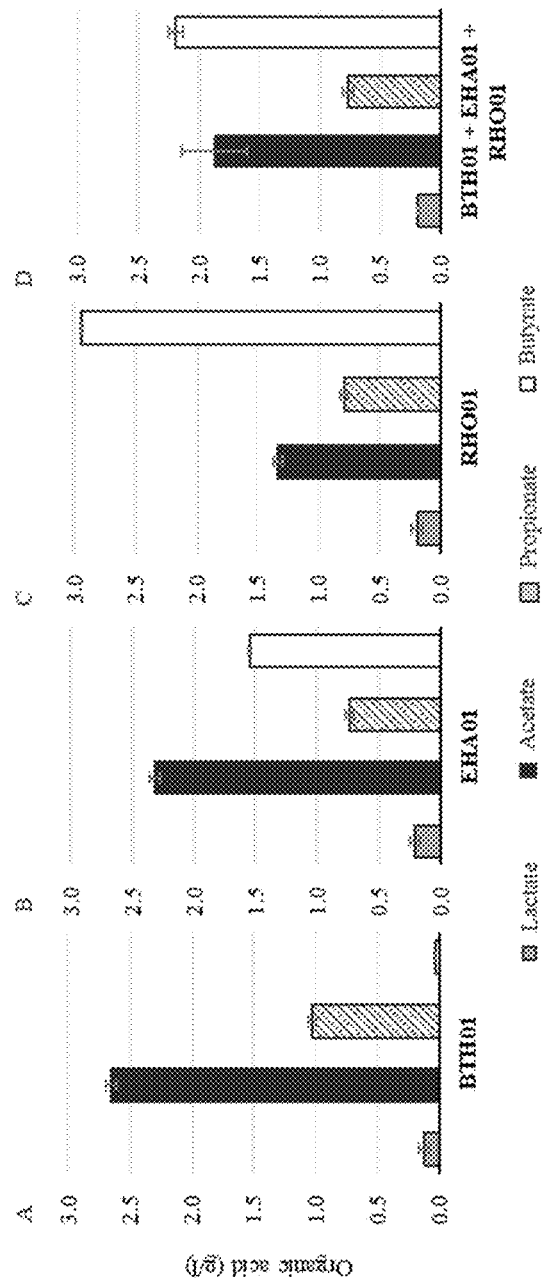
FIGS. 1A-1D depict the short-chain fatty acid (SCFA) production profile of Consortium 1 (C1) bacterial strains in individual as well as consortium batch cultures.

The disclosure relates generally to bacterial strains and bacterial strain mixtures, e.g., *Eubacterium*, *Bacteroides*, and *Roseburia* bacterial strains and mixtures thereof. For example, in one aspect, provided herein is a pharmaceutical composition comprising: a bacterial mixture comprising at least 2 bacterial species, each selected from the group consisting of: a *Bacteroides* species, a *Eubacterium* species, and a *Roseburia* species; and a pharmaceutically acceptable excipient. In certain embodiments, a contemplated bacterial mixture comprises a *Bacteroides* species, a *Eubacterium* species, and a *Roseburia* species. In certain embodiments, a contemplated bacterial mixture consists essentially of a *Bacteroides* species, a *Eubacterium* species, and a *Roseburia* species. In certain embodiments, the *Bacteroides* species of the bacterial mixture is *Bacteroides thetaiotaomicron*. In certain embodiments, the *Eubacterium* species of the bacterial mixture is *Eubacterium hallii*. In certain embodiments, the *Roseburia* species of the bacterial mixture is *Roseburia hominis*.

In another aspect, provided herein is a pharmaceutical composition comprising: a bacterial mixture comprising at least 2 bacteria species each selected from the group consisting of: a *Bacteroides* species, a *Eubacterium* species, and a *Roseburia* species, wherein the bacterial mixture is capable of: (i) increasing production of at least one anti-inflammatory gene product, e.g., IL-10 and/or CCL-18 in a human cell, e.g., a THP-1 monocyte or macrophage or a peripheral blood mononuclear cell (PBMC); (ii) reducing or attenuating production of at least one pro-inflammatory gene product, e.g., IL-6, IL-12, IL-17 and/or TNF-α in a human cell, e.g., a THP-1 macrophage or a PBMC; (iii) reducing or preventing disruption of, or increasing, barrier integrity of a human cell (e.g., an epithelial cell) monolayer, e.g., a HT29MTX-E12 cell monolayer treated with TNF-α, for example, as measured by trans epithelial electrical resistance (TEER); (iv) inducing or increasing autophagy in a human cell, e.g. a THP-1 monocyte or macrophage; and/or (v) reducing or attenuating production of Lipocalin-2/NGAL in a cell, tissue or subject; and a pharmaceutically acceptable excipient. In another aspect, provided herein is a pharmaceutical unit comprising: a bacterial strain mixture comprising at least 2 bacteria species each selected from the group consisting of a *Bacteroides* species strain, a *Eubacterium* species strain, and a *Roseburia* species strain, and wherein the pharmaceutical unit has, e.g., at least $1 \times 10^6$, at least $1 \times 10^7$, at least $1 \times 10^8$, at least $1 \times 10^9$, at least $1 \times 10^{10}$, at least $1 \times 10^{11}$, or at least $1 \times 10^{12}$ viable organisms (e.g., cfus) of bacteria; and a pharmaceutically acceptable excipient. In certain embodiments, a contemplated bacterial strain mixture comprises at least about $1 \times 10^9$ viable organisms (e.g., cfus) of a *Bacteroides* species strain, at least about $1 \times 10^9$ viable organisms (e.g., cfus) of a *Eubacterium* species strain, and/or at least about $1 \times 10^9$ viable organisms (e.g., cfus) of a *Roseburia* species strain, or any combination thereof.

The disclosure further provides a pharmaceutical composition comprising a *Eubacterium* species strain and a pharmaceutically acceptable excipient. In certain embodiments, a contemplated composition further comprises a *Bacteroides* species strain and/or a *Roseburia* species strain. In some embodiments, the *Eubacterium* species strain is a strain of *Eubacterium hallii*.

The disclosure further provides a pharmaceutical composition comprising a *Bacteroides* species strain and a pharmaceutically acceptable excipient. In certain embodiments, a contemplated composition further comprises a *Eubacterium* species strain and/or a *Roseburia* species strain. In some embodiments, the *Bacteroides* species strain is a strain of *Bacteroides thetaiotaomicron*.

The disclosure further provides a pharmaceutical composition comprising a *Roseburia* species strain and a pharmaceutically acceptable excipient. In certain embodiments, a contemplated composition further comprises a *Bacteroides* species strain and/or a *Eubacterium* species strain. In some embodiments, the *Roseburia* species strain is a strain of *Roseburia hominis*.

In another aspect, provided herein is a bacterial strain of *Roseburia hominis* capable of: (i) increasing production of at least one anti-inflammatory gene product, e.g., IL-10 and/or CCL-18, in a human cell, e.g., a THP-1 macrophage or monocyte or a PBMC; (ii) reducing or attenuating production of at least one pro-inflammatory gene product, e.g., IL-6, IL-12, IL-17 and/or TNF-α, in a human cell, e.g., a THP-1 macrophage or monocyte or a PBMC; (iii) reducing or preventing disruption of, or increasing, barrier integrity of a human cell (e.g., an epithelial cell) monolayer, e.g., a HT29MTX-E12 cell monolayer treated with TNF-α; (iv) inducing or increasing autophagy in a human cell, e.g., a THP-1 macrophage; and/or (v) reducing or attenuating production of Lipocalin-2/NGAL in a cell, tissue or subject. In another aspect, provided herein is a bacterial strain of *Bacteroides thetaiotaomicron* capable of: (i) increasing production of at least one anti-inflammatory gene product, e.g., IL-10 and/or CCL-18, in a human cell, e.g., a THP-1 macrophage or monocyte or a PBMC; (ii) reducing or attenuating production of at least one pro-inflammatory gene product, e.g., IL-6, IL-12, IL-17 and/or TNF-α, in a human cell, e.g., a THP-1 macrophage or monocyte or a PBMC; (iii) reducing or preventing disruption of, or increasing, barrier integrity of a human cell (e.g., an epithelial cell) monolayer, e.g., a HT29MTX-E12 cell monolayer treated with TNF-α; (iv) inducing or increasing autophagy in a human cell, e.g., a THP-1 macrophage; and/or (v) reducing or attenuating production of Lipocalin-2/NGAL in a cell, tissue or subject. In another aspect, provided herein is a bacterial strain of *Eubacterium hallii* capable of: (i) increasing production of at least one anti-inflammatory gene product, e.g., IL-10 and/or CCL-18, in a human cell, e.g., a THP-1 macrophage or monocyte or a PBMC; (ii) reducing or attenuating production of at least one pro-inflammatory gene product, e.g., IL-6, IL-12, IL-17 and/or TNF-α, in a human cell, e.g., a THP-1 macrophage or monocyte or a PBMC; (iii) reducing or preventing disruption of, or increasing, barrier integrity of a human cell (e.g., an epithelial cell) monolayer, e.g., a HT29MTX-E12 cell monolayer treated with TNF-α; (iv) inducing or increasing autophagy in a human cell, e.g., a THP-1 macrophage; and/or (v) reducing or attenuating production of Lipocalin-2/NGAL in a cell, tissue or subject.

The disclosure further relates to pharmaceutical compositions or units and methods of using disclosed bacterial strains and/or bacterial strain mixtures to treat gastrointestinal disorders and inflammatory disorders, including, for example, dysbiosis and/or immune mediated inflammatory disorders, such as ulcerative colitis, Crohn's disease, and other forms of inflammatory bowel disease (IBD).

I. Bacterial Strains and Bacterial Strain Mixtures

As used herein, the term "species" refers to a taxonomic entity as conventionally defined by genomic sequence and phenotypic characteristics. A "strain" is a particular instance of a species that has been isolated and purified according to conventional microbiological techniques. Contemplated bacterial species and/or strains include those that are live and/or viable, as well as those that are killed, inactivated or attenuated. Additionally, contemplated bacterial strains include vegetative forms and non-spore-forming forms of bacteria.

The present disclosure encompasses derivatives of the disclosed bacterial strains. The term "derivative" includes daughter strains (progeny) or stains cultured (sub-cloned)

from the original but modified in some way (including at the genetic level), without altering negatively a biological activity of the strain.

rRNA, 16S rDNA, 16S rRNA, 16S, 18S, 18S rRNA, and 18S rDNA refer to nucleic acids that are components of, or encode for, components of the ribosome. There are two subunits in the ribosome termed the small subunit (SSU) and large subunit (LSU). Ribosomal RNA genes (rDNA) and their complementary RNA sequences are widely used for determination of the evolutionary relationships among organisms as they are variable, yet sufficiently conserved to allow cross-organism molecular comparisons.

16S rDNA sequence of the 30S SSU can be used, in embodiments, for molecular-based taxonomic assignments of prokaryotes. For example, 16S sequences may be used for phylogenetic reconstruction as they are general highly conserved but contain specific hypervariable regions that harbor sufficient nucleotide diversity to differentiate genera and species of most bacteria. Although 16S rDNA sequence data has been used to provide taxonomic classification, closely related bacterial strains that are classified within the same genus and species, may exhibit distinct biological phenotypes.

The identity of contemplated bacterial strains may be characterized by 16S rRNA, 16S rDNA or full genome sequence analysis. For example, in certain embodiments, contemplated bacterial strains may comprise a 16S rRNA, 16S rDNA and/or genomic sequence having a certain % identity to a reference sequence. A sequence of a bacterial strain described herein, for example, the 16s rRNA gene sequence or a genomic sequence (e.g., a whole genome sequence, or fragments or contigs thereof) of the bacterial strain, can be obtained using any sequencing methods known in the art, including, for example, Sanger sequencing. An example of a sequencing technology useful for identifying bacterial strains is the Illumina™ platform. The Illumina platform is based on amplification of DNA on a solid surface (e.g., flow cell) using fold-back PCR and anchored primers (e.g., capture oligonucleotides). For sequencing with the Illumina platform, bacterial DNA is fragmented, and adapters are added to terminal ends of the fragments. DNA fragments are attached to the surface of flow cell channels by capturing oligonucleotides which are capable of hybridizing to the adapter ends of the fragments. The DNA fragments are then extended and bridge amplified. After multiple cycles of solid-phase amplification followed by denaturation, an array of millions of spatially immobilized nucleic acid clusters or colonies of single-stranded nucleic acids are generated. Each cluster may include approximately hundreds to a thousand copies of single-stranded DNA molecules of the same template. The Illumina platform uses a sequencing-by-synthesis method where sequencing nucleotides comprising detectable labels (e.g., fluorophores) are added successively to a free 3' hydroxyl group. After nucleotide incorporation, a laser light of a wavelength specific for the labeled nucleotides can be used to excite the labels. An image is captured and the identity of the nucleotide base is recorded. These steps can be repeated to sequence the rest of the bases. Sequencing according to this technology is described in, for example, U.S. Patent Publication Application Nos. 2011/0009278, 2007/0014362, 2006/0024681, 2006/0292611, and U.S. Pat. Nos. 7,960,120, 7,835,871, 7,232,656, and 7,115,200. Another example of a sequencing technology useful for identifying bacterial strains is SOLiD™ technology by Applied Biosystems from Life Technologies Corporation (Carlsbad, Calif.). In SOLiD™ sequencing, bacterial DNA may be sheared into fragments, and adapters may be attached to the terminal ends of the fragments to generate a library. Clonal bead populations may be prepared in microreactors containing template, PCR reaction components, beads, and primers. After PCR, the templates can be denatured, and bead enrichment can be performed to separate beads with extended primers. Templates on the selected beads undergo a 3' modification to allow covalent attachment to the slide. The sequence can be determined by sequential hybridization and ligation with several primers. A set of four fluorescently labeled di-base probes compete for ligation to the sequencing primer. Multiple cycles of ligation, detection, and cleavage are performed with the number of cycles determining the eventual read length. Another example of a sequencing technology useful for identifying bacterial strains is Ion Torrent sequencing. In this technology, bacterial DNA is sheared into fragments, and oligonucleotide adapters are then ligated to the terminal ends of the fragments. The fragments are then attached to a surface, and each base in the fragments is resolvable by measuring the $H^+$ ions released during base incorporation. This technology is described in, for example, U.S. Patent Publication Application Nos. 2009/0026082, 2009/0127589, 2010/0035252, 2010/0137143, and 2010/0188073.

Upon obtaining a polynucleotide sequence of a bacterial strain (e.g., 16s rRNA gene sequence or genomic sequence), sequence identity may be determined in various ways that are within the skill in the art, e.g., using publicly available computer software such as BLAST, BLAST-2, BLAT (BLAST-like alignment tool), ALIGN or Megalign (DNASTAR) software. BLAST (Basic Local Alignment Search Tool) analysis using the algorithm employed by the programs blastp, blastn, blastx, tblastn and tblastx (Karlin et al., PROC. NATL. ACAD. SCI. USA 87:2264-2268 (1990); Altschul, J. MOL. EVOL. 36, 290-300 (1993); Altschul et al., NUCLEIC ACIDS RES. 25:3389-3402 (1997)) are tailored for sequence similarity searching. For a discussion of basic issues in searching sequence databases see Altschul et al., NATURE GENETICS 6:119-129 (1994). Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) PROC. NATL. ACAD. SCI. USA 89:10915-10919). Four blastn parameters may be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.:—G, Cost to open gap [Integer]: default=5 for nucleotides/11 for proteins;—E, Cost to extend gap [Integer]: default=2 for nucleotides/1 for proteins;—q. Penalty for nucleotide mismatch [Integer]: default=−3;—r, reward for nucleotide match [Integer]: default=1;—e, expect value [Real]: default=10;—W, wordsize [Integer]: default=11 for nucleotides/28 for megablast/3 for proteins;—y, Dropoff (X) for blast extensions in bits: default=20 for blastn/7 for others;—X. X dropoff value for gapped alignment (in bits): default=15 for all programs, not applicable to blastn; and—

Z, final X dropoff value for gapped alignment (in bits): 50 for blastn, 25 for others). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In certain embodiments, contemplated bacterial strains may comprise a DNA-DNA hybridization (DDH)) value relative to a reference bacterial strain. Any method for determining DNA-DNA hybridization values known in the art may be used to assess the degree of DNA-DNA hybridization, including but not limited to the spectrophotometric method for determining renaturation rates described by De Ley et al. (*J Biochem* 12 133-142 (1970)), slightly modified in hybridization temperature (Gavini et al., *Ecology in Health and Disease* 12 40-45 (2001)); and those described by Grimont et al., *Curr Microbiol* 4, 325-330 (1980) and Rossello-Mora, *Molecular Identification, Systematics and Population Structure of Prokaryotes* pp. 23-50 (2006). In some embodiments, the degree of DNA-DNA hybridization is determined by digital DNA-DNA hybridization (dDDH) analysis, for example, using the Genome-to-Genome Distance Calculator online tool (see Meier-Kolthoff et al., *BMC Bioinformatics* 14:60 (2013)).

In certain embodiments, contemplated bacterial strains may comprise an average nucleotide identity (ANI) relative to a reference bacterial strain. The average nucleotide identity (ANI) of the shared genes between two strains is known to be a robust means to compare genetic relatedness among strains, and that ANI values of ~95% correspond to the 70% DNA-DNA hybridization standard for defining a species. See, e.g., Konstantinidis and Tiedje, *Proc Natl Acad Sci USA*, 102 (7): 2567-72 (2005); and Goris et al., *Int J Syst Evol Microbiol.* 57 (Pt 1): 81-91 (2007). The ANI between two bacterial genomes is calculated from pair-wise comparisons of all sequences shared between any two strains and can be determined, for example, using any of a number of publicly available ANI tools, including but not limited to OrthoANI with usearch (Yoon et al. *Antonie van Leeuwenhoek* 110:1281-1286 (2017)); ANI Calculator, JSpecies (Richter and Rossello-Mora, *Proc Natl Acad Sci USA* 106: 19126-19131 (2009)); and JSpeciesWS (Richter et al., *Bioinformatics* 32:929-931 (2016)). Other methods for determining the ANI of two genomes are known in the art. See, e.g., Konstantinidis, K. T. and Tiedje, J. M., *Proc. Natl. Acad. Sci. U.S.A.*, 102:2567-2572 (2005); and Varghese et al., *Nucleic Acids Research,* 43 (14): 6761-6771 (2015). In a particular embodiment, the ANI between two bacterial genomes can be determined, for example, by averaging the nucleotide identity of orthologous genes identified as bidirectional best hits (BBHs). Protein-coding genes of a first genome (Genome A) and second genome (Genome B) are compared at the nucleotide level using a similarity search tool, for example, NSimScan (Novichkov et al., *Bioinformatics* 32 (15): 2380-23811 (2016). The results are then filtered to retain only the BBHs that display at least 70% sequence identity over at least 70% of the length of the shorter sequence in each BBH pair. The ANI of Genome A to Genome B is defined as the sum of the percent identity times the alignment length for all BBHs, divided by the sum of the lengths of the BBH genes.

In certain embodiments, contemplated bacterial strains may comprise an alignment fraction (AF) relative to a reference bacterial strain. In some embodiments, the AF is computed by dividing the sum of the lengths of all BBH genes by the sum of the length of all the genes in Genome A. This computation is performed separately in both directions: from Genome A to genome B and from Genome B to Genome A.

In some embodiments, a contemplated bacterial strain or bacterial strain mixture (i) reduces or attenuates, or is capable of reducing or attenuating, production of at least one pro-inflammatory gene product, e.g., a pro-inflammatory cytokine or chemokine, in a cell, tissue, or subject; and/or (ii) increases, or is capable of increasing, production of at least one anti-inflammatory gene product, e.g., an anti-inflammatory cytokine or chemokine, in a cell, tissue, or subject. Exemplary pro-inflammatory gene products include IL-1-β, IL-4, IL-5, IL-6, IL-8, IL-12, IL-13, IL-17, IL-21, IL-22, IL-23, IL-27, IFN, CCL-2, CCL-3, CCL-5, CCL-20, CXCL-5, CXCL-10, CXCL-12, CXCL-13, and TNF-α. For example, in some embodiments, a bacterial strain or bacterial strain mixture reduces or attenuates production of IL-12, e.g., IL-12 subunit p40, in a cell, tissue, or subject. Exemplary anti-inflammatory gene products include CCL-18, IL-1Ra, IL-4, IL-6, IL-10, IL-11, IL-13, and TGF-β. For example, a contemplated bacterial strain or bacterial strain mixture increases production of IL-10 and/or CCL-18, in a cell, tissue, or subject. It is understood that a gene product may have both pro- and/or anti-inflammatory activity.

A contemplated bacterial strain or bacterial strain mixture may be characterized as having an effect on gene product production, e.g., IL-10, IL-12, or CCL-18 production, in an immune cell, e.g., a macrophage (e.g., a THP-1 macrophage) or PBMC (including lymphocytes (T cells, B cells, NK cells) and monocytes). In vivo, major sources of IL-10 include T helper cells, monocytes, macrophages and dendritic cells, however myriad immune effector cell types are capable of producing IL-10 in certain contexts including B cells, cytotoxic T cells, NK cells, mast cells, and granulocytes like neutrophils and eosinophils. Gene product production, e.g., IL-10. IL-12, or CCL-18, in a macrophage may, for example, be assayed as follows. THP-1 human macrophages are made by culturing the THP-1 human monocyte cell line with phorbol 12-myristate 13-acetate (PMA) for 24 hours, optionally followed by IL-4 and IL-13 as described previously (Genin et al., *BMC Cancer* 15:577 (2015)). A bacterial strain or bacterial strain mixture is incubated with THP-1 macrophages in the presence of lipopolysaccharide (LPS) for 24 hours. Gene product production is assessed by measuring the concentration of the gene product, e.g., IL-10, IL-12, or CCL-18, in the cell culture supernatant by ELISA. Gene product production may also be assayed as described in Sudhakaran et al., *Genes Nutr.,* 8 (6): 637-48 (2013). Gene product production, e.g., IL-10, IL-12, or CCL-18 production, in a PBMC may, for example, be assayed as follows. Primary PBMCs are isolated from blood samples of donors using a percoll gradient (Sim et al., *J. Vis. Exp.* (112), e54128 (2016)). A bacterial strain or bacterial strain mixture is incubated with PBMCs for 24 hours. Gene product production is assessed by measuring the concentration of the gene product, e.g., IL-10, IL-12, or CCL-18, in the cell culture supernatant by ELISA.

A contemplated bacterial strain or bacterial strain mixture may (i) reduce or prevent disruption to, or increase, or be capable of reducing or preventing disruption to, or increasing, the integrity of an epithelial barrier (e.g., an epithelial cell monolayer); and/or (ii) increase, or be capable of increasing, production of at least one pro-barrier integrity gene (e.g., ZO-1) in a cell, tissue, or subject. In some embodiments, the epithelial barrier is an intestinal barrier, e.g., an intestinal mucosal barrier. The intestinal epithelium is organized in a single layer of 20 μm, and includes 5 different cell types: enterocytes, endocrine cells, M cells, goblet (mucous) cells and Paneth cells. The enterocytes are the most represented cell type, acting as a physical barrier, inhibiting the translocation of luminal contents in the inner tissues. They are connected by intercellular junctions, characterized by transmembrane proteins that interact with near cells and with intracellular proteins associated with the cytoskeleton. Contemplated bacterial strains or bacterial strain mixtures may be characterized by an effect on the integrity of an epithelial barrier, e.g., a HT29MTX-E12 cell monolayer or a Caco-2 monolayer, or any intestinal epithelial cell or cell line monolayer. In certain embodiments, contemplated bacterial strains or bacterial strain mixtures may be characterized by an effect on barrier integrity of a human epithelial cell monolayer, e.g., a HT29MTX-E12 cell monolayer or a Caco-2 monolayer, treated with TNF-α. Barrier integrity of a HT29MTX-E12 cell monolayer treated with TNF-α may, for example, be assayed as follows. HT29MTX-E12 cells are seeded into a transwell plate system for 18-21 days to form polarized monolayers as described previously (Hall et al., *Journal of Pediatric Surgery* 48:353-358 (2013)). A bacterial strain or bacterial strain mixture is added to the apical layer of the transwell followed by the addition of TNF-α to the basal layer of the transwell, thus modeling an inflamed gut. The monolayer integrity is assessed by measuring the trans-epithelial electrical resistance (TEER) across the cell barrier at 0 and 24 hours after TNF-α addition. Barrier integrity may also be assayed as described in Pontier et al., J. Pharm. Sci., 90 (10): 1608-19 (2001).

In a particular embodiment, identification of a bacterial strain or bacterial strain mixture that reduces or prevents the disruption of the integrity of an epithelial barrier (e.g., an epithelial cell monolayer), or increases its integrity, identifies the bacterial strain or bacterial strain mixture as capable of reducing or preventing the disruption of, or increasing, the integrity of an intestinal barrier, e.g., an intestinal mucosal barrier. Thus, in another aspect, provided herein are methods of selecting a bacterial strain or bacterial strain mixture having gut barrier protective properties. Also provided herein are methods of selecting a bacterial strain or bacterial strain mixture for use in the treatment of gastrointestinal disorders, dysbiosis, and/or inflammatory disorders described herein. In some embodiments, the methods comprise the steps of: (a) contacting in vitro an epithelial cell monolayer with a bacterial strain or bacterial strain mixture; (b) contacting the epithelial cell monolayer with a pro-inflammatory compound in the presence of the bacterial strain or bacterial strain mixture; and (c) measuring the trans-epithelial electrical resistance (TEER) across the cell monolayer; wherein an increase in TEER across the cell monolayer compared to a cell monolayer (e.g., of the same cell type) contacted with the pro-inflammatory compound but not contacted with the bacterial strain or bacterial strain mixture identifies the bacterial strain or bacterial strain mixture as having gut barrier protective properties, and/or useful for the treatment of a gastrointestinal disorders, dysbiosis, and/or an inflammatory disorder. In some embodiments, the epithelial cell monolayer is a human epithelial cell monolayer. In some embodiments, the epithelial cell monolayer is a mucosal epithelial cell monolayer. In some embodiments, the epithelial cell monolayer is a HT29MTX-E12 cell monolayer or a Caco-2 cell monolayer. In some embodiments, the bacterial strain or bacterial strain mixture contacts the apical side of the epithelial cell monolayer. In some embodiments, the contacting of the epithelial cell monolayer with the bacterial strain or bacterial strain mixture occurs for at least 10, 20, 30, 40, 50, 60, 80, 100, 120, 140, 160, 180, 200, 220, 240 or greater than 240 minutes prior to the contacting of the epithelial cell layer with the pro-inflammatory compound. In some embodiments, the pro-inflammatory compound is selected from the group consisting of IL-1-β, IL-4, IL-5, IL-6, IL-8, IL-12, IL-13, IL-17, IL-21, IL-22, IL-23, IL-27, IFN, CCL-2, CCL-3, CCL-5, CCL-20, CXCL-5, CXCL-10, CXCL-12, CXCL-13, and TNF-α. In some embodiments, the measuring of the TEER across the cell monolayer occurs at 0, 1, 2, 3, 4, 5, 6, 7, 8, 9, 10, 11, 12, 13, 14, 15, 16, 17, 18, 19, 20, 21, 22, 23, 24 and/or greater than 24 hours after contacting the epithelial cell monolayer with the pro-inflammatory compound. In some embodiments, the increase in TEER across the cell monolayer is at least 5%, 10%, 20%, 25%, 30%, 35%, 40%, 45%, 50%, 55%, 60%, 65%, 70%, 75%, 80%, 85%, 90%, 95%, 100% or greater than 100% compared to a cell monolayer contacted with the pro-inflammatory compound but not contacted with the bacterial strain or bacterial strain mixture.

Contemplated bacterial strains or bacterial strain mixtures may induce or increase, or be capable of inducing or increasing, autophagy in a cell, e.g., an antigen presenting cell, epithelial cell, myeloid cell, enterocyte, macrophage (e.g., a THP-1 macrophage), PBMC (including lymphocytes (T cells, B cells, NK cells) and monocytes), dendritic cells, mast cells, and granulocytes like neutrophils and/or an eosinophils. Autophagy is an intracellular degradation system, where dysfunctional proteins and organelles are degraded. In this process, aggregated dysfunctional proteins are surrounded by a double membrane to form an autophagosome. Induction of autophagy in a cell, e.g., a THP-1 macrophage, may be assayed as follows. THP-1 human macrophages are made by culturing the THP-1 human monocyte cell line with phorbol 12-myristate 13-acetate (PMA) for 24 hours, optionally followed by IL-4 and IL-13 as described previously (Genin et al., *BMC Cancer* 15:577 (2015)). A bacterial strain or bacterial strain mixture is incubated with THP-1 macrophages in the presence of lipopolysaccharide (LPS) for at least 1, 2, 3 or more hours (for example, up to 24 hours). Autophagy can be assayed by detection of autophagosome formation, for example by staining cells with a fluorescent dye that accumulates in membranes specific to autophagosomes, such as the Cyto-ID® (Enzo Life Sciences) or DAPGreen (Dojindo Molecular Technologies, Inc.). Autophagy may also be detected by any method described by Puleston et al., Cold *Spring Harb Protoc*; doi: 10.1101/pdb.top070391.

Thus, in another aspect, provided herein are methods of selecting a bacterial strain or bacterial strain mixture for use in the treatment of gastrointestinal disorders, dysbiosis, and/or inflammatory disorders, the methods comprising the steps of: (a) contacting in vitro a cell with a bacterial strain or bacterial strain mixture; and (b) measuring autophagy in the cell; wherein an increase in autophagy in the cell compared to a cell (e.g., of the same cell type) not contacted with the bacterial strain or bacterial strain mixture identifies the bacterial strain or bacterial strain mixture as useful for the treatment of a gastrointestinal disorders, dysbiosis, and/or an inflammatory disorder. In some embodiments, the cell is a human cell. In some embodiments, the cell is an antigen presenting cell, epithelial cell, myeloid cell, enterocyte, macrophage (e.g., a THP-1 macrophage), PBMC (including lymphocytes (T cells, B cells, NK cells) and monocytes), dendritic cell, mast cell, or granulocyte (e.g., neutrophil or eosinophil). In some embodiments, the monocyte or macrophage is a THP-1 monocyte or macrophage. In some embodiments, the gastrointestinal disorder is inflammatory bowel disease, including ulcerative colitis and Crohn's disease. In some embodiments, the contacting occurs in the presence of lipopolysaccharide (LPS). In some embodiments, the contacting occurs for at least 1, 2, 3, 4, 5, 6, 7, 8, 9, 10, 11, 12, 13, 14, 15, 16, 17, 18, 19, 20, 21, 22, 23, 24 or greater than 24 hours prior to measuring autophagy.

Contemplated bacterial strains or bacterial strain mixtures may reduce or attenuate, or be capable of reducing or attenuating, production of Lipocalin-2/NGAL in a cell, tissue or subject. Lipocalin-2 (LCN2), also referred to as neutrophil gelatinase-associated lipocalin (NGAL) or siderocalin, is a potent bacteriostatic protein stored in neutrophil granules and released at sites of inflammation. High LCN2 expression by gut epithelial cells has been demonstrated in colonic biopsies from inflamed areas of patients with IBD (Nielsen et al., Gut, 38:414-420 (1996)), and LCN2 has been reported to be among the 10 most upregulated genes in both active ulcerative colitis and Crohn's disease (Ostvik et al., *Clin Exp Immunol.* 173:502-511 (2013)). Ostvik reported that although LCN2 protein was found in both epithelial cells and infiltrating neutrophils, LCN2 mRNA synthesis solely took place in epithelial cells indicating that the excessive de novo synthesis of LCN2 in IBD is localized in the colonic epithelium. Serum levels of LCN2 has been demonstrated to be a reliable biomarker of disease activity in UC, distinguishing active disease from disease in remission with a greater sensitivity than CRP or white blood cell count (Stallhofer et al., *Inflamm Bowel Dis* 21 (10): 2327-2340 (2015)). Levels of LCN2/NGAL can be assessed in a cell, tissue or subject contacted with a contemplated bacterial strain or bacterial strain mixture by measuring the expression and/or concentration of the LCN2/NGAL gene product in a sample, e.g., plasma, serum, stool and/or tissue (e.g., colonic tissue), by any method known in the art, including qPCR, ELISA, immunohistochemistry or the like.

As described below, cell bank preparation/vegetative bacterial strains contemplated herein may, e.g., be prepared for example without animal-derived components in the media used in the isolation and preparation of master cell banks.

A contemplated bacterial strain, for example, for use in a disclosed bacterial strain mixture, pharmaceutical composition or unit, or method, includes a *Bacteroides* species strain. Exemplary *Bacteroides* species include *B. acidifaciens, B. barnesiaes, B. caccae, B. caecicola, B. caecigallinarum, B. cellulosilyticus, B. cellulosolvens, B. clarus, B. coagulans, B. coprocola, B. coprophilus, B. coprosuis, B. distasonis, B. dorei, B. eggerthii, B. gracilis, B. faecichinchillae, B. faecis, B. finegoldii, B. fluxus, B. fragilis, B. galacturonicus, B. gallinaceum, B. gallinarum, B. goldsteinii, B. graminisolvens, B. helcogene, B. intestinalis, B. luti, B. massiliensis, B. melaninogenicus, B. nordii, B. oleiciplenus, B. oris, B. ovatus, B. paurosaccharolyticus, B. pectinophilus, B. plebeius, B. polypragmatus, B. propionicifaciens, B. putredinis, B. pyogenes, B. reticulotermitis, B. rodentium, B. salanitronis, B. salyersiae, B. sartorii, B. sediment B. stercoris, B. suis, B. tectus, B. thetaiotaomicron, B. uniformis, B. vulgatus, B. xylanisolvens*, and *B. xylanolyticusxylanolyticus*. Those of skill in the art will recognize that the genus *Bacteroides* may undergo taxonomical reorganization. Thus, it is intended that contemplated *Bacteroides* species include *Bacteroides* species that have been renamed and/or reclassified, as well as those that may be later renamed and/or reclassified.

In certain embodiments, a contemplated *Bacteroides* species strain is a *Bacteroides thetaiotaomicron* strain. For example, a contemplated *Bacteroides thetaiotaomicron* strain genome may comprise a 16s rRNA gene sequence having the nucleotide sequence of SEQ ID NO: 2, or a 16s rRNA gene sequence having at least about 70.0%, about 80.0%, about 90.0%, about 91.0%, about 92.0%, about 93.0%, about 94.0%, about 95.0%, about 96.0%, about 97.0%, about 98.0%, about 98.1%, about 98.2%, about 98.3%, about 98.4%, about 98.5%, about 98.6%. about 98.7%, about 98.8%, about 98.9%, about 99.0%, about 99.1%, about 99.2%, about 99.3%. about 99.4%, about 99.5%, about 99.6%, about 99.7%, about 99.8%, or about 99.9% identity to the nucleotide sequence of SEQ ID NO: 2. In some embodiments, the sequence identity referred to above is across at least about 70% of SEQ ID NO: 2. In other embodiments, the sequence identity referred to above is across at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of SEQ ID NO: 2.

In some embodiments, a contemplated *Bacteroides thetaiotaomicron* strain comprises a genomic sequence (e.g., a whole genome sequence, or fragments or contigs thereof) having a certain % identity to one or more of SEQ ID NOs: 33-390. A contemplated *Bacteroides thetaiotaomicron* strain genome may comprise the nucleotide sequence of any one of SEQ ID NOs: 33-390, or a nucleotide sequence having at least about 65%, about 70%, about 75%, about 80%, about 85%, about 90%, about 91%, about 92%, about 93%, about 94%, about 95%, about 96%, about 97%, about 98%, or about 99% identity to the nucleotide sequence of any one of SEQ ID NOs: 33-390. A contemplated *Bacteroides thetaiotaomicron* strain genome may comprise the nucleotide sequence of each of SEQ ID NOs: 33-390, or each of a nucleotide sequence having at least about 65%, about 70%, about 75%, about 80%, about 85%, about 90%, about 91%, about 92%, about 93%, about 94%, about 95%, about 96%, about 97%, about 98%, or about 99% identity to the nucleotide sequence of each of SEQ ID NOs: 33-390.

In some embodiments, a contemplated *Bacteroides thetaiotaomicron* strain comprises a whole genomic sequence having at least about 70% identity across at least 70% of its genome to the sum of all genomic contigs represented by SEQ ID NOs: 33-390. In some embodiments, the whole genomic sequence has at least about 75%, 80%, 85%, 90%, 95% or greater than 95% identity to the sum of all genomic contigs represented by SEQ ID NOs: 33-390. In some embodiments, the sequence identity referred to above is across at least 75%, 80%, 85%, 90%, 95% or greater than 95% of the whole genomic sequence of the bacterial strain. In some embodiments, a contemplated *Bacteroides thetaiotaomicron* strain comprises a whole genomic sequence comprising coding regions having at least about 70% identity across at least 70% of the total coding regions in its genome to the coding regions within the sum of all genomic contigs represented by SEQ ID NOs: 33-390. In some embodiments, the coding regions within the whole genomic sequence have at least about 75%, 80%, 85%, 90%, 95% or greater than 95% identity to the coding regions within the sum of all genomic contigs represented by SEQ ID NOs: 33-390. In some embodiments, the sequence identity referred to above is across at least 75%, 80%, 85%, 90%, 95% or greater than 95% of the coding regions within the whole genomic sequence of the bacterial strain.

In certain embodiments, a contemplated *Bacteroides* species strain, e.g., a *Bacteroides thetaiotaomicron* strain, increases, or is capable of increasing, production of at least one anti-inflammatory gene product in a cell, tissue, or subject. For example, a contemplated *Bacteroides* species strain, e.g., a *Bacteroides thetaiotaomicron* strain, increases production of IL-10 and/or CCL-18 in a human cell, e.g., a THP-1 macrophage or monocyte or a PBMC. For example, contacting a human cell, e.g., a THP-1 macrophage or PBMC, with the *Bacteroides* species strain, e.g., a *Bacteroides thetaiotaomicron* strain, may increase production of IL-10 and/or CCL-18 in the cell by at least about 10%, at least about 20%, at least about 30%, at least about 40%, at least about 50%, at least about 75%, at least about 100%, at least about 200%, at least about 300%, at least about 400%, at least about 500%, at least about 750%, at least about 1000%, from about 10% to about 20%, from about 10% to about 50%, from about 10% to about 100%, from about 10% to about 200%, from about 10% to about 500%, from about 10% to about 1000%, from about 20% to about 50%, from about 20% to about 100%, from about 20% to about 200%, from about 20% to about 500%, from about 20% to about 1000%, from about 50% to about 100%, from about 50% to about 200%, from about 50% to about 500%, from about 50% to about 1000%, from about 100% to about 200%, from about 100% to about 500%, from about 100% to about 1000%, from about 200% to about 500%, from about 200% to about 1000%, or from about 500% to about 1000%, relative to a cell (e.g., of the same cell type) that was not contacted with the strain. In some embodiments, the contacting of the human cell with the *Bacteroides* species strain occurs in vitro, e.g., the human cell is incubated with the *Bacteroides* species strain. In some embodiments, the contacting of the human cell with the *Bacteroides* species strain occurs in vivo.

In certain embodiments, a contemplated *Bacteroides* species strain, e.g., a *Bacteroides thetaiotaomicron* strain, reduces or attenuates, or is capable of reducing or attenuating, production of at least one pro-inflammatory gene product in a cell, tissue, or subject. For example, a contemplated *Bacteroides* species strain, e.g., a *Bacteroides thetaiotaomicron* strain, reduces or attenuates production of IL-6, IL-12, IL-17 and/or TNF-α in a human cell, e.g., a THP-1 macrophage or monocyte or a PBMC. For example, contacting a human cell, e.g., a THP-1 macrophage or PBMC, with the *Bacteroides* species strain, e.g., a *Bacteroides thetaiotaomicron* strain, may reduce or attenuate production of IL-6, IL-12, IL-17 and/or TNF-α in the cell by at least about 10%, at least about 20%, at least about 30%, at least about 40%, at least about 50%, at least about 75%, from about 10% to about 20%, from about 10% to about 50%, from about 10% to about 100%, from about 20% to about 50%, from about 20% to about 100%, or from about 50% to about 100%, relative to a cell (e.g., of the same cell type) that was not contacted with the strain. In some embodiments, the contacting of the human cell with the *Bacteroides* species strain occurs in vitro, e.g., the human cell is incubated with the *Bacteroides* species strain. In some embodiments, the contacting of the human cell with the *Bacteroides* species strain occurs in vivo.

In certain embodiments, a contemplated *Bacteroides* species strain, e.g., a *Bacteroides thetaiotaomicron* strain, reduces or prevents disruption to, or increases, or is capable of reducing or preventing disruption to, or increasing, barrier integrity of a mucosal epithelium. For example, a contemplated *Bacteroides* species strain, e.g., a *Bacteroides thetaiotaomicron* strain, may reduce or prevent disruption of, or increase, barrier integrity of a HT29MTX-E12 cell monolayer, e.g., a HT29MTX-E12 cell monolayer treated with TNF-α. For example, incubation of a contemplated *Bacteroides* species strain, e.g., a *Bacteroides thetaiotaomicron* strain, with a HT29MTX-E12 cell monolayer, e.g., a HT29MTX-E12 cell monolayer treated with TNF-α, may reduce or prevent disruption of, or increase, barrier integrity, e.g., as measured by trans-epithelial electrical resistance (TEER), by at least about 10%, at least about 20%, at least about 30%, at least about 40%, at least about 50%, at least about 60%, at least about 70%, at least about 80%, at least about 90%, at least about 100%, from about 20% to about 100%, from about 40% to about 100%, from about 60% to about 100%, from about 80% to about 100%, from about 20% to about 80%, from about 40% to about 80%, from about 60% to about 80%, from about 20% to about 60%, from about 40% to about 60%, or from about 20% to about 40%, relative to a HT29MTX-E12 cell monolayer that was not incubated with a contemplated strain.

In certain embodiments, a contemplated *Bacteroides* species strain, e.g., a *Bacteroides thetaiotaomicron* strain, induces or increases, or is capable of inducing or increasing, autophagy in a cell, tissue, or subject. For example, a contemplated *Bacteroides* species strain, e.g., a *Bacteroides thetaiotaomicron* strain, induces or increases autophagy in a human cell, e.g., a THP-1 macrophage. For example, contacting a human cell, e.g., a THP-1 macrophage, with the *Bacteroides* species strain, e.g., a *Bacteroides thetaiotaomicron* strain, may induce or increase autophagy in the cell by at least about 10%, at least about 20%, at least about 30%, at least about 40%, at least about 50%, at least about 60%, at least about 70%, at least about 80%, at least about 90%, at least about 100%, from about 10% to about 20%, from about 10% to about 50%, from about 10% to about 100%, from about 20% to about 50%, from about 20% to about 100%, from about 20% to about 200%, from about 50% to about 100%, or from about 50% to about 200%, relative to a cell (e.g., of the same cell type) that was not contacted with the strain. In some embodiments, the contacting of the human cell with the *Bacteroides* species strain occurs in vitro, e.g., the human cell is incubated with the *Bacteroides* species strain. In some embodiments, the contacting of the human cell with the *Bacteroides* species strain occurs in vivo.

In certain embodiments, a contemplated *Bacteroides* species strain, e.g., a *Bacteroides thetaiotaomicron* strain, reduces or attenuates, or is capable of reducing or attenuating, production of Lipocalin-2/NGAL in a cell, tissue, or subject. For example, contacting a human cell with a *Bacteroides* species strain, e.g., a *Bacteroides thetaiotaomicron* strain may reduce or attenuate production of Lipocalin-2/NGAL in the cell by at least about 10%, at least about 20%, at least about 30%, at least about 40%, at least about 50%, at least about 75%, from about 10% to about 20%, from about 10% to about 50%, from about 10% to about 100%, from about 20% to about 50%, from about 20% to about 100%, or from about 50% to about 100%, relative to a cell (e.g., of the same cell type) that was not contacted with the strain. In some embodiments, the contacting of the human cell with the *Bacteroides* species strain occurs in vitro, e.g., the human cell is incubated with the *Bacteroides* species strain. In some embodiments, the contacting of the human cell with the *Bacteroides* species strain occurs in vivo.

In certain embodiments, a contemplated *Bacteroides thetaiotaomicron* strain is the strain identified herein as BTH01. A deposit of *Bacteroides thetaiotaomicron* strain BTH01 (P118-A12a) was made to DSMZ (Deutsche Sammlung von Mikroorganismen and Zellkulturen GmbH, Inhoffenstraße 7B, 38124 Brunswick, Germany) under the Budapest Treaty on the International Recognition of the Deposit of Microorganisms for the Purposes of Patent Procedure on Sep. 14, 2018. This deposit was accorded accession number DSM-32919. The 16s rRNA gene sequence of *Bacteroides thetaiotaomicron* strain BTH01 is provided herein as SEQ ID NO: 2, and genomic sequences of *Bacteroides thetaiotaomicron* strain BTH01 are provided herein as SEQ ID NOs: 33-390.

In certain embodiments, a contemplated *Bacteroides thetaiotaomicron* strain has a DNA-DNA hybridization (DDH) value of equal to or greater than about 70% with *Bacteroides thetaiotaomicron* strain BTH01 (P118-A12a). In certain embodiments, the *Bacteroides thetaiotaomicron* strain is one having greater than about 70%, about 75%, about 80%, about 85%, about 90%, about 95%, about 98% or about 99% DNA-DNA hybridization with *Bacteroides thetaiotaomicron* strain BTH01 (P118-A12a). In certain embodiments, a contemplated *Bacteroides thetaiotaomicron* strain has equal to or greater than 95% average nucleotide identity (ANI) with *Bacteroides thetaiotaomicron* strain BTH01 (P118-A12a). In certain embodiments, the ANI is equal to or greater than about 95%, about 95.5%, about 96%, about 96.5%, about 97%, about 97.5%, about 98%, about 98.5%, about 99%, about 99.5%, or 100%. In certain embodiments, a contemplated *Bacteroides thetaiotaomicron* strain has equal to or greater than 60% alignment fraction (AF) with *Bacteroides thetaiotaomicron* strain BTH01 (P118-A12a). In certain embodiments, the AF is equal to or greater than about 65%, about 70%, about 75%, about 80%, about 85%, about 90%, about 95%, or 100%.

A contemplated bacterial strain, for example, for use in a disclosed bacterial strain mixture, pharmaceutical composition or unit, or method, includes a *Eubacterium* species strain. Exemplary *Eubacterium* species include *E. aggregans, E. angustum, E. barkeri, E. brachy, E. budayi, E. callanderi, E. cellulosolvens, E. combesii, E. coprostanoligenes, E. dolichum, E. eligens, E. hallii, E. infirmum, E. limosum, E. minutum, E. multiforme, E. nitritogenes, E. nodatum, E. oxidoreducens, E. plexicaudatum, E. pyruvativorans, E. ramulus, E. rectale, E. ruminantium, E. saphenum, E. siraeum, E. sulci, E. tarantellae, E. tenue, E. tortuosum, E. uniforme, E. ventriosum, E. xylanophilum*, and *E. yurii*. Those of skill in the art will recognize that the genus *Eubacterium* may undergo taxonomical reorganization. Thus, it is intended that a contemplated *Eubacterium* species include *Eubacterium* species that have been renamed and/or reclassified, as well as those that may be later renamed and/or reclassified. For example, contemplated strains of *Eubacterium hallii* includes those reclassified as *Anaerobutyricum hallii* (Shetty et al., *Int J Syst Evol Microbiol.* 68:3741-3746 (2018)).

In certain embodiments, a contemplated *Eubacterium* species strain is a *Eubacterium hallii* strain. For example, a contemplated *Eubacterium hallii* strain genome may comprise a 16s rRNA gene sequence having the nucleotide sequence of SEQ ID NO: 3, or a 16s rRNA gene sequence having at least about 70.0%, about 80.0%, about 90.0%, about 91.0%, about 92.0%, about 93.0%, about 94.0%, about 95.0%, about 96.0%, about 97.0%, about 98.0%, about 98.1%, about 98.2%, about 98.3%, about 98.4%, about 98.5%, about 98.6%, about 98.7%, about 98.8%, about 98.9%, about 99.0%, about 99.1%, about 99.2%, about 99.3%, about 99.4%, about 99.5%, about 99.6%, about 99.7%, about 99.8%, or about 99.9% identity to the nucleotide sequence of SEQ ID NO: 3. In some embodiments, the sequence identity referred to above is across at least about 70% of SEQ ID NO: 3. In other embodiments, the sequence identity referred to above is across at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of SEQ ID NO: 3.

In some embodiments, a contemplated *Eubacterium hallii* strain comprises a genomic sequence (e.g., a whole genome sequence, or fragments or contigs thereof) having a certain % identity to one or more of SEQ ID NOs: 391-523. A contemplated *Eubacterium hallii* strain genome may comprise the nucleotide sequence of any one of SEQ ID NOs: 391-523, or a nucleotide sequence having at least about 65%, about 70%, about 75%, about 80%, about 85%, about 90%, about 91%, about 92%, about 93%, about 94%, about 95%, about 96%, about 97%, about 98%, or about 99% identity to the nucleotide sequence of any one of SEQ ID NOs: 391-523. A contemplated *Eubacterium hallii* strain genome may comprise the nucleotide sequence of each of SEQ ID NOs: 391-523, or each of a nucleotide sequence having at least about 65%, about 70%, about 75%, about 80%, about 85%, about 90%, about 91%, about 92%, about 93%, about 94%, about 95%, about 96%, about 97%, about 98%, or about 99% identity to the nucleotide sequence of each of SEQ ID NOs: 391-523.

In some embodiments, a contemplated *Eubacterium hallii* strain comprises a whole genomic sequence having at least about 70% identity across at least 70% of its genome to the sum of all genomic contigs represented by SEQ ID NOs: 391-523. In some embodiments, the whole genomic sequence has at least about 75%, 80%, 85%, 90%, 95% or greater than 95% identity to the sum of all genomic contigs represented by SEQ ID NOs: 391-523. In some embodiments, the sequence identity referred to above is across at least 75%, 80%, 85%, 90%, 95% or greater than 95% of the whole genomic sequence of the bacterial strain. In some embodiments, a contemplated *Eubacterium hallii* strain comprises a whole genomic sequence comprising coding regions having at least about 70% identity across at least 70% of the total coding regions in its genome to the coding regions within the sum of all genomic contigs represented by SEQ ID NOs: 391-523. In some embodiments, the coding regions within the whole genomic sequence have at least about 75%, 80%, 85%, 90%, 95% or greater than 95% identity to the coding regions within the sum of all genomic contigs represented by SEQ ID NOS: 391-523. In some embodiments, the sequence identity referred to above is across at least 75%, 80%, 85%, 90%, 95% or greater than 95% of the coding regions within the whole genomic sequence of the bacterial strain.

In certain embodiments, a contemplated *Eubacterium* species strain, e.g., a *Eubacterium hallii* strain, increases, or is capable of increasing, production of at least one anti-inflammatory gene product in a cell, tissue, or subject. For example, a contemplated *Eubacterium* species strain, e.g., a *Eubacterium hallii* strain, increases production of IL-10 and/or CCL-18 in a human cell, e.g., a THP-1 macrophage or monocyte or a PBMC. For example, contacting a human cell, e.g., a THP-1 macrophage or a PBMC, with the *Eubacterium* species strain, e.g., a *Eubacterium hallii* strain, may increase production of IL-10 and/or CCL-18 in the cell by at least about 10%, at least about 20%, at least about 30%, at least about 40%, at least about 50%, at least about 75%, at least about 100%, at least about 200%, at least about 300%, at least about 400%, at least about 500%, at least about 750%, at least about 1000%, from about 10% to about 20%, from about 10% to about 50%, from about 10% to about 100%, from about 10% to about 200%, from about 10% to about 500%, from about 10% to about 1000%, from about 20% to about 50%, from about 20% to about 100%, from about 20% to about 200%, from about 20% to about 500%, from about 20% to about 1000%, from about 50% to about 100%, from about 50% to about 200%, from about 50% to about 500%, from about 50% to about 1000%, from about 100% to about 200%, from about 100% to about 500%, from about 100% to about 1000%, from about 200% to about 500%, from about 200% to about 1000%, or from about 500% to about 1000%, relative to a cell (e.g., of the same cell type) that was not contacted with the strain. In some embodiments, the contacting of the human cell with the *Eubacterium* species strain occurs in vitro, e.g., the human cell is incubated with the *Eubacterium* species strain. In some embodiments, the contacting of the human cell with the *Eubacterium* species strain occurs in vivo.

In certain embodiments, a contemplated *Eubacterium* species strain, e.g., a *Eubacterium hallii* strain, reduces or attenuates, or is capable of reducing or attenuating, production of at least one pro-inflammatory gene product in a cell, tissue, or subject. For example, a contemplated *Eubacterium* species strain, e.g., a *Eubacterium hallii* strain, reduces or attenuates production of IL-6, IL-12, IL-17 and/or TNF-α in a human cell, e.g., a THP-1 macrophage or monocyte or a PBMC. For example, contacting a human cell, e.g., a THP-1 macrophage or PBMC, with the *Eubacterium* species strain, e.g., a *Eubacterium hallii* strain, may reduce or attenuate production of IL-6, IL-12, IL-17 and/or TNF-α in the cell by at least about 10%, at least about 20%, at least about 30%, at least about 40%, at least about 50%, at least about 75%, from about 10% to about 20%, from about 10% to about 50%, from about 10% to about 100%, from about 20% to about 50%, from about 20% to about 100%, or from about 50% to about 100%, relative to a cell (e.g. of the same cell type) that was not contacted with the strain. In some embodiments, the contacting of the human cell with the *Eubacterium* species strain occurs in vitro, e.g., the human cell is incubated with the *Eubacterium* species strain. In some embodiments, the contacting of the human cell with the *Eubacterium* species strain occurs in vivo.

In certain embodiments, a contemplated *Eubacterium* species strain, e.g., a *Eubacterium hallii* strain, reduces or prevents disruption to, or increases, or is capable of reducing or preventing disruption to, or increasing, barrier integrity of a mucosal epithelium. For example, a contemplated *Eubacterium* species strain, e.g., a *Eubacterium hallii* strain, reduces or prevents disruption of, or increases, barrier integrity of a HT29MTX-E12 cell monolayer, e.g., a HT29MTX-E12 cell monolayer treated with TNF-α. For example, incubation of a *Eubacterium* species strain, e.g., a *Eubacterium hallii* strain, with a HT29MTX-E12 cell monolayer, e.g., a HT29MTX-E12 cell monolayer treated with TNF-α, may reduce or prevent disruption of, or increase, barrier integrity, e.g., as measured by trans-epithelial electrical resistance (TEER), by at least about 10%, at least about 20%, at least about 30%, at least about 40%, at least about 50%, at least about 60%, at least about 70%, at least about 80%, at least about 90%, at least about 100%, from about 20% to about 100%, from about 40% to about 100%, from about 60% to about 100%, from about 80% to about 100%, from about 20% to about 80%, from about 40% to about 80%, from about 60% to about 80%, from about 20% to about 60%, from about 40% to about 60%, or from about 20% to about 40%, relative to a HT29MTX-E12 cell monolayer that was not incubated with the strain.

In certain embodiments, a contemplated *Eubacterium* species strain, e.g., a *Eubacterium hallii* strain, induces or increases, or is capable of inducing or increasing, autophagy in a cell, tissue, or subject. For example, a contemplated *Eubacterium* species strain, e.g., a *Eubacterium hallii* strain, induces or increases autophagy in a human cell, e.g., a THP-1 macrophage. For example, contacting a human cell, e.g., a THP-1 macrophage, with the *Eubacterium* species strain, e.g., a *Eubacterium hallii* strain, may induce or increase autophagy in the cell by at least about 10%, at least about 20%, at least about 30%, at least about 40%, at least about 50%, at least about 60%, at least about 70%, at least about 80%, at least about 90%, at least about 100%, from about 10% to about 20%, from about 10% to about 50%, from about 10% to about 100%, from about 20% to about 50%, from about 20% to about 100%, from about 20% to about 200%, from about 50% to about 100%, or from about 50% to about 200%, relative to a cell (e.g., of the same cell type) that was not contacted with the strain. In some embodiments, the contacting of the human cell with the *Eubacterium* species strain occurs in vitro, e.g., the human cell is incubated with the *Eubacterium* species strain. In some embodiments, the contacting of the human cell with the *Eubacterium* species strain occurs in vivo.

In certain embodiments, a contemplated *Eubacterium* species strain, e.g., a *Eubacterium hallii* strain, reduces or attenuates, or is capable of reducing or attenuating, production of Lipocalin-2/NGAL in a cell, tissue, or subject. For example, contacting a human cell with a *Eubacterium* species, e.g., a *Eubacterium hallii* strain may reduce or attenuate production of Lipocalin-2/NGAL in the cell by at least about 10%, at least about 20%, at least about 30%, at least about 40%, at least about 50%, at least about 75%, from about 10% to about 20%, from about 10% to about 50%, from about 10% to about 100%, from about 20% to about 50%, from about 20% to about 100%, or from about 50% to about 100%, relative to a cell (e.g., of the same cell type) that was not contacted with the strain. In some embodiments, the contacting of the human cell with the *Eubacterium* species strain occurs in vitro, e.g., the human cell is incubated with the *Eubacterium* species strain. In some embodiments, the contacting of the human cell with the *Bacteroides* species strain occurs in vivo.

In certain embodiments, a contemplated *Eubacterium hallii* strain is the strain identified herein as EHA01. A deposit of *Eubacterium hallii* strain EHA01 (P168-Fla) was made to DSMZ (Deutsche Sammlung von Mikroorganismen and Zellkulturen GmbH, Inhoffenstraße 7B, 38124 Brunswick, Germany) under the Budapest Treaty on the International Recognition of the Deposit of Microorganisms for the Purposes of Patent Procedure on Sep. 14, 2018. This deposit was accorded accession number DSM-32920. The 16s rRNA gene sequence of *Eubacterium hallii* strain EHA01 is provided herein as SEQ ID NO: 3, and genomic sequences of *Eubacterium hallii* strain EHA01 are provided herein as SEQ ID NOs: 391-523.

In certain embodiments, a contemplated *Eubacterium hallii* strain has a DNA-DNA hybridization (DDH) value of equal to or greater than about 70% with *Eubacterium hallii* strain EHA01 (P168-Fla). In certain embodiments, the *Eubacterium hallii* strain is one having greater than about 70%, about 75%, about 80%, about 85%, about 90%, about 95%, about 98% or about 99% DNA-DNA hybridization with *Eubacterium hallii* strain EHA01 (P168-Fla). In certain embodiments, a contemplated *Eubacterium hallii* strain has equal to or greater than 95% average nucleotide identity (ANI) with *Eubacterium hallii* strain EHA01 (P168-Fla). In certain embodiments, the ANI is equal to or greater than about 95%, about 95.5%, about 96%, about 96.5%, about 97%, about 97.5%, about 98%, about 98.5%, about 99%, about 99.5%, or 100%. In certain embodiments, a contemplated *Eubacterium hallii* strain has equal to or greater than 60% alignment fraction (AF) with *Eubacterium hallii* strain EHA01 (P168-Fla). In certain embodiments, the AF is equal to or greater than about 65%, about 70%, about 75%, about 80%, about 85%, about 90%, about 95%, or 100%.

A contemplated bacterial strain, for example, for use in a disclosed bacterial strain mixture, pharmaceutical composition or unit, or method, includes a *Roseburia* species strain. Exemplary *Roseburia* species include *R. cecicola, R. faecis, R. hominis, R. intestinalis,* and *R. inulinivorans*. Those of skill in the art will recognize that the genus *Roseburia* may undergo taxonomical reorganization. Thus, it is intended that a contemplated *Roseburia* species include *Roseburia* species that have been renamed and/or reclassified, as well as those that may be later renamed and/or reclassified.

In certain embodiments, a contemplated *Roseburia* species strain is a *Roseburia hominis* strain. For example, a contemplated *Roseburia hominis* strain genome may comprise a 16s rRNA gene sequence having the nucleotide sequence of SEQ ID NO: 1, or a 16s rRNA gene sequence having at least about 70.0%, about 80.0%, about 90.0%, about 91.0%, about 92.0%, about 93.0%, about 94.0%, about 95.0%, about 96.0%, about 97.0%, about 98.0%, about 98.1%, about 98.2%, about 98.3%, about 98.4%, about 98.5%, about 98.6%, about 98.7%, about 98.8%, about 98.9%, about 99.0%, about 99.1%, about 99.2%, about 99.3%, about 99.4%, about 99.5%, about 99.6%, about 99.7%, about 99.8%, or about 99.9% identity to the nucleotide sequence of SEQ ID NO: 1. In some embodiments, the sequence identity referred to above is across at least about 70% of SEQ ID NO: 1. In other embodiments, the sequence identity referred to above is across at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% of SEQ ID NO: 1.

In some embodiments, a contemplated *Roseburia hominis* strain comprises a genomic sequence (e.g., a whole genome sequence, or fragments or contigs thereof) having a certain % identity to one or more of SEQ ID NOs: 4-32. A contemplated *Roseburia hominis* strain genome may comprise the nucleotide sequence of any one of SEQ ID NOs: 4-32, or a nucleotide sequence having at least about 65%, about 70%, about 75%, about 80%, about 85%, about 90%, about 91%, about 92%, about 93%, about 94%, about 95%, about 96%, about 97%, about 98%, or about 99% identity to the nucleotide sequence of any one of SEQ ID NOs: 4-32. A contemplated *Roseburia hominis* strain genome may comprise the nucleotide sequence of each of SEQ ID NOs: 4-32, or each of a nucleotide sequence having at least about 65%, about 70%, about 75%, about 80%, about 85%, about 90%, about 91%, about 92%, about 93%, about 94%, about 95%, about 96%, about 97%, about 98%, or about 99% identity to the nucleotide sequence of each of SEQ ID NOs: 4-32.

In some embodiments, a contemplated *Roseburia hominis* strain comprises a whole genomic sequence having at least about 70% identity across at least 70% of its genome to the sum of all genomic contigs represented by SEQ ID NOs: 4-32. In some embodiments, the whole genomic sequence has at least about 75%, 80%, 85%, 90%, 95% or greater than 95% identity to the sum of all genomic contigs represented by SEQ ID NOs: 4-32. In some embodiments, the sequence identity referred to above is across at least 75%, 80%, 85%, 90%, 95% or greater than 95% of the whole genomic sequence of the bacterial strain. In some embodiments, a contemplated *Roseburia hominis* strain comprises a whole genomic sequence comprising coding regions having at least about 70% identity across at least 70% of the total coding regions in its genome to the coding regions within the sum of all genomic contigs represented by SEQ ID NOs: 4-32. In some embodiments, the coding regions within the whole genomic sequence have at least about 75%, 80%, 85%, 90%, 95% or greater than 95% identity to the coding regions within the sum of all genomic contigs represented by SEQ ID NOs: 4-32. In some embodiments, the sequence identity referred to above is across at least 75%, 80%, 85%, 90%, 95% or greater than 95% of the coding regions within the whole genomic sequence of the bacterial strain.

In certain embodiments, a contemplated *Roseburia* species strain, e.g., a *Roseburia hominis* strain, increases, or is capable of increasing, production of at least one anti-inflammatory gene product in a cell, tissue, or subject. For example, a contemplated *Roseburia* species strain, e.g., a *Roseburia hominis* strain, increases production of IL-10 and/or CCL-18 in a human cell, e.g., a THP-1 macrophage or monocyte or a PBMC. For example, contacting a human cell, e.g., a THP-1 macrophage or PBMC, with the *Roseburia* species strain, e.g., a *Roseburia hominis* strain, may increase production of IL-10 and/or CCL-18 in the cell by at least about 10%, at least about 20%, at least about 30%, at least about 40%, at least about 50%, at least about 75%, at least about 100%, at least about 200%, at least about 300%, at least about 400%, at least about 500%, at least about 750%, at least about 1000%, from about 10% to about 20%, from about 10% to about 50%, from about 10% to about 100%, from about 10% to about 200%, from about 10% to about 500%, from about 10% to about 1000%, from about 20% to about 50%, from about 20% to about 100%, from about 20% to about 200%, from about 20% to about 500%, from about 20% to about 1000%, from about 50% to about 100%, from about 50% to about 200%, from about 50% to about 500%, from about 50% to about 1000%, from about 100% to about 200%, from about 100% to about 500%, from about 100% to about 1000%, from about 200% to about 500%, from about 200% to about 1000%, or from about 500% to about 1000%, relative to a cell (e.g., of the same cell type) that was not contacted with the strain. In some embodiments, the contacting of the human cell with the *Roseburia* species strain occurs in vitro, e.g., the human cell is incubated with the *Roseburia* species strain. In some embodiments, the contacting of the human cell with the *Roseburia* species strain occurs in vivo.

In certain embodiments, a contemplated *Roseburia* species strain, e.g., a *Roseburia hominis* strain, reduces or attenuates, or is capable of reducing or attenuating, production of at least one pro-inflammatory gene product in a cell, tissue, or subject. For example, a contemplated *Roseburia* species strain, e.g., a *Roseburia hominis* strain, reduces or attenuates production of IL-6, IL-12, IL-17 and/or TNF-α in a human cell, e.g., a THP-1 macrophage or monocyte or a PBMC. For example, contacting a human cell, e.g., a THP-1 macrophage or PBMC, with the *Roseburia* species strain, e.g., a *Roseburia hominis* strain, may reduce or attenuate production of IL-6, IL-12, IL-17 and/or TNF-α in the cell by at least about 10%, at least about 20%, at least about 30%, at least about 40%, at least about 50%, at least about 75%, from about 10% to about 20%, from about 10% to about 50%, from about 10% to about 100%, from about 20% to about 50%, from about 20% to about 100%, or from about 50% to about 100%, relative to a cell (e.g., of the same cell type) that was not contacted with the strain. In some embodiments, the contacting of the human cell with the *Roseburia* species strain occurs in vitro, e.g., the human cell is incubated with the *Roseburia* species strain. In some embodiments, the contacting of the human cell with the *Roseburia* species strain occurs in vivo.

In certain embodiments, a contemplated *Roseburia* species strain, e.g., a *Roseburia hominis* strain, reduces or prevents disruption to, or increases, or is capable of reducing or preventing disruption to, or increasing, barrier integrity of a mucosal epithelium. For example, a contemplated *Roseburia* species strain, e.g., a *Roseburia hominis* strain, reduces or prevents disruption to, or increases, barrier integrity of a HT29MTX-E12 cell monolayer, e.g., a HT29MTX-E12 cell monolayer treated with TNF-α. For example, incubation of a *Roseburia* species strain, e.g., a *Roseburia hominis* strain, with a HT29MTX-E12 cell monolayer, e.g., a HT29MTX-E12 cell monolayer treated with TNF-α, may reduce or prevent disruption to, or increase, barrier integrity, e.g., as measured by trans-epithelial electrical resistance (TEER), by at least about 10%, at least about 20%, at least about 30%, at least about 40%, at least about 50%, at least about 60%, at least about 70%, at least about 80%, at least about 90%, at least about 100%, from about 20% to about 100%, from about 40% to about 100%, from about 60% to about 100%, from about 80% to about 100%, from about 20% to about 80%, from about 40% to about 80%, from about 60% to about 80%, from about 20% to about 60%, from about 40% to about 60%, or from about 20% to about 40%, relative to a HT29MTX-E12 cell monolayer that was not incubated with the strain.

In certain embodiments, a contemplated *Roseburia* species strain, e.g., a *Roseburia hominis* strain, induces or increases, or is capable of inducing or increasing, autophagy in a cell, tissue, or subject. For example, a contemplated *Roseburia* species strain, e.g., a *Roseburia hominis* strain, induces or increases autophagy in a human cell, e.g., a THP-1 macrophage. For example, contacting a human cell, e.g., a THP-1 macrophage, with the *Roseburia* species strain, e.g., a *Roseburia hominis* strain, may induce or increase autophagy in the cell by at least about 10%, at least about 20%, at least about 30%, at least about 40%, at least about 50%, at least about 60%, at least about 70%, at least about 80%, at least about 90%, at least about 100%, from about 10% to about 20%, from about 10% to about 50%, from about 10% to about 100%, from about 20% to about 50%, from about 20% to about 100%, from about 20% to about 200%, from about 50% to about 100%, or from about 50% to about 200%, relative to a cell (e.g., of the same cell type) that was not contacted with the strain. In some embodiments, the contacting of the human cell with the *Roseburia* species strain occurs in vitro, e.g., the human cell is incubated with the *Roseburia* species strain. In some embodiments, the contacting of the human cell with the *Roseburia* species strain occurs in vivo.

In certain embodiments, a contemplated *Roseburia* species strain, e.g., a *Roseburia hominis* strain, reduces or attenuates, or is capable of reducing or attenuating, production of Lipocalin-2/NGAL in a cell, tissue, or subject. For example, contacting a human cell with a *Roseburia* species strain, e.g., a *Roseburia hominis* strain may reduce or attenuate production of Lipocalin-2/NGAL in the cell by at least about 10%, at least about 20%, at least about 30%, at least about 40%, at least about 50%, at least about 75%, from about 10% to about 20%, from about 10% to about 50%, from about 10% to about 100%, from about 20% to about 50%, from about 20% to about 100%, or from about 50% to about 100%, relative to a cell (e.g., of the same cell type) that was not contacted with the strain. In some embodiments, the contacting of the human cell with the *Roseburia* species strain occurs in vitro, e.g., the human cell is incubated with the *Roseburia* species strain. In some embodiments, the contacting of the human cell with the *Bacteroides* species strain occurs in vivo.

In certain embodiments, a contemplated *Roseburia hominis* strain is the strain identified herein as RHO01. A deposit of *Roseburia hominis* strain RHO01 (P127-H9a) was made to DSMZ (Deutsche Sammlung von Mikroorganismen and Zellkulturen GmbH, Inhoffenstraße 7B, 38124 Brunswick, Germany) under the Budapest Treaty on the International Recognition of the Deposit of Microorganisms for the Purposes of Patent Procedure on Sep. 14, 2018. This deposit was accorded accession number DSM-32921. The 16s rRNA gene sequence of *Roseburia hominis* strain RHO01 is provided herein as SEQ ID NO: 1, and genomic sequences of *Roseburia hominis* strain RHO01 are provided herein as SEQ ID NOs: 4-32.

In certain embodiments, a contemplated *Roseburia hominis* strain has a DNA-DNA hybridization (DDH) value of equal to or greater than about 70% with *Roseburia hominis* strain RHO01 (P127-H9a). In certain embodiments, the *Roseburia hominis* strain is one having greater than about 70%, about 75%, about 80%, about 85%, about 90%, about 95%, about 98% or about 99% DNA-DNA hybridization with *Roseburia hominis* strain RHO01 (P127-H9a). In certain embodiments, a contemplated *Roseburia hominis* strain has equal to or greater than 95% average nucleotide identity (ANI) with *Roseburia hominis* strain RHO01 (P127-H9a). In certain embodiments, the ANI is equal to or greater than about 95%, about 95.5%, about 96%, about 96.5%, about 97%, about 97.5%, about 98%, about 98.5%, about 99%, about 99.5%, or 100%. In certain embodiments, a contemplated *Roseburia hominis* strain has equal to or greater than 60% alignment fraction (AF) with *Roseburia hominis* strain RHO01 (P127-H9a). In certain embodiments, the AF is equal to or greater than about 65%, about 70%, about 75%, about 80%, about 85%, about 90%, about 95%, or 100%.

In some embodiments, a contemplated bacterial strain mixture may, e.g., include at least 2, e.g., 2 or 3, bacterial strains disclosed herein.

For example, a contemplated bacterial strain mixture may comprise: (i) a *Bacteroides* species strain, e.g., a *Bacteroides thetaiotaomicron* strain, e.g., the BTH01 strain; and (ii) a *Eubacterium* species strain, e.g., a *Eubacterium hallii* strain, e.g., the EHA01 strain. For example, in certain embodiments, a contemplated bacterial strain mixture comprises: (i) a *Bacteroides* species strain and a *Eubacterium* species strain; (ii) a *Bacteroides* species strain and a *Eubacterium hallii* strain; (iii) a *Bacteroides* species strain and the EHA01 strain; (iv) a *Bacteroides thetaiotaomicron* strain and a *Eubacterium* species strain; (v) a *Bacteroides thetaiotaomicron* strain and a *Eubacterium hallii* strain; (vi) a *Bacteroides thetaiotaomicron* strain and the EHA01 strain; (vii) the BTH01 strain and a *Eubacterium* species strain; (viii) the BTH01 strain and a *Eubacterium hallii* strain; or (ix) the BTH01 strain and the EHA01 strain. In certain embodiments, a contemplated bacterial strain mixture: (i) increases, or is capable of increasing, production of at least one anti-inflammatory gene product, e.g., IL-10 and/or CCL-18, in a human cell, e.g., a THP-1 macrophage or monocyte or a PBMC; (ii) reduces or attenuates, or is capable of reducing or attenuating, production of at least one pro-inflammatory gene product, e.g., IL-6, IL-12, IL-17 and/or TNF-α, in a human cell, e.g., a THP-1 macrophage or monocyte or a PBMC; (iii) reduces or prevents disruption of, or increases, or is capable of reducing or preventing disruption of, or increasing, barrier integrity of an epithelial cell monolayer, e.g., a HT29MTX-E12 cell monolayer treated with TNF-α; (iv) induces or increases, or is capable of inducing or increasing, autophagy in a human cell e.g., a THP-1 macrophage; and/or (v) reduces or attenuates, or is capable of reducing or attenuating, production of Lipocalin-2/NGAL in a cell, tissue or subject.

For example, a contemplated bacterial strain mixture may comprise: (i) a *Bacteroides* species strain, e.g., a *Bacteroides thetaiotaomicron* strain, e.g., the BTH01 strain; and (ii) a *Roseburia* species strain, e.g., a *Roseburia hominis* strain, e.g., the RHO01 strain. For example, in certain embodiments, a contemplated bacterial strain mixture comprises: (i) a *Bacteroides* species strain and a *Roseburia* species strain; (ii) a *Bacteroides* species strain and a *Roseburia hominis* strain; (iii) a *Bacteroides* species strain and the RHO01 strain; (iv) a *Bacteroides thetaiotaomicron* strain and a *Roseburia* species strain; (v) a *Bacteroides thetaiotaomicron* strain and a *Roseburia hominis* strain; (vi) a *Bacteroides thetaiotaomicron* strain and the RHO01 strain; (vii) the BTH01 strain and a *Roseburia* species strain; (viii) the BTH01 strain and a *Roseburia hominis* strain; or (ix) the BTH01 strain and the RHO01 strain. In certain embodiments, a contemplated bacterial strain mixture: (i) increases, or is capable of increasing, production of at least one anti-inflammatory gene product, e.g., IL-10 and/or CCL-18, in a human cell, e.g., a THP-1 macrophage or monocyte or a PBMC; (ii) reduces or attenuates, or is capable of reducing or attenuating, production of at least one pro-inflammatory gene product, e.g., IL-6, IL-12, IL-17 and/or TNF-α, in a human cell, e.g., a THP-1 macrophage or monocyte or a PBMC; (iii) reduces or prevents disruption of, or increases, or is capable of reducing or preventing disruption of, or increasing, barrier integrity of an epithelial cell monolayer, e.g., a HT29MTX-E12 cell monolayer treated with TNF-α; (iv) induces or increases, or is capable of inducing or increasing, autophagy in a human cell e.g., a THP-1 macrophage; and/or (v) reduces or attenuates, or is capable of reducing or attenuating, production of Lipocalin-2/NGAL in a cell, tissue or subject.

For example, a contemplated bacterial strain mixture may comprise: (i) a *Eubacterium* species strain, e.g., a *Eubacterium hallii* strain, e.g., the EHA01 strain; and (ii) a *Roseburia* species strain, e.g., a *Roseburia hominis* strain, e.g., the RHO01 strain. For example, in certain embodiments, a contemplated bacterial strain mixture comprises: (i) a *Eubacterium* species strain and a *Roseburia* species strain; (ii) a *Eubacterium* species strain and a *Roseburia hominis* strain; (iii) a *Eubacterium* species strain and the RHO01 strain; (iv) a *Eubacterium hallii* strain and a *Roseburia* species strain; (v) a *Eubacterium hallii* strain and a *Roseburia hominis* strain; (vi) a *Eubacterium hallii* strain and the RHO01 strain; (vii) the EHA01 strain and a *Roseburia* species strain; (viii) the EHA01 strain and a *Roseburia hominis* strain; or (ix) the EHA01 strain and the RHO01 strain. In certain embodiments, a contemplated bacterial strain mixture: (i) increases, or is capable of increasing, production of at least one anti-inflammatory gene product, e.g., IL-10 and/or CCL-18, in a human cell, e.g., a THP-1 macrophage or monocyte or a PBMC; (ii) reduces or attenuates, or is capable of reducing or attenuating, production of at least one pro-inflammatory gene product, e.g., IL-6, IL-12, IL-17 and/or TNF-α, in a human cell, e.g., a THP-1 macrophage or monocyte or a PBMC; (iii) reduces or prevents disruption of, or increases, or is capable of reducing or preventing disruption of, or increasing, barrier integrity of an epithelial cell monolayer, e.g., a HT29MTX-E12 cell monolayer treated with TNF-α; (iv) induces or increases, or is capable of inducing or increasing, autophagy in a human cell e.g., a THP-1 macrophage; and/or (v) reduces or attenuates, or is capable of reducing or attenuating, production of Lipocalin-2/NGAL in a cell, tissue or subject.

For example, a contemplated bacterial strain mixture may comprise: (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and (iii) a *Roseburia* species strain, e.g., a *Roseburia hominis* strain, e.g., the RHO01 strain. For example, in certain embodiments, a contemplated bacterial strain mixture comprises: (i) a *Bacteroides* species strain, a *Eubacterium* species strain, and a *Roseburia* species strain; (ii) a *Bacteroides* species strain, a *Eubacterium* species strain, and a *Roseburia hominis* strain; (iii) a *Bacteroides* species strain, a *Eubacterium* species strain, and the RHO01 strain; (iv) a *Bacteroides* species strain, a *Eubacterium hallii* strain, and a *Roseburia* species strain; (v) a *Bacteroides* species strain, a *Eubacterium hallii* strain, and a *Roseburia hominis* strain; (vi) a *Bacteroides* species strain, a *Eubacterium hallii* strain, and the RHO01 strain; (vii) a *Bacteroides* species strain, the EHA01 strain, and a *Roseburia* species strain; (viii) a *Bacteroides* species strain, the EHA01 strain, and a *Roseburia hominis* strain; (ix) a *Bacteroides* species strain, the EHA01 strain, and the RHO01 strain; (x) a *Bacteroides thetaiotaomicron* strain, a *Eubacterium* species strain, and a *Roseburia* species strain; (xi) a *Bacteroides thetaiotaomicron* strain, a *Eubacterium* species strain, and a *Roseburia hominis* strain; (xii) a *Bacteroides thetaiotaomicron* strain, a *Eubacterium* species strain, and the RHO01 strain; (xiii) a *Bacteroides thetaiotaomicron* strain, a *Eubacterium hallii* strain, and a *Roseburia* species strain; (xiv) a *Bacteroides thetaiotaomicron* strain, a *Eubacterium hallii* strain, and a *Roseburia hominis* strain; (xv) a *Bacteroides thetaiotaomicron* strain, a *Eubacterium hallii* strain, and the RHO01 strain; (xvi) a *Bacteroides thetaiotaomicron* strain, the EHA01 strain, and a *Roseburia* species strain; (xvii) a *Bacteroides thetaiotaomicron* strain, the EHA01 strain, and a *Roseburia hominis* strain; (xviii) a *Bacteroides thetaiotaomicron* strain, the EHA01 strain, and the RHO01 strain; (xix) the BTH01 strain, a *Eubacterium* species strain, and a *Roseburia* species strain; (xx) the BTH01 strain, a *Eubacterium* species strain, and a *Roseburia hominis* strain; (xxi) the BTH01 strain, a *Eubacterium* species strain, and the RHO01 strain; (xxii) the BTH01 strain, a *Eubacterium hallii* strain, and a *Roseburia* species strain; (xxiii) the BTH01 strain, a *Eubacterium hallii* strain, and a *Roseburia hominis* strain; (xxiv) the BTH01 strain, a *Eubacterium hallii* strain, and the RHO01 strain; (xxv) the BTH01 strain, the EHA01 strain, and a *Roseburia* species strain; (xxvi) the BTH01 strain, the EHA01 strain, and a *Roseburia hominis* strain; or (xxvii) the BTH01 strain, the EHA01 strain, and the RHO01 strain. In certain embodiments, a contemplated bacterial strain mixture: (i) increases, or is capable of increasing, production of at least one anti-inflammatory gene product, e.g., IL-10 and/or CCL-18, in a human cell, e.g., a THP-1 macrophage or monocyte or a PBMC; (ii) reduces or attenuates, or is capable of reducing or attenuating, production of at least one pro-inflammatory gene product, e.g., IL-6, IL-12, IL-17 and/or TNF-α, in a human cell, e.g., a THP-1 macrophage or monocyte or a PBMC; (iii) reduces or prevents disruption of, or increases, or is capable of reducing or preventing disruption of, or increasing, barrier integrity of an epithelial cell monolayer, e.g., a HT29MTX-E12 cell monolayer treated with TNF-α; (iv) induces or increases, or is capable of inducing or increasing, autophagy in a human cell e.g., a THP-1 macrophage; and/or (v) reduces or attenuates, or is capable of reducing or attenuating, production of Lipocalin-2/NGAL in a cell, tissue or subject.

For example, a contemplated bacterial strain mixture may consist essentially of: (i) a *Bacteroides* species strain, e.g., a *Bacteroides thetaiotaomicron* strain, e.g., the BTH01 strain; and (ii) a *Eubacterium* species strain, e.g., a *Eubacterium hallii* strain, e.g., the EHA01 strain. For example, in certain embodiments, a contemplated bacterial strain mixture consists essentially of: (i) a *Bacteroides* species strain and a *Eubacterium* species strain; (ii) a *Bacteroides* species strain and a *Eubacterium hallii* strain; (iii) a *Bacteroides* species strain and the EHA01 strain; (iv) a *Bacteroides thetaiotaomicron* strain and a *Eubacterium* species strain; (v) a *Bacteroides thetaiotaomicron* strain and a *Eubacterium hallii* strain; (vi) a *Bacteroides thetaiotaomicron* strain and the EHA01 strain; (vii) the BTH01 strain and a *Eubacterium* species strain; (viii) the BTH01 strain and a *Eubacterium hallii* strain; or (ix) the BTH01 strain and the EHA01 strain. In certain embodiments, a contemplated bacterial strain mixture: (i) increases, or is capable of increasing, production of at least one anti-inflammatory gene product, e.g., IL-10 and/or CCL-18, in a human cell, e.g., a THP-1 macrophage or monocyte or a PBMC; (ii) reduces or attenuates, or is capable of reducing or attenuating, production of at least one pro-inflammatory gene product, e.g., IL-6, IL-12, IL-17 and/or TNF-α, in a human cell, e.g., a THP-1 macrophage or monocyte or a PBMC; (iii) reduces or prevents disruption of, or increases, or is capable of reducing or preventing disruption of, or increasing, barrier integrity of an epithelial cell monolayer, e.g., a HT29MTX-E12 cell monolayer treated with TNF-α; (iv) induces or increases, or is capable of inducing or increasing, autophagy in a human cell e.g., a THP-1 macrophage; and/or (v) reduces or attenuates, or is capable of reducing or attenuating, production of Lipocalin-2/NGAL in a cell, tissue or subject.

For example, a contemplated bacterial strain mixture may consist essentially of: (i) a *Bacteroides* species strain, e.g., a *Bacteroides thetaiotaomicron* strain, e.g., the BTH01 strain; and (ii) a *Roseburia* species strain, e.g., a *Roseburia hominis* strain, e.g., the RHO01 strain. For example, in certain embodiments, a contemplated bacterial strain mixture consists essentially of: (i) a *Bacteroides* species strain and a *Roseburia* species strain; (ii) a *Bacteroides* species strain and a *Roseburia hominis* strain; (iii) a *Bacteroides* species strain and the RHO01 strain; (iv) a *Bacteroides thetaiotaomicron* strain and a *Roseburia* species strain; (v) a *Bacteroides thetaiotaomicron* strain and a *Roseburia hominis* strain; (vi) a *Bacteroides thetaiotaomicron* strain and the RHO01 strain; (vii) the BTH01 strain and a *Roseburia* species strain; (viii) the BTH01 strain and a *Roseburia hominis* strain; or (ix) the BTH01 strain and the RHO01 strain. In certain embodiments, a contemplated bacterial strain mixture: (i) increases, or is capable of increasing, production of at least one anti-inflammatory gene product, e.g., IL-10 and/or CCL-18, in a human cell, e.g., a THP-1 macrophage or monocyte or a PBMC; (ii) reduces or attenuates, or is capable of reducing or attenuating, production of at least one pro-inflammatory gene product, e.g., IL-6, IL-12, IL-17 and/or TNF-α, in a human cell, e.g., a THP-1 macrophage or monocyte or a PBMC; (iii) reduces or prevents disruption of, or increases, or is capable of reducing or preventing disruption of, or increasing, barrier integrity of an epithelial cell monolayer, e.g., a HT29MTX-E12 cell monolayer treated with TNF-α; (iv) induces or increases, or is capable of inducing or increasing, autophagy in a human cell e.g., a THP-1 macrophage; and/or (v) reduces or attenuates, or is capable of reducing or attenuating, production of Lipocalin-2/NGAL in a cell, tissue or subject.

For example, a contemplated bacterial strain mixture may consist essentially of: (i) a *Eubacterium* species strain, e.g., a *Eubacterium hallii* strain, e.g., the EHA01 strain; and (ii) a *Roseburia* species strain, e.g., a *Roseburia hominis* strain, e.g., the RHO01 strain. For example, in certain embodiments, a contemplated bacterial strain mixture consists essentially of: (i) a *Eubacterium* species strain and a *Roseburia* species strain; (ii) a *Eubacterium* species strain and a *Roseburia hominis* strain; (iii) a *Eubacterium* species strain and the RHO01 strain; (iv) a *Eubacterium hallii* strain and a *Roseburia* species strain; (v) a *Eubacterium hallii* strain and a *Roseburia hominis* strain; (vi) a *Eubacterium hallii* strain and the RHO01 strain; (vii) the EHA01 strain and a *Roseburia* species strain; (viii) the EHA01 strain and a *Roseburia hominis* strain; or (ix) the EHA01 strain and the RHO01 strain. In certain embodiments, a contemplated bacterial strain mixture: (i) increases, or is capable of increasing, production of at least one anti-inflammatory gene product, e.g., IL-10 and/or CCL-18, in a human cell, e.g., a THP-1 macrophage or monocyte or a PBMC; (ii) reduces or attenuates, or is capable of reducing or attenuating, production of at least one pro-inflammatory gene product, e.g., IL-6, IL-12, IL-17 and/or TNF-α, in a human cell, e.g., a THP-1 macrophage or monocyte or a PBMC; (iii) reduces or prevents disruption of, or increases, or is capable of reducing or preventing disruption of, or increasing, barrier integrity of an epithelial cell monolayer, e.g., a HT29MTX-E12 cell monolayer treated with TNF-α; (iv) induces or increases, or is capable of inducing or increasing, autophagy in a human cell e.g., a THP-1 macrophage; and/or (v) reduces or attenuates, or is capable of reducing or attenuating, production of Lipocalin-2/NGAL in a cell, tissue or subject.

For example, a contemplated bacterial strain mixture may consist essentially of: (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and (iii) a *Roseburia* species strain, e.g., a *Roseburia hominis* strain, e.g., the RHO01 strain. For example, in certain embodiments, a contemplated bacterial strain mixture consists essentially of: (i) a *Bacteroides* species strain, a *Eubacterium* species strain, and a *Roseburia* species strain; (ii) a *Bacteroides* species strain, a *Eubacterium* species strain, and a *Roseburia hominis* strain; (iii) a *Bacteroides* species strain, a *Eubacterium* species strain, and the RHO01 strain; (iv) a *Bacteroides* species strain, a *Eubacterium hallii* strain, and a *Roseburia* species strain; (v) a *Bacteroides* species strain, a *Eubacterium hallii* strain, and a *Roseburia hominis* strain; (vi) a *Bacteroides* species strain, a *Eubacterium hallii* strain, and the RHO01 strain; (vii) a *Bacteroides* species strain, the EHA01 strain, and a *Roseburia* species strain; (viii) a *Bacteroides* species strain, the EHA01 strain, and a *Roseburia hominis* strain; (ix) a *Bacteroides* species strain, the EHA01 strain, and the RHO01 strain; (x) a *Bacteroides thetaiotaomicron* strain, a *Eubacterium* species strain, and a *Roseburia* species strain; (xi) a *Bacteroides thetaiotaomicron* strain, a *Eubacterium* species strain, and a *Roseburia hominis* strain; (xii) a *Bacteroides thetaiotaomicron* strain, a *Eubacterium* species strain, and the RHO01 strain; (xiii) a *Bacteroides thetaiotaomicron* strain, a *Eubacterium hallii* strain, and a *Roseburia* species strain; (xiv) a *Bacteroides thetaiotaomicron* strain, a *Eubacterium hallii* strain, and a *Roseburia hominis* strain; (xv) a *Bacteroides thetaiotaomicron* strain, a *Eubacterium hallii* strain, and the RHO01 strain; (xvi) a *Bacteroides thetaiotao-*

*micron* strain, the EHA01 strain, and a *Roseburia* species strain; (xvii) a *Bacteroides thetaiotaomicron* strain, the EHA01 strain, and a *Roseburia hominis* strain; (xviii) a *Bacteroides thetaiotaomicron* strain, the EHA01 strain, and the RHO01 strain; (xix) the BTH01 strain, a *Eubacterium* species strain, and a *Roseburia* species strain; (xx) the BTH01 strain, a *Eubacterium* species strain, and a *Roseburia hominis* strain; (xxi) the BTH01 strain, a *Eubacterium* species strain, and the RHO01 strain; (xxii) the BTH01 strain, a *Eubacterium hallii* strain, and a *Roseburia* species strain; (xxiii) the BTH01 strain, a *Eubacterium hallii* strain, and a *Roseburia hominis* strain; (xxiv) the BTH01 strain, a *Eubacterium hallii* strain, and the RHO01 strain; (xxv) the BTH01 strain, the EHA01 strain, and a *Roseburia* species strain; (xxvi) the BTH01 strain, the EHA01 strain, and a *Roseburia hominis* strain; or (xxvii) the BTH01 strain, the EHA01 strain, and the RHO01 strain. In certain embodiments, a contemplated bacterial strain mixture: (i) increases, or is capable of increasing, production of at least one anti-inflammatory gene product, e.g., IL-10 and/or CCL-18, in a human cell, e.g., a THP-1 macrophage or monocyte or a PBMC; (ii) reduces or attenuates, or is capable of reducing or attenuating, production of at least one pro-inflammatory gene product, e.g., IL-6, IL-12, IL-17 and/or TNF-α, in a human cell, e.g., a THP-1 macrophage or monocyte or a PBMC; (iii) reduces or prevents disruption of, or increases, or is capable of reducing or preventing disruption of, or increasing, barrier integrity of an epithelial cell monolayer, e.g., a HT29MTX-E12 cell monolayer treated with TNF-α; (iv) induces or increases, or is capable of inducing or increasing, autophagy in a human cell e.g., a THP-1 macrophage; and/or (v) reduces or attenuates, or is capable of reducing or attenuating, production of Lipocalin-2/NGAL in a cell, tissue or subject.

A contemplated bacterial strain mixture may, e.g., comprise or consist essentially of 2, 3, 4, 5, 6, 7, 8, 9, 10, or more than 10 bacterial strains. In some embodiments, one or more strains of the bacterial strain mixture are vegetative. In some embodiments, all the strains of the bacterial strain mixture are vegetative. For example, in certain embodiments, a disclosed bacterial strain mixture comprises or consists essentially of 2 to 10, 2 to 9, 2 to 8, 2 to 7, 2 to 6, 2 to 5, 2 to 4, or 2 to 3 bacterial strains; or, for example, may comprise or consist essentially of 3 to 10, 3 to 9, 3 to 8, 3 to 7, 3 to 6, 3 to 5 or 3 to 4 bacterial strains; or, for example, may comprise or consist essentially of 4 to 10, 4 to 9, 4 to 8, 4 to 7, 4 to 6 or 4 to 5 bacterial strains; or, for example, may comprise or consist essentially of 5 to 10, 5 to 9, 5 to 8, 5 to 7, 5 to 6, 6 to 10, 6 to 9, 6 to 8, 6 to 7, 7 to 10, 7 to 9, or 7 to 8 bacterial strains; or, for example, may comprise or consist essentially of 8 to 10 or 8 to 9 bacterial strains. In some embodiments, a disclosed bacterial strain mixture comprises or consists essentially of 2 or 3 bacterial strains. In some of the above embodiments, the bacterial strain mixture comprises at least two bacterial strains each selected from the group consisting of: a *Bacteroides* species strain (e.g., a *Bacteroides thetaiotaomicron* strain), a *Eubacterium* species (e.g., a *Eubacterium hallii* strain), and a *Roseburia* species (e.g., a *Roseburia hominis* strain); and further comprises or consists essentially of an additional 1, 2, 3, 4, 5, 6, 7, 8, 9, 10, or more than 10 bacterial strains. In some embodiments, the additional bacterial strains include a *Bacteroides* species strain, a *Eubacterium* species strain, and/or a *Roseburia* species strain, and/or strains other than a *Bacteroides* species strain, a *Eubacterium* species strain, and/or a *Roseburia* species strain. In some embodiments, the additional bacterial strains are selected based on their ability to independently: (i) increase production of at least one anti-inflammatory gene product, e.g., IL-10 and/or CCL-18, in a human cell, e.g., a THP-1 macrophage or monocyte or a PBMC; (ii) reduce or attenuate production of at least one pro-inflammatory gene product, e.g., IL-6, IL-12, IL-17 and/or TNF-α, in a human cell, e.g., a THP-1 macrophage or monocyte or a PBMC; (iii) reduce or prevent disruption of, or increase, barrier integrity of an epithelial cell monolayer, e.g., a HT29MTX-E12 cell monolayer treated with TNF-α; (iv) induce or increase autophagy in a human cell e.g., a THP-1 macrophage; and/or (v) reduces or attenuates, or is capable of reducing or attenuating, production of Lipocalin-2/NGAL in a cell, tissue or subject.

In some embodiments, a contemplated bacterial strain mixture increases, or is capable of increasing, production of at least one anti-inflammatory gene product in a cell, tissue, or subject. For example, a contemplated bacterial strain mixture, e.g., increases production of IL-10 and/or CCL-18 in a human cell, e.g., a THP-1 macrophage or monocyte or a PBMC. For example, contacting a human cell, e.g., a THP-1 macrophage or a PBMC, with the bacterial strain mixture may increase production of IL-10 and/or CCL-18 in the cell by at least about 10%, at least about 20%, at least about 30%, at least about 40%, at least about 50%, at least about 75%, at least about 100%, at least about 200%, at least about 300%, at least about 400%, at least about 500%, at least about 750%, at least about 1000%, from about 10% to about 20%, from about 10% to about 50%, from about 10% to about 100%, from about 10% to about 200%, from about 10% to about 500%, from about 10% to about 1000%, from about 20% to about 50%, from about 20% to about 100%, from about 20% to about 200%, from about 20% to about 500%, from about 20% to about 1000%, from about 50% to about 100%, from about 50% to about 200%, from about 50% to about 500%, from about 50% to about 1000%, from about 100% to about 200%, from about 100% to about 500%, from about 100% to about 1000%, from about 200% to about 500%, from about 200% to about 1000%, or from about 500% to about 1000%, relative to a cell (e.g., of the same cell type) that was not contacted with the bacterial strain mixture. In some embodiments, the contacting of the human cell with the bacterial strain mixture occurs in vitro, e.g., the human cell is incubated with the bacterial strain mixture. In some embodiments, the contacting of the human cell with the bacterial strain mixture occurs in vivo. In some embodiments, the bacterial strains of the bacterial strain mixture increase, or are capable of increasing, production of the at least one anti-inflammatory gene product in a synergistic manner. For example, the production of the at least one anti-inflammatory gene product induced by the bacterial strain mixture is greater than the production induced by each bacterial strain in the mixture individually, and/or the production induced by each individual bacterial strain added together. In some embodiments, the production of the at least one anti-inflammatory gene product induced by the bacterial strain mixture is at least 5%, 10%, 15%, 20%, 25%, 30%, 35%, 40%, 45%, 50%, 60%, 65%, 70%, 75%, 80%, 85%, 90%, 95%, 100%, or more than 100% greater than the production induced by each bacterial strain in the mixture individually, and/or the production induced by each individual bacterial strain added together.

In some embodiments, a contemplated bacterial strain mixture reduces or attenuates, or is capable of reducing or attenuating, production of at least one pro-inflammatory gene product in a cell, tissue, or subject. For example, a contemplated bacterial strain mixture reduces or attenuates production of IL-6, IL-12, IL-17 and/or TNF-α in a human cell, e.g., a THP-1 macrophage or monocyte or a PBMC. For example, contacting a human cell, e.g., a THP-1 macrophage or a PBMC, with the bacterial strain mixture may reduce or attenuate production of IL-6, IL-12, IL-17 and/or TNF-α in the cell by at least about 10%, at least about 20%, at least about 30%, at least about 40%, at least about 50%, at least about 75%, from about 10% to about 20%, from about 10% to about 50%, from about 10% to about 100%, from about 20% to about 50%, from about 20% to about 100%, or from about 50% to about 100%, relative to a cell (e.g., of the same cell type) that was not contacted with the bacterial strain mixture. In some embodiments, the contacting of the human cell with the bacterial strain mixture occurs in vitro, e.g., the human cell is incubated with the bacterial strain mixture. In some embodiments, the contacting of the human cell with the bacterial strain mixture occurs in vivo. In some embodiments, the bacterial strains of the bacterial strain mixture reduce or attenuate production of the at least one pro-inflammatory gene product in a synergistic manner. For example, the reduction or attenuation of production of the at least one pro-inflammatory gene product induced by the bacterial strain mixture is greater than that induced by each bacterial strain in the mixture individually, and/or the attenuation or reduction induced by each individual bacterial strain added together. In some embodiments, the reduction or attenuation of production of the at least one pro-inflammatory gene product induced by the bacterial strain mixture is at least 5%, 10%, 15%, 20%, 25%, 30%, 35%, 40%, 45%, 50%, 60%, 65%, 70%, 75%, 80%, 85%, 90%, 95%, 100%, or more than 100% greater than the reduction or attenuation of production induced by each bacterial strain in the mixture individually, and/or the attenuation or reduction induced by each individual bacterial strain added together.

In some embodiments, a contemplated bacterial strain mixture reduces or prevents disruption, or increases, or is capable of reducing or preventing disruption, or increasing, barrier integrity of a mucosal epithelium. For example, a contemplated bacterial strain mixture reduces or prevents disruption of, or increases, barrier integrity of a HT29MTX-E12 cell monolayer, e.g., a HT29MTX-E12 cell monolayer treated with TNF-α. For example, incubation of a contemplated bacterial strain mixture with a HT29MTX-E12 cell monolayer, e.g., a HT29MTX-E12 cell monolayer treated with TNF-α, may reduce or prevent disruption of, or increase, barrier integrity, e.g., as measured by trans-epithelial electrical resistance (TEER), by at least about 10%, at least about 20%, at least about 30%, at least about 40%, at least about 50%, at least about 60%, at least about 70%, at least about 80%, at least about 90%, at least about 100%, from about 20% to about 100%, from about 40% to about 100%, from about 60% to about 100%, from about 80% to about 100%, from about 20% to about 80%, from about 40% to about 80%, from about 60% to about 80%, from about 20% to about 60%, from about 40% to about 60%, or from about 20% to about 40%, relative to a HT29MTX-E12 cell monolayer that was not incubated with the bacterial strain mixture.

In some embodiments, a contemplated bacterial strain mixture induces or increases, or is capable of inducing or increasing, autophagy in a cell, tissue, or subject. For example, a contemplated bacterial strain mixture induces or increases autophagy in a human cell, e.g., a THP-1 macrophage. For example, contacting a human cell, e.g., a THP-1 macrophage, with the bacterial strain mixture may induce or increase autophagy in the cell by at least about 10%, at least about 20%, at least about 30%, at least about 40%, at least about 50%, at least about 60%, at least about 70%, at least about 80%, at least about 90%, at least about 100%, from about 10% to about 20%, from about 10% to about 50%, from about 10% to about 100%, from about 20% to about 50%, from about 20% to about 100%, from about 20% to about 200%, from about 50% to about 100%, or from about 50% to about 200%, relative to a cell (e.g., of the same cell type) that was not contacted with the bacterial strain mixture. In some embodiments, the contacting of the human cell with the bacterial strain mixture occurs in vitro, e.g., the human cell is incubated with the bacterial strain mixture. In some embodiments, the contacting of the human cell with the bacterial strain mixture occurs in vivo. In some embodiments, the bacterial strains of the bacterial strain mixture increase autophagy in a synergistic manner. For example, the autophagy induced by the bacterial strain mixture is greater than the autophagy induced by each bacterial strain in the mixture individually, and/or the autophagy induced by each individual bacterial strain added together. In some embodiments, the autophagy induced by the bacterial strain mixture is at least 5%, 10%, 15%, 20%, 25%, 30%, 35%, 40%, 45%, 50%, 60%, 65%, 70%, 75%, 80%, 85%, 90%, 95%, 100%, or more than 100% greater than the autophagy induced by each bacterial strain in the mixture individually, and/or the autophagy induced by each individual bacterial strain added together.

In some embodiments, a contemplated bacterial strain mixture reduces or attenuates, or is capable of reducing or attenuating, production of Lipocalin-2/NGAL in a cell, tissue, or subject. For example, contacting a human cell with bacterial strain mixture may reduce or attenuate production of Lipocalin-2/NGAL in the cell by at least about 10%, at least about 20%, at least about 30%, at least about 40%, at least about 50%, at least about 75%, from about 10% to about 20%, from about 10% to about 50%, from about 10% to about 100%, from about 20% to about 50%, from about 20% to about 100%, or from about 50% to about 100%, relative to a cell (e.g., of the same cell type) that was not contacted with the bacterial strain mixture. In some embodiments, the contacting of the human cell with the bacterial strain mixture occurs in vitro, e.g., the human cell is incubated with the bacterial strain mixture strain. In some embodiments, the contacting of the human cell with the bacterial strain mixture occurs in vivo.

II. Pharmaceutical Compositions/Units

A bacteria disclosed herein may be combined with pharmaceutically acceptable excipients to form a pharmaceutical composition, which can be administered to a patient by any means known in the art. As used herein, the term "pharmaceutically acceptable excipient" is understood to mean one or more of a buffer, carrier, or excipient suitable for administration to a subject, for example, a human subject, without excessive toxicity, irritation, allergic response, or other problem or complication, commensurate with a reasonable benefit/risk ratio. The excipient(s) should be "acceptable" in the sense of being compatible with the other ingredients of the formulations and not deleterious to the recipient.

Pharmaceutically acceptable excipients include buffers, solvents, dispersion media, coatings, isotonic and absorption delaying agents, and the like, that are compatible with pharmaceutical administration. Pharmaceutically acceptable excipients also include fillers, binders, disintegrants, glidants, lubricants, and any combination(s) thereof. For example, a contemplated composition may comprise a pharmaceutical excipient selected from the group consisting of cellulose, polyvinyl pyrrolidone, silicon dioxide, stearyl fumarate or a pharmaceutically acceptable salt thereof, lactose, starch, glucose, methyl cellulose, ethyl cellulose, hydroxypropyl methyl cellulose, magnesium stearate, mannitol, sorbitol, and any combination(s) thereof. For further examples of excipients, carriers, stabilizers and adjuvants, see, e.g., Handbook of Pharmaceutical Excipients, $8^{th}$ Ed., Edited by P. J. Sheskey, W. G. Cook, and C.G. Cable, Pharmaceutical Press, London, UK [2017]. The use of such media and agents for pharmaceutically active substances is known in the art.

In certain embodiments, bacterial strains described herein may be used in any composition in stabilized form, including, for example, in a lyophilized state (with optionally one or more appropriate cryoprotectants), frozen (e.g., in a standard or super-cooled freezer), spray dried, and/or freeze dried. Stabilized bacteria (e.g., via lyophilization, freezing, spray drying or freeze drying), and in particular, stabilized anaerobic bacteria, may, in certain embodiments, possess advantageous properties over bacteria in culture with respect to administration, e.g., administration of a pharmaceutical composition provided herein. For example, lyophilizing bacteria involves a freeze-drying process that removes water from the bacterial cells. The resulting lyophilized bacteria may, in certain embodiments, have enhanced stability as compared to bacterial cultures, and thus may be stored for longer periods of time (i.e. extending shelf-life). In addition, in certain embodiments, in stabilized form, dehydrated bacterial cells do not grow or reproduce, but remain viable and may grow and reproduce when rehydrated. In certain embodiments, viability of stabilized anaerobic bacteria is maintained even when exposed to oxygen, thus facilitating their formulation (for example, into oral dosage forms) and use as a live biotherapeutic product that retains biological activity. Thus, in particular embodiments, the bacterial strains described herein are stabilized (e.g., via lyophilization, freezing, freeze-drying or spray-drying), live and viable, and retain some, most, or all of their chemical stability, and/or biological activity upon storage. Stability can be measured at a selected temperature and humidity conditions for a selected time period. Trend analysis can be used to estimate an expected shelf life before a material has actually been in storage for that time period. For live bacteria, for example, stability may be measured as the time it takes to lose 0.5 or 1 log of cfu/g dry formulation under predefined conditions of temperature and/or humidity. Alternatively, stability may be defined in terms of biological function as the time required to measure a decrease in a particular biological function per unit of dry formulation.

In certain embodiments, a contemplated pharmaceutical composition or pharmaceutical unit loses at most 0.5 log cfus, 1 log cfus, 1.5 log cfus, 2 log cfus, 2.5 log cfus, 3 log cfus, 3.5 log cfus, 4 log cfus, 4.5 log cfus, 5 log cfus, 5.5 log cfus, 6 log cfus, 6.5 log cfus, 7 log cfus, 7.5 log cfus, 8 log cfus, 8.5 log cfus, 9 log cfus, 9,5 log cfus, or 10 log cfus (total, or per gram of dry formulation) of each bacterial strain present in the pharmaceutical composition or unit upon storage for 1 month, 2 months, 3 months, 4 months, 5 months, 6 months, 7 months, 8 months, 9 months, 10 months 11, months, 12 months, 1 year, 1.5 years, 2 years, 2.5 years, 3 years, 3.5 years, 4 years, 4.5 years, or 5 years at 4° C. or −20° C. For example, a contemplated pharmaceutical composition or pharmaceutical unit may lose at most 3 log cfus of each bacterial strain present in the pharmaceutical composition or unit upon storage for 6 months, 1 year, or 2 years at 4° C.

A bacteria disclosed herein may be combined with one or more cryoprotectants. Exemplary cryoprotectants include fructoligosaccharides (e.g., raftilose®), trehalose, maltodextrin, sodium alginate, proline, glutamic acid, glycine (e.g., glycine betaine), mono-, di-, or polysaccharides (such as glucose, sucrose, maltose, lactose), polyols (such as mannitol, sorbitol, or glycerol), dextran, DMSO, methylcellulose, propylene glycol, polyvinylpyrrolidone, non-ionic surfactants such as TWEEN 80 Tween 80, and/or any combinations thereof.

In certain embodiments, a contemplated cryoprotectant comprises raftilose®, maltodextrin, alignate, trehalose, and sucrose, or any combinations thereof. An exemplary contemplated pharmaceutical composition includes sucrose as a cryoprotectant, and includes one or more strains selected from (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain. An exemplary contemplated pharmaceutical composition includes raftilose®, maltodextrin, alignate, trehalose, and sucrose as cryoprotectants, and includes one or more strains selected from (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain. An exemplary contemplated pharmaceutical composition includes raftilose®, maltodextrin, alignate, and trehalose as cryoprotectants, and includes one or more strains selected from (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain.

For example, a lyophilized powder form of a bacterial strain, as contemplated herein, may include about 10% to about 80% (by weight) of one or more bacterial strains (e.g., one bacterial strain) and about 20% to about 90% (by weight) of cryoprotectant and/or excipients, such as cryoprotectant and/or excipient selected from the group consisting of raftilose®, maltodextrin, sodium alginate, trehalose, sucrose, water, and/or combinations thereof. For example, 5 mg of contemplated lyophilized powder form of a bacterial strain may include about 0.5 mg to about 1.5 mg of the bacterial strain, about 1.5 mg to about 2.5 mg of the bacterial strain, about 2.5 to about 3.5 mg of the bacterial strain, or about 3.5 mg to about 4.5 mg of the bacterial strain. It can be appreciated that each lyophilized powder form of bacterial strain that may form a component of a disclosed composition may each have different excipients and/or amounts of excipients, as well as a discrete bacterial strain.

A pharmaceutical composition should be formulated to be compatible with its intended route of administration. Contemplated bacterial compositions disclosed herein can be prepared by any suitable method and can be formulated into a variety of forms and administered by a number of different means. Contemplated compositions can be administered orally, rectally, or enterally, in formulations containing conventionally acceptable carriers, adjuvants, and vehicles as desired. As used herein, "rectal administration" is understood to include administration by enema, suppository, or colonoscopy. A disclosed pharmaceutical composition may, e.g., be suitable for bolus administration or bolus release. In an exemplary embodiment, a disclosed bacterial composition is administered orally.

Solid dosage forms for oral administration include capsules, tablets, caplets, pills, troches, lozenges, powders, and granules. A capsule typically comprises a core material comprising a bacterial composition and a shell wall that encapsulates the core material. In some embodiments the core material comprises at least one of a solid, a liquid, and an emulsion. In some embodiments the shell wall material comprises at least one of a soft gelatin, a hard gelatin, and a polymer. Suitable polymers include, but are not limited to: cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit®"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In some embodiments at least one polymer functions as a taste-masking agent.

Tablets, pills, and the like can be compressed, multiply compressed, multiply layered, and/or coated. A contemplated coating can be single or multiple. In one embodiment, a contemplated coating material comprises at least one of a saccharide, a polysaccharide, and glycoproteins extracted from at least one of a plant, a fungus, and a microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In some embodiments a contemplated coating material comprises a protein. In some embodiments a contemplated coating material comprises at least one of a fat and an oil. In some embodiments the at least one of a fat and an oil is high temperature melting. In some embodiments the at least one of a fat and an oil is hydrogenated or partially hydrogenated. In some embodiments the at least one of a fat and an oil is derived from a plant. In some embodiments the at least one of a fat and an oil comprises at least one of glycerides, free fatty acids, and fatty acid esters. In some embodiments a contemplated coating material comprises at least one edible wax. A contemplated edible wax can be derived from animals, insects, or plants. Non-limiting examples include beeswax, lanolin, bayberry wax, carnauba wax, and rice bran wax. Tablets and pills can additionally be prepared with enteric or reverse-enteric coatings.

Alternatively, powders or granules embodying a bacterial composition disclosed herein can be incorporated into a food product. In some embodiments a contemplated food product is a drink for oral administration. Non-limiting examples of a suitable drink include water, fruit juice, a fruit drink, an artificially flavored drink, an artificially sweetened drink, a carbonated beverage, a sports drink, a liquid diary product, a shake, an alcoholic beverage, a caffeinated beverage, infant formula and so forth. Other suitable means for oral administration include aqueous and nonaqueous solutions, emulsions, suspensions and solutions and/or suspensions reconstituted from non-effervescent granules, containing at least one of suitable solvents, preservatives, emulsifying agents, suspending agents, diluents, sweeteners, coloring agents, and flavoring agents.

In certain embodiments, a contemplated pharmaceutical composition includes: (a) a mixture of lyophilized bacterial strains (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain; and (b) a filler (e.g., microcrystalline cellulose, lactose, sucrose, mannitol, or dicalcium phosphate dihydrate), a disintegrant (e.g., polyvinyl pyrrolidone, sodium starch glycolate, starch, or carboxymethyl-cellulose), a flow-aid/glidant (e.g., talc or silica derivatives (e.g., colloidal silica such as Cab-O-Sil® or Acrosil®)), and a lubricant (e.g., sodium stearyl fumarate, magnesium stearate, calcium stearate, stearic acid, stearic acid salt, talc, liquid paraffin, propylene glycol (PG), PEG 6000, or magnesium/sodium lauryl sulfate).

In certain embodiments, a contemplated pharmaceutical composition includes: (a) a mixture of lyophilized bacterial strains (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain; and (b) a filler (microcrystalline cellulose), a disintegrant (polyvinyl pyrrolidone), a flow-aid/glidant (silicon dioxide), and a lubricant (sodium stearyl fumarate).

In certain embodiments, a contemplated pharmaceutical composition is formulated as a capsule. In certain embodiments, the capsule is a hydroxypropyl methylcellulose (HPMC) capsule. In certain embodiments, the capsule includes a banding polymer (e.g., hydroxypropyl methylcellulose (HPMC)), and a banding solvent (e.g., water or ethanol). In certain embodiments, the capsule includes two banding solvents, water and ethanol. In certain embodiments the capsule is coated with a reverse enteric coating polymer (e.g., amino methacrylate copolymer), and comprises a surfactant (e.g., sodium lauryl sulfate), a flow-aid/glidant (e.g., silicon dioxide), a lubricant (e.g., stearic acid), an anti-tacking agent (e.g., talc), and a coating solvent (e.g., water). In certain embodiments the capsule is coated with an enteric coating polymer (e.g., poly(methacrylic acid-co-methyl methacrylate)), and further includes a plasticizer (e.g., triethyl citrate), an anti-tacking agent (e.g., talc), a pH adjuster (e.g., ammonia solution), and a coating solvent (e.g., purified water and isopropyl alcohol).

In certain embodiments, a contemplated capsule is a capsule-in-capsule dosage form, which includes an inner capsule and an outer capsule. In certain embodiments, the inner capsule includes a mixture of lyophilized bacterial strains (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain, a filler (e.g., microcrystalline cellulose, lactose, sucrose, mannitol, dicalcium phosphate dihydrate, or starch), a disintegrant (e.g., polyvinyl pyrrolidone, sodium starch glycolate, or carboxymethyl-cellulose), a flow-aid/glidant (e.g., silicon dioxide, talc, or colloidal silica), and a lubricant (e.g., sodium stearyl fumarate, magnesium stearate, calcium stearate, stearic acid, stearic acid salt, talc, liquid paraffin, propylene glycol (PG), PEG 6000, or magnesium/sodium lauryl sulfate). In certain embodiments, the outer capsule includes a mixture of lyophilized bacterial strains (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain, a filler (e.g., microcrystalline cellulose, lactose, sucrose, mannitol, dicalcium phosphate dihydrate, or starch), a disintegrant (e.g., polyvinyl pyrrolidone, sodium starch glycolate, or carboxymethylcellulose), a flow-aid/glidant (e.g., silicon dioxide, talc, or colloidal silica), and a lubricant (e.g., sodium stearyl fumarate, magnesium stearate, calcium stearate, stearic acid, stearic acid salt, talc liquid paraffin, propylene glycol (PG), PEG 6000, or magnesium/sodium lauryl sulfate).

In certain embodiments, a contemplated capsule is a capsule-in-capsule dosage form, which includes an inner capsule and an outer capsule. In certain embodiments, the inner capsule includes a mixture of lyophilized bacterial strains (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain, a filler (microcrystalline cellulose), a disintegrant (polyvinyl pyrrolidone), a flow-aid/glidant (silicon dioxide), and a lubricant (sodium stearyl fumarate). In certain embodiments, the outer capsule includes a mixture of lyophilized bacterial strains (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain, a filler (microcrystalline cellulose), a disintegrant (polyvinyl pyrrolidone), a flow-aid/glidant (silicon dioxide), and a lubricant (sodium stearyl fumarate).

In certain embodiments, a disclosed pharmaceutical unit comprises a dual component capsule. For example, a dual component capsule may comprise an inner capsule, wherein the inner capsule has a reverse enteric polymeric coating, and an outer capsule encapsulating the inner capsule, wherein the outer capsule has an enteric polymeric coating. A contemplated inner and/or outer capsule may comprise a bacterial strain or a bacterial strain mixture. For example, a dual component capsule may comprise an inner capsule having an inner composition comprising a bacterial strain or bacterial strain mixture and one or more pharmaceutical excipients, wherein the inner capsule has a reverse enteric polymeric coating, and an outer capsule encapsulating the inner capsule and an outer composition comprising a bacterial strain or bacterial strain mixture and one or more pharmaceutical excipients, wherein the outer capsule has an enteric polymeric coating. A contemplated inner and/or outer composition may, e.g., comprise: (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain. The inner composition and the outer composition may be the same or different.

A contemplated dual component capsule may include a total of about 5 mg to about 60 mg of the inner and outer composition, e.g., a total of about 5 mg to about 50 mg of the inner and outer composition, a total of about 5 mg to about 15 mg of the inner and outer composition, a total of about 5 mg to about 25 mg of the inner and outer composition, or a total of about 25 mg to about 50 mg of the inner and outer composition. A contemplated dual component capsule may include a total of about 50 mg to about 120 mg of the inner and outer composition, e.g., a total of about 50 mg to about 75 mg of the inner and outer composition, a total of about 60 mg to about 85 mg of the inner and outer composition, a total of about 50 mg to about 95 mg of the inner and outer composition, or a total of about 25 mg to about 110 mg of the inner and outer composition.

In certain embodiments, a disclosed dual component capsule includes an inner capsule with a reverse enteric polymeric coating, and an outer capsule with an enteric polymeric coating. Each respective coating, for example, allows for biphasic release of the capsule's contents (including bacterial strains) at distinct sites along the gastrointestinal tract. For example, it has been determined that the GI tract has several regions sharply demarcated by local pH ranging from 1 to 8.2. The normal pH profile of the GI tract rises and falls between the stomach and the colon with pH ranges of 1-4 in the stomach, 5.5-6.4 in the duodenum, 6.8-8.2 in the ileum, and 5.5-6.5 in the colon. For example, while the distal ileum contains a region where the usual pH is between 6.8 and 8.2, the pH drops sharply from 8.2 to 5.5 after passage through the ileocecal valve into the cecum and ascending colon. The pH gradually rises once again to 8.0 in the progression from proximal to distal colon. Accordingly, in certain embodiments, the enteric polymeric coating of the outer capsule solubilizes in a pH of about 7 to 8, allowing for release in the ileum, and the reverse enteric polymeric coating of the inner capsule solubilizes in a pH of about 6.2 to 6.5, allowing for subsequent release in the colon. In certain embodiments, the outer capsule maintains integrity (e.g., absence of splits, cracks, or rupture of capsule shell) for about 2 hours at pH 1.2 and 37° C. In certain embodiments, the outer capsule maintains integrity (e.g., absence of splits, cracks, or rupture of capsule shell) for about 2 hours at pH 5.5 and 37° C. In certain embodiments, the outer capsule disintegrates within about 1 hour at pH 7.4 and 37° C. In certain embodiments, the inner capsule maintains integrity (e.g., absence of splits, cracks, or rupture of capsule shell) for up to 1 hour at pH 7.4 and 37° C. In certain embodiments, the inner capsule disintegrates within 2 hours at pH 6.5 and 37° C.

In certain embodiments, the inner and/or outer capsule coating is comprised of poly(dl-lactide-co-glycolide, chitosan (Chi) stabilized with PVA (poly-vinylic alcohol), a lipid, an alginate, carboxymethylethylcellulose (CMEC), cellulose acetate trimellitiate (CAT), hydroxypropylmethyl cellulose phthalate (HPMCP), hydroxypropylmethyl cellulose, ethyl cellulose, food glaze, mixtures of hydroxypropylmethyl cellulose and ethyl cellulose, polyvinyl acetate phthalate (PVAP), cellulose acetate phthalate (CAP), shellac, copolymers of methacrylic acid and ethyl acrylate, or copolymers of methacrylic acid and ethyl acrylate to which a monomer of methylacrylate has been added during polymerization. Methylmethacrylates or copolymers of methacrylic acid and methylmethacrylate are available as Eudragit® polymers (Evonik Industries, Darmstadt, Germany). For example, Eudragit® L100 and Eudragit® S100 (anionic copolymers based on methacrylic acid and methyl methacrylate) can be used, either alone or in combination. Eudragit® L100 dissolves at about pH 6 and upwards and comprises between 46.0% and 50.6% methacrylic acid units per g dry substance; Eudragit® S100 dissolves at about pH 7 and upwards and comprises between 27.6% and 30.7% methacrylic acid units per g dry substance. Another exemplary group of encapsulating polymers are the polyacrylic acids Eudragit® L and Eudragit® S which optionally may be combined with Eudragit® RL or RS (copolymers of ethyl acrylate, methyl methacrylate and a low content of methacrylic acid ester with quaternary ammonium groups). These modified acrylic acids are useful since they can be made soluble at a pH of 6 to 7.5, depending on the particular Eudragit® chosen, and on the proportion of Eudragit® S to Eudragit® L, RS, and RL used in the formulation. In certain embodiments, a contemplated coating of the inner capsule is comprised of Eudragit EPO ReadyMix. In certain embodiments, a contemplated coating of the outer capsule is comprised of Eudragit® L100 (methylacrylic acid-methyl methacrylate co-polymer (1:1)) and Eudragit® S100 (methylacrylic acid-methyl methacrylate co-polymer (1:2)). In certain embodiments, a contemplated capsule is suitable for extended or timed release. In certain embodiments, a contemplated inner and/or outer capsule coating further comprises a band/seal, e.g., hypromellose, an opacifier, e.g., titanium dioxide, a plasticizer, e.g. triethyl citrate (TEC) or an anti-tacking agent, e.g. talc.

Further exemplary capsule-in-capsule formulations are described in U.S. Pat. No. 9,907,755.

Pharmaceutical compositions containing a bacterial strain disclosed herein can be presented in a unit dosage form, i.e., a pharmaceutical unit. A composition, e.g., a pharmaceutical unit provided herein, may include any appropriate amount of each bacterial strain, measured either by total mass or by colony forming units of the bacteria.

For example, a disclosed pharmaceutical composition or unit may include from about $10^3$ cfus to about $10^{12}$ cfus, about $10^6$ cfus to about $10^{12}$ cfus, about $10^7$ cfus to about $10^{12}$ cfus, about $10^8$ cfus to about $10^{12}$ cfus, about $10^9$ cfus to about $10^{12}$ cfus, about $10^{10}$ cfus to about $10^{12}$ cfus, about $10^{11}$ cfus to about $10^{12}$ cfus, about $10^3$ cfus to about $10^{11}$ cfus, about $10^6$ cfus to about $10^{11}$ cfus, about $10^7$ cfus to about $10^{11}$ cfus, about $10^8$ cfus to about $10^{11}$ cfus, about $10^9$ cfus to about $10^{11}$ cfus, about $10^{10}$ cfus to about $10^{11}$ cfus, about $10^3$ cfus to about $10^{10}$ cfus, about $10^6$ cfus to about $10^{10}$ cfus, about $10^7$ cfus to about $10^{10}$ cfus, about $10^8$ cfus to about $10^{10}$ cfus, about $10^9$ cfus to about $10^{10}$ cfus, about $10^3$ cfus to about $10^9$ cfus, about $10^6$ cfus to about $10^9$ cfus, about $10^7$ cfus to about $10^9$ cfus, about $10^8$ cfus to about $10^9$ cfus, about $10^3$ cfus to about $10^8$ cfus, about $10^6$ cfus to about $10^8$ cfus, about $10^7$ cfus to about $10^8$ cfus, about $10^3$ cfus to about $10^7$ cfus, about $10^6$ cfus to about $10^7$ cfus, or about $10^3$ cfus to about $10^6$ cfus of each bacterial strain, or may include about $10^3$ cfus, about $10^6$ cfus, about $10^7$ cfus, about $10^8$ cfus, about $10^9$ cfus, about $10^{10}$ cfus, about $10^{11}$ cfus, or about $10^{12}$ cfus of a bacterial strain or of each bacterial strain.

For example, a disclosed pharmaceutical composition or unit may include from about $10^3$ cfus to about $10^{12}$ cfus, about $10^6$ cfus to about $10^{12}$ cfus, about $10^7$ cfus to about $10^{12}$ cfus, about $10^8$ cfus to about $10^{12}$ cfus, about $10^9$ cfus to about $10^{12}$ cfus, about $10^{10}$ cfus to about $10^{12}$ cfus, about $10^{11}$ cfus to about $10^{12}$ cfus, about $10^3$ cfus to about $10^{11}$ cfus, about $10^6$ cfus to about $10^{11}$ cfus, about $10^7$ cfus to about $10^{11}$ cfus, about $10^8$ cfus to about $10^{11}$ cfus, about $10^9$ cfus to about $10^{11}$ cfus, about $10^{10}$ cfus to about $10^{11}$ cfus, about $10^3$ cfus to about $10^{10}$ cfus, about $10^6$ cfus to about $10^{10}$ cfus, about $10^7$ cfus to about $10^{10}$ cfus, about $10^8$ cfus to about $10^{10}$ cfus, about $10^9$ cfus to about $10^{10}$ cfus, about $10^3$ cfus to about $10^9$ cfus, about $10^6$ cfus to about $10^9$ cfus, about $10^7$ cfus to about $10^9$ cfus, about $10^8$ cfus to about $10^9$ cfus, about $10^3$ cfus to about $10^8$ cfus, about $10^6$ cfus to about $10^8$ cfus, about $10^7$ cfus to about $10^8$ cfus, about $10^3$ cfus to about $10^7$ cfus, about $10^6$ cfus to about $10^7$ cfus, or about $10^3$ cfus to about $10^6$ cfus of each bacterial strain, or may include about $10^3$ cfus, about $10^6$ cfus, about $10^7$ cfus, about $10^8$ cfus, about $10^9$ cfus, about $10^{10}$ cfus, about $10^{11}$ cfus, or about $10^{12}$ cfus of: (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain.

In certain embodiments, a provided pharmaceutical unit comprises at least $1 \times 10^3$ colony forming units of each bacterial strain (e.g., vegetative bacterial strain), or, at least $1 \times 10^4$ colony forming units of bacterial strain (e.g., vegetative bacterial strain), or, at least $1 \times 10^5$ colony forming units of bacterial strain (e.g., vegetative bacterial strain), or, at least $1 \times 10^6$ colony forming units of each bacterial strain (e.g., vegetative bacterial strain), or, at least $1 \times 10^7$ colony forming units of each bacterial strain (e.g., vegetative bacterial strain), or, at least $1 \times 10^8$ colony forming units of each bacterial strain (e.g., vegetative bacterial strain), or, at least $1 \times 10^9$ colony forming units of each bacterial strain (e.g., vegetative bacterial strain).

A composition, e.g., a pharmaceutical unit provided herein, may include each bacterial strain at any appropriate ratio, measured either by total mass or by colony forming units of the bacteria. For example, a disclosed pharmaceutical composition or unit may include two strains at a ratio of 0.1:1, 0.2:1, 0.25:1, 0.5:1, 0.75:1, 1:1, 2:1, 3:1, 4:1, 5:1, or 10:1, either by total mass or by colony forming units of the bacteria. For example, a disclosed pharmaceutical composition or unit may include three strains, e.g., (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and/or (iii) a *Roseburia* species strain, e.g., a *Roseburia hominis* strain, e.g., the RHO01 strain, at a ratio of 1:1:1, 1:1:2, 1:1:4, 1:2:1, 1:2:2, 1:2:4, 1:4:1, 1:4:2, 1:4:4, 2:1:1, 2:1:2, 2:1:4, 2:2:1, 2:4:1, 4:1:1, 4:1:2, 4:1:4, 4:2:1, 4:4:1, either by total mass or by colony forming units of the bacteria. For example, a disclosed pharmaceutical composition or unit may include (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and (iii) a *Roseburia* species strain, e.g., a *Roseburia hominis* strain, e.g., the RHO01 strain, at a ratio of 1:1:1, either by total mass or by colony forming units of the bacteria. For example, a disclosed pharmaceutical composition or unit may include approximately $1 \times 10^9$ viable organisms (e.g., cfus) of each of (i) a *Bacteroides* species strain, e.g., a *Bacteroides thetaiotaomicron* strain, e.g., the BTH01 strain; (ii) a *Eubacterium* species strain, e.g., a *Eubacterium hallii* strain, e.g., the EHA01 strain; and (iii) a *Roseburia* species strain, e.g., a *Roseburia hominis* strain, e.g., the RHO01 strain.

For example, disclosed compositions (e.g., a pharmaceutical unit such as e.g., a capsule) can include about 1 mg to about 5 mg (e.g., 2 mg to about 4 mg) of each separate bacterial strain, which can each be present in the unit, e.g., within about 5 mg to about 50 mg of a lyophilized powder form of the bacterial strain. For example, a pharmaceutical unit may comprise a total of about 30 mg to about 70 mg, about 30 mg to about 60 mg, about 30 mg to about 50 mg, about 30 mg to about 40 mg, about 40 mg to about 70 mg, about 40 mg to about 60 mg, about 40 mg to about 50 mg, about 50 mg to about 70 mg, about 50 mg to about 60 mg, about 80 mg to about 100 mg, about 90 mg to about 110 mg, about 100 mg to about 120 mg, or about 110 mg to about 150 mg of lyophilized powder forms of the bacterial strains. In certain embodiments, the pharmaceutical unit comprises a total of about 30 mg, 40 mg, 50 mg, 60 mg, 70 mg, 100 mg, 120 mg, 130 mg, 140 mg, or 150 mg of lyophilized powder form of the bacterial strains.

In certain embodiments, a disclosed composition such as a disclosed pharmaceutical unit may include about 5 to about 50 mg of each lyophilized powder form of a bacterial strain, for example, about 5 to about 45 mg, about 5 to about 40 mg, about 5 to about 35 mg, about 5 to about 30 mg, about 5 to about 25 mg, about 5 to about 15 mg, about 5 to about 10 mg, about 10 to about 50 mg, about 10 to about 35 mg of each lyophilized powder form of a bacterial strain, about 10 to about 20 mg, about 10 to about 15 mg, or about 15 to about 45 mg of each lyophilized powder form of a bacterial strain. In certain embodiments, a disclosed pharmaceutical unit comprises about 5, about 10, about 15, about 20, about 25, or about 30 mg of each lyophilized powder form of a bacterial strain. In certain embodiments, a disclosed pharmaceutical unit includes about 25 to about 50 mg of a lyophilized powder form of one bacterial strain and about 5 mg to about 10 mg of the remaining lyophilized powder forms of bacterial strains, or about 5 to about 15 mg of one lyophilized powder form of bacterial strain and about 5 to 10 mg of the remaining lyophilized powder forms of bacterial strains, for example, about 15 mg of one lyophilized powder form of bacterial strain and about 5 mg of the remaining lyophilized powder forms of bacterial strains, or about 15 mg to about 25 mg of each of two lyophilized powder forms of bacterial strains and about 5 mg to 10 mg of the remaining lyophilized powder form bacterial strains. In some embodiments, one or more (e.g. all) bacterial strain(s) of the lyophilized powder form are vegetative.

III. Therapeutic Uses

Compositions and methods disclosed herein can be used to treat various forms of gastrointestinal disorders, inflammatory disorders, and/or dysbiosis in a subject. The disclosure provides a method of treating a gastrointestinal disorder, inflammatory disorder, and/or dysbiosis in a subject. A contemplated method comprises administering to the subject an effective amount of a pharmaceutical composition, pharmaceutical unit, and/or bacterial strain disclosed herein, either alone or in a combination with another therapeutic agent to treat the gastrointestinal disorder, inflammatory disorder, and/or dysbiosis in the subject. A contemplated method comprises administering to the subject at least 2 vegetative bacterial strains each selected from the group consisting of: a *Bacteroides* species strain, a *Eubacterium* species strain, and a *Roseburia* species strain. In certain embodiments, the *Bacteroides* species is *Bacteroides thetaiotaomicron*. In certain embodiments, the *Eubacterium* species is *Eubacterium hallii*. In certain embodiments, the *Roseburia* species is *Roseburia hominis*.

As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals, e.g., human, a companion animal (e.g., dog, cat, or rabbit), or a livestock animal (for example, cow, sheep, pig, goat, horse, donkey, and mule, buffalo, oxen, or camel)).

It will be appreciated that the exact dosage of a pharmaceutical unit, pharmaceutical composition, or bacterial strain is chosen by an individual physician in view of the patient to be treated, in general, dosage and administration are adjusted to provide an effective amount of the bacterial agent to the patient being treated. As used herein, the "effective amount" refers to the amount necessary to elicit a beneficial or desired biological response. An effective amount can be administered in one or more administrations, applications or dosages and is not intended to be limited to a particular formulation or administration route. As will be appreciated by those of ordinary skill in this art, the effective amount of a pharmaceutical unit, pharmaceutical composition, or bacterial strain may vary depending on such factors as the desired biological endpoint, the drug to be delivered, the target tissue, the route of administration, etc. Additional factors which may be taken into account include the severity of the disease state; age, weight and gender of the patient being treated; diet, time and frequency of administration; drug combinations; reaction sensitivities; and tolerance/response to therapy.

It is understood that a disclosed bacterial strain or bacterial strain mixture may not require colonization of the gut of the subject and/or persistence in the subject in order elicit a beneficial or desired biological response. For example, in certain embodiments, a bacterial strain or bacterial strain mixture colonizes or partially colonizes the gut of the subject and/or persists in the subject after administration. In certain embodiments, a bacterial strain or bacterial strain mixture does not colonize the gut of the subject and/or persist in the subject after administration.

Gastrointestinal disorders include for example, inflammatory bowel disease (IBD), Crohn's disease (CD), ulcerative colitis (UC), ulcerative proctitis, microscopic colitis, irritable bowel syndrome (IBS; e.g., IBS-c, IBS-m, or IBS-d), functional diarrhea, functional constipation, coeliac disease, radiation enteritis, *Clostridium difficile* (*C. difficile*) infection (CDI), recurrent *C. difficile* infection (rCDI), *C. difficile* associated diarrheal disease (CDAD), colitis (e.g., infectious, ischemic, indeterminate, or radiation colitis), ulcers (including gastric, peptic, and duodenal ulcers), gastroesophageal reflux disease (GERD), pouchitis, gastroenteritis, pancreatitis, mucositis (e.g., oral mucositis, gastrointestinal mucositis, nasal mucositis and proctitis), necrotizing enterocolitis, esophagitis, non-ulcer dyspepsia, chronic intestinal pseudo-obstruction, functional dyspepsia, colonic pseudo-obstruction, duodenogastric reflux, ileus inflammation, post-operative ileus, heartburn (high acidity in the GI tract), constipation (e.g., constipation associated with use of medications such as opioids, osteoarthritis drugs, osteoporosis drugs, post surgical constipation, or constipation associated with neuropathic disorders), hemorrhoids, diverticular disease, chronic pancreatitis, blind loop syndrome, gastroparesis (including diabetic and/or idiopathic), diarrhea, dysphagia, fecal incontinence, short bowel syndrome (SBS), intestinal ischemia, infant regurgitation, infant rumination syndrome, cyclic vomiting syndrome, globus, *volvulus*, cancers of the gastrointestinal tract, and gastrointestinal allergies. It is contemplated that compositions and methods disclosed herein can be used to treat any functional gastrointestinal disorder, including, for example, a disorder mediated by or otherwise associated with a brain-gut interaction.

Inflammatory Bowel Disease or IBD is used interchangeably herein to refer to diseases of the bowel that cause inflammation and/or ulceration and includes without limitation Crohn's disease and ulcerative colitis. Crohn's disease (CD) and ulcerative colitis (UC) are chronic inflammatory bowel diseases of unknown etiology.

Ulcerative colitis (UC) afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

Crohn's disease, unlike ulcerative colitis, can affect any part of the bowel. The most prominent feature Crohn's disease is the granular, reddish-purple edmatous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual.

Inflammatory disorders may be characterized, for example, based on the primary tissue affected, the mechanism of action underlying the disorder, or the portion of the immune system that is misregulated or overactive. Examples of inflammatory disorders include inflammation of the lungs, joints, connective tissue, eyes, nose, bowel, kidney, liver, skin, central nervous system, vascular system, heart, or adipose tissue. In certain embodiments, inflammatory disorders which may be treated include inflammation due to the infiltration of leukocytes or other immune effector cells or mediators thereof into affected tissue. In certain embodiments, inflammatory disorders which may be treated include inflammation mediated by IgA and/or IgE antibodies. Other relevant examples of inflammatory disorders which may be treated by the present disclosure include inflammation caused by infectious agents, including but not limited to viruses, bacteria, fungi, and parasites. In certain embodiments, the inflammatory disorder that is treated is an allergic reaction. In certain embodiments, the inflammatory disorder is an autoimmune disease.

Inflammatory lung disorders include asthma, adult respiratory distress syndrome, bronchitis, pulmonary inflammation, pulmonary fibrosis, and cystic fibrosis (which may additionally or alternatively involve the gastro-intestinal tract or other tissue(s)). Immune mediated inflammatory diseases include systemic lupus erythematosus, systemic vasculitis, Sjogren's syndrome, alopecia areata, and systemic sclerosis. Inflammatory joint disorders include rheumatoid arthritis, seronegative spondyloarthropathies including ankylosing spondylitis, juvenile rheumatoid arthritis, osteoarthritis, gouty arthritis and other arthritic disorders. Inflammatory eye disorders include uveitis (including iritis), conjunctivitis, episcleritis, scleritis, and keratoconjunctivitis sicca. Inflammatory bowel disorders include Crohn's disease, ulcerative colitis, inflammatory bowel disease, and distal proctitis. Inflammatory skin disorders include disorders associated with cell proliferation, such as psoriasis, eczema, dermatitis (e.g., eczematous dermatitides, topic and seborrheic dermatitis, allergic or irritant contact dermatitis, eczema craquelee, photoallergic dermatitis, phototoxicdermatitis, phytophotodermatitis, radiation dermatitis, and stasis dermatitis), and acne. Inflammatory disorders of the endocrine system include, but are not limited to, autoimmune endocrinopathies, autoimmune thyroiditis (Hashimoto's disease), Type 1 diabetes, inflammation in liver and adipose tissue associated with Type II diabetes, and acute and chronic inflammation of the adrenal cortex. Inflammatory disorders of the cardiovascular system include, but are not limited to, coronary infarct damage, peripheral vascular disease, myocarditis, vasculitis, revascularization of stenosis, atherosclerosis, and vascular disease associated with Type II diabetes. Inflammatory disorders of the kidney include, but are not limited to, glomerulonephritis, interstitial nephritis, lupus nephritis, nephritis secondary to Wegener's disease, acute renal failure secondary to acute nephritis, Goodpasture's syndrome, post-obstructive syndrome and tubular ischemia. Inflammatory disorders of the liver include, but are not limited to, hepatitis (arising from viral infection, autoimmune responses, drug treatments, toxins, environmental agents, or as a secondary consequence of a primary disorder), biliary atresia, primary biliary cirrhosis and primary sclerosing cholangitis. Metabolic disorders with inflammatory etiology include insulin resistance, metabolic syndrome, obesity, Nonalcoholic fatty liver disease (NAFLD), and Nonalcoholic steatohepatitis (NASH). In certain embodiments, the inflammatory disorder is an autoimmune disease, for example, rheumatoid arthritis, lupus, alopecia, autoimmune pancreatitis, Celiac disease, Behcet's disease, Cushing syndrome, and Grave's disease. In certain embodiments, the inflammatory disorder is a rheumatoid disorder, for example, rheumatoid arthritis, juvenile arthritis, bursitis, spondylitis, gout, scleroderma, Still's disease, and vasculitis. Additional exemplary inflammatory disorders include eosinophilic esophagitis and eosinophilic gastroenteritis.

Generally, dysbiosis refers to a state of the microbiota or microbiome of the gut or other body area, including, e.g., mucosal or skin surfaces (or any other microbiota niche) in which the normal diversity and/or function of the ecological network is disrupted. Any disruption from a typical (e.g., ideal) state of the microbiota can be considered a dysbiosis, even if such dysbiosis does not result in a detectable decrease in health. This state of dysbiosis may be unhealthy (e.g., result in a diseased state), or it may be unhealthy under only certain conditions, or it may prevent a subject from becoming healthier. Dysbiosis may be due to a decrease in diversity of the microbiota population composition, the overgrowth of one or more population of pathogens (e.g., a population of pathogenic bacteria) or pathobionts, the presence of and/or overgrowth of symbiotic organisms able to cause disease only when certain genetic and/or environmental conditions are present in a patient, or the shift to an ecological network that no longer provides a beneficial function to the host and therefore no longer promotes health. A distal dysbiosis includes, but is not limited to, a dysbiosis outside of the lumen of the gastrointestinal tract.

It is contemplated that dysbiosis may include infection with a pathogenic bacterium of a genus selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella, Corynebacterium, Clostridium, Chlamydia, Chlamydophila, Campylobacter, Burkholderia, Brucella, Borrelia, Bordetella, Bifidobacterium*, and *Bacillus*. Further examples of pathogenic bacteria include *Aeromonas hydrophila, Campylobacter fetus, Plesiomonas shigelloides, Bacillus cereus, Campylobacter jejuni, Clostridium botulinum, Clostridium difficile, Clostridium perfringens*, enteroaggregative *Escherichia coli*, enterohemorrhagic *Escherichia coli*, enteroinvasive *Escherichia coli*, enterotoxigenic *Escherichia coli* (LT or ST), *Escherichia coli* 0157: H7, *Helicobacter pylori, Lysteria monocytogenes, Plesiomonas shigelloides, Salmonella typhi, Staphylococcus aureus, Vibrio cholerae, Vibrio parahaemolyticus, Vibrio vulnificus, Yersinia enterocolitica*, carbapenem-resistant Enterobacteriaceae (CRE), extended spectrum beta-lactam resistant Enterococci (ESBL), vancomycin-resistant Enterococci (VRE), and multi-drug resistant bacteria.

It is further contemplated that compositions and methods disclosed herein can be used to treat a disorder of the liver, pancreas, or gallbladder.

IV. Combination Therapy

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In certain embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In certain embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In certain embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. In certain embodiments, a side effect of a first and/or second treatment is reduced because of combined administration.

In certain embodiments, a method or composition described herein is administered in combination with one or more additional therapies, for example, one or more anti-inflammatory agents. In certain embodiments, a contemplated additional therapy may include an aminosalicylate, a corticosteroid, a Tumor Necrosis Factor (TNF) antagonist, linaclotide, an antibiotic, or an immunosuppressive agent (e.g., azathioprine, 6-mercaptopurine, cyclosporine, methotrexate, or tacrolimus (Prograf®)). In certain embodiments, a contemplated additional therapy may include a biologic agent (e.g., infliximab (Remicade®), adalimumab (Humira®), certolizumab pegol (Cimzia®), golimumab (Simponi®), or etanercept (Enbrel®)). It is contemplated that a subject treated with a disclosed method or composition may have had an inadequate response to a previous administration of a therapy, e.g., a previous administration of an aminosalicylate, a corticosteroid, or a biologic agent.

Further therapeutic agents suitable for use in combination therapy with a pharmaceutical composition or unit described herein include proton pump inhibitors (such as pantoprazole (Protonix®), lansoprazole (Prevacid®), esomeprazole (Nexium®), omeprazole (Prilosec®), and rabeprazole), H2 blockers (such as cimetidine (Tagamet®), ranitidine (Zantac®), famotidine (Pepcid®), and nizatidine (Axid®)), prostaglandins (such as misoprostol (Cytotec®)), sucralfate, and antacids.

In certain embodiments, a pharmaceutical composition or unit may include, or be administered in combination with, a corticosteroid. Corticosteroids are a class of chemicals that includes steroid hormones naturally produced in the adrenal cortex of vertebrates and analogues of these hormones that are synthesized in laboratories. Corticosteroids are involved in a wide range of physiological processes, including stress response, immune response, and regulation of inflammation, carbohydrate metabolism, protein catabolismblood electrolyte levels, and behavior. Exemplary corticosteroids include betamethasone, budesonide, cortisone, dexamethasone, hydrocortisone, methylprednisolone, prednisolone, prednisone, or deflazacort. It is contemplated that a subject treated with a disclosed method or composition may have had an inadequate response to a previous administration of a corticosteroid.

In certain embodiments, a pharmaceutical composition or unit may include, or be administered in combination with, an aminosalicylate. Exemplary aminosalicylate include 4-Aminosalicylic acid, Balsalazide, Olsalazine, Sulfasalazine, and Mesalazine (5-Aminosalicylic acid). It is contemplated that a subject treated with a disclosed method or composition may have had an inadequate response to a previous administration of mesalamine, for example, a previous administration of ≥2.4 g/day mesalamine orally for at least 8 weeks.

In certain embodiments, a pharmaceutical composition or unit may include, or be administered in combination with, a Tumor Necrosis Factor (TNF) antagonist. Exemplary TNF antagonists include infliximab (Remicade®), adalimumab (Humira®), certolizumab pegol (Cimzia®), golimumab (Simponi®), etanercept (Enbrel®), thalidomide (Immunoprin), lenalidomide (Revlimid®), pomalidomide (Pomalyst®, Imnovid®), xanthine derivatives (e.g., pentoxifylline), and bupropion. It is contemplated that a subject treated with a disclosed method or composition may have had an inadequate response to a previous administration of a TNF antagonist.

In certain embodiments, a pharmaceutical composition or unit may include, or be administered in combination with, an integrin $\alpha\beta7$ antagonist, e.g., vedolizumab. It is contemplated that a subject treated with a disclosed method or composition may have had an inadequate response to a previous administration of an integrin $\alpha\beta7$ antagonist.

In certain embodiments, a pharmaceutical composition or unit may include, or be administered in combination with, an anti-bacterial agent, e.g., an antibiotic. A disclosed method may comprise pretreatment with an antibiotic, e.g., administration of an antibiotic to a subject prior to administration of a disclosed pharmaceutical composition or unit. Exemplary antibiotics for use in combination therapy include vancomycin, metronidazole, gentamicin, colistin, fidaxomicin, telavancin, oritavancin, dalbavancin, daptomycin, cephalexin, cefuroxime, cefadroxil, cefazolin, cephalothin, cefaclor, cefamandole, cefoxitin, cefprozil, ceftobiprole, cipro, Levaquin, floxin, tequin, avelox, norflox, tetracycline, minocycline, oxytetracycline, doxycycline, amoxicillin, ampicillin, penicillin V, dicloxacillin, carbenicillin, methicillin, ertapenem, doripenem, imipenem/cilastatin, meropenem, amikacin, kanamycin, neomycin, netilmicin, tobramycin, paromomycin, cefixime, cefdinir, cefditoren, cefoperazone, cefotaxime, ceftazidime, ceftibuten, ceftizoxime, ceftriaxone, cefoxotin, and/or streptomycin.

In certain embodiments, a pharmaceutical composition or unit may include, or be administered in combination with, an anti-fungal or anti-viral agent. Exemplary anti-viral agents include abacavir, acyclovir, adefovir, amprenavir, atazanavir, cidofovir, darunavir, delavirdine, didanosine, docosanol, efavirenz, elvitegravir, emtricitabine, enfuvirtide, etravirine, famciclovir, foscarnet, fomivirsen, ganciclovir, indinavir, idoxuridine, lamivudine, lopinavir, maraviroc, MK-2048, nelfinavir, nevirapine, penciclovir, raltegravir, rilpivirine, ritonavir, saquinavir, stavudine, tenofovir trifluridine, valaciclovir, valganciclovir, vidarabine, ibacitabine, amantadine, oseltamivir, rimantidine, tipranavir, zalcitabine, zanamivir and zidovudine. Exemplary anti-fungal agents include natamycin, rimocidin, filipin, nystatin, amphotericin B, candicin, and hamycin, miconazole, ketoconazole, clotrimazole, econazole, omoconazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, and albaconazole, abafungin, terbinafine, naftifine, butenafine, anidulafungin, caspofungin, micafungin, polygodial, benzoic acid, ciclopirox, tolnaftate, undecylenic acid, flucytosine or 5-fluorocytosine, griscofulvin, and haloprogin.

In certain embodiments a pharmaceutical composition or unit may include, or may be administered in combination with a prebiotic, i.e., a compound or composition which modifies the growth, maintenance, activity and/or balance of the intestinal micro flora (e.g., can allow for specific changes in the composition and/or activity of the microbiome). Exemplary prebiotics include complex carbohydrates, complex sugars, resistant dextrins, resistant starch, amino acids, peptides, nutritional compounds, biotin, polydextrose, fructooligosaccharide (FOS), galactooligosaccharides (GOS), inulin, lignin, *psyllium*, chitin, chitosan, chitosanoligosaccharides, lacitol, gums (e.g., guar gum), high amylose cornstarch (HAS), cellulose, β-glucans, hemi-celluloses, lactulose, mannooligosaccharides, mannan oligosaccharides (MOS), oligofructose-enriched inulin, oligofructose, oligodextrose, tagatose, trans-galactooligosaccharide, pectin, resistant starch, isomaltoligosaccharides, and xylooligosaccharides (XOS). Prebiotics can be found in foods (e.g., acacia gum, guar seeds, brown rice, rice bran, barley hulls, chicory root, Jerusalem artichoke, dandelion greens, garlic, leek, onion, asparagus, wheat bran, oat bran, baked beans, whole wheat flour, and banana), and breast milk. Prebiotics can also be administered in other forms (e.g., a capsule or dietary supplement).

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present disclosure, whether explicit or implicit herein. For example, where reference is made to a particular compound, that compound can be used in various embodiments of compositions of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments may be variously combined or separated without parting from the present teachings and disclosure. For example, it will be appreciated that all features described and depicted herein can be applicable to all aspects of the disclosure described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also includes the specific quantitative value itself, unless specifically stated otherwise. As used herein, the term "about" refers to a +10% variation from the nominal value unless otherwise indicated or inferred.

It should be understood that the order of steps or order for performing certain actions is immaterial so long as the present disclosure remains operable. Moreover, two or more steps or actions may be conducted simultaneously.

The use of any and all examples, or exemplary language herein, for example, "such as" or "including," is intended merely to illustrate better the present disclosure and does not pose a limitation on the scope of the disclosure unless claimed. No language in the specification should be construed as indicating any non-claimed element as essential to the practice of the present disclosure.

EXAMPLES

The following Examples are merely illustrative and are not intended to limit the scope or content of the disclosure in any way.

Example 1—Overview of Bacterial Strain Selection Process for Consortium 1 (C1)

Consortium 1 (C1), a live biotherapeutic product for development as a treatment for gastrointestinal disorders, for example, dysbiosis and/or immune mediated inflammatory disorders, such as ulcerative colitis, Crohn's disease, and other forms of inflammatory bowel disease (IBD), comprises a consortium of three bacterial strains, namely *Bacteroides thetaiotaomicron* BTH01, *Eubacterium hallii* EHA01, and *Roseburia hominis* RHO01.

Candidate bacterial strains of interest were isolated from healthy donor stool samples, purified and characterized using standard anaerobic microbiological procedures. All stool donors underwent comprehensive clinical and laboratory testing to confirm healthy status including screening for infectious agents to minimize risk of transmissible infection. Serology screening included HIV-1/HIV-2 (IgG and EIA), HTLV-I and HTLV-II (Ab), Hepatitis A virus (IgM), Hepatitis B virus (HBSAg, anti-HBc IgG and IgM), Hepatitis C virus (anti-HCV IgG), *Treponema pallidum* (EIA, or RPR if EIA is positive), *Strongyloides stercoralis* Ab, CMV Viral Load, and EBV Viral Load. Stool screening included *Clostridium difficile* toxin A/B (PCR), Routine bacterial culture for enteric pathogens (with enrichment) including *H. pylori* EIA, *Salmonella, Shigella, Yersinia, Campylobacter,* and *Vibrio, E. coli* 0157 (perform *E. coli* 0157 culture, if stx 1/2 EIA+ve), Shiga-like toxins stx 1/2 (*Shigella*) EIA, Culture-based assays for vancomycin-resistant *Enterococcus* (VRE), extended spectrum beta-lactamase (ESBL) producers, carbapenem-resistant Enterobacteriaceae (CRE), and methicillin-resistant *Staphylococcus aureus* (MRSA), Giardia antigen (EIA), *Cryptosporidium* antigen (EIA), *Cyclospora, Isospora*, and Microsporidia (Microscopic observation with acid fast stain), Ova and Parasites (Microscopic observation), Rotavirus (EIA), Norovirus GI/GII (RT-PCR), and Adenovirus 40,41 EIA.

16S RNA sequencing was used to taxonomically identify candidate strains during the selection and screening process. Bacterial strains of interest underwent extensive phenotypic and genotypic characterization. Based on these data, a subset of candidate therapeutic strains were selected for further assessment in cell-based in vitro functional assays and in an in vivo mouse DSS colitis model (Chassaing et al., *Curr Protoc Immunol.;* 104: Unit 15.25 (2014)) to assess their potential in modulating inflammation and gut barrier integrity. Based on the results of these experiments, three bacterial strains were selected belonging to species taxa: *Bacteroides thetaiotaomicron, Eubacterium hallii*, and *Roseburia hominis*. The 16S RNA sequences of RHO01, BTH01, and EHA01 are provided in SEQ ID NOs: 1, 2, and 3, respectively. The taxonomic identity of each bacterial strain was confirmed via whole genome sequencing (WGS). The whole genome sequence of RHO01 is provided in SEQ ID NOs: 4-32. The whole genome sequence of BTH01 is provided in SEQ ID NOs: 33-390. The whole genome sequence of EHA01 is provided in SEQ ID NOs: 391-523. In accordance with the Budapest Treaty, strains BTH01, EHA01, and RHO01 were deposited with the DSMZ (Deutsche Sammlung von Mikroorganismen und Zellkulturen GmbH, Inhoffenstraße 7B, 38124 Brunswick, Germany) under DSM numbers BTH01 (DSM-32919), EHA01 (DSM-32920), and RHO01 (DSM-32921), respectively, on Sep. 14, 2018.

Information and data in support of the rationale for selecting the *Bacteroides thetaiotaomicron* strain (BTH01), the *Eubacterium hallii* strain (EHA01), and the *Roseburia hominis* strain (RHO01) for development of C1 are presented throughout the Examples, especially in Examples 2-6.

Example 2—Taxonomic and Phenotypic Characterization of C1 Bacterial Strains

A live biotherapeutic product, Consortium 1 (C1), was prepared by mixing three bacterial strains, namely BTH01, EHA01, and RHO01. Table 1 shows some of the physiological and metabolic characteristics of the C1 bacterial strains BTH01, EHA01 and RHO01. Gram staining of the three C1 bacterial strains showed EHA01 to be Gram positive, whereas, both BTH01 and RHO01 are Gram negative. All three strains are obligate anaerobes.

In order to investigate characteristics often found to be different among the strains of same bacterial species, analysis of carbon source utilization was performed for the C1 bacterial strains. The BTH01, EHA01 and RHO01 strains were evaluated for their ability to metabolize 190 carbon and 95 nitrogen sources using phenotypic microarrays (Biolog, Hayward, CA). As indicated in Table 1, BTH01 appeared to be most versatile in utilizing 34 unique carbon sources whereas EHA01 appeared to be least versatile, utilizing 8 unique carbon sources. Each of the BTH01, EHA01 and RHO01 strains were able to metabolize a few unique carbon sources that are not reported in the literature for their respective species. BTH01 was able to utilize D-Mannose, Maltose, a-D-Glucose, D-Galactose, Lactulose, Maltotriose, N-Acetyl-b-D-Mannosamine, N-Acetyl-D Glucosamine, D-Trehalose, a-D-Lactose, Sucrose, Turanose, Gentiobiose, D-Melibiose, D-Fructose, L-Fucose, L-Arabinose, D-Glucuronic Acid, D-Xylose, L-Rhamnose, D-Galacturonic Acid, α-Cyclodextrin, β-Cyclodextrin, γ-Cyclodextrin, Glycogen, Laminarin, Mannan, Pectin, N-Acetyl-D-Galactosamine, b-Methyl-D-Galactoside, D-Arabinose, Maltitol, Palatinose, and D-Raffinose. RHO01 was able to utilize D-Mannose, Maltose, a-D-Glucose, N-Acetyl-D Glucosamine, D-Trehalose, a-D-Lactose, Sucrose, Turanose, Gentiobiose, D-Cellobiose, Amygdalin, Arbutin, D-Melezitose, Salicin, D-Glucosamine, and b-Methyl-D-glucoside. EHA01 was able to utilize D-Mannose, Maltose, a-D-Glucose, D-Galactose, Lactulose, Maltotriose, N-Acetyl-b-D-Mannosamine, and L-Tartaric Acid.

Microbiota play a central role in bile acid metabolism. Analysis of IBD patient microbiota indicate an overall decrease in biodiversity with a specific decrease in bacteria from the Bacteroidetes and Firmicutes phylum, that are responsible for about 44% of the bile hydrolase activity in the gut (Baars et al., *Microorganisms* 3 (4): 641-666 (2015)). Consequently, restoring bile acid metabolism with microbes may be a potential avenue of therapeutic intervention. As conjugated bile salts possess antimicrobial activity, bacteria have evolved to produce bile salt hydrolase (BSH) to neutralize this adverse activity. A number of bacterial strains including *Bacteroides* species are tolerant to physiological concentrations of bile (Pumbwe et al., *Microb Pathog.* 43 (2-3): 78-87 (2007)).

In order to analyze bile tolerance among C1 bacterial strains, BTH01, EHA01 and RHO01, growth assays were performed in cultivation media with bile concentrations ranging from 0.2% up to 1.0%. Results are shown in Table 1. Compared to controls grown without bile added, 85% of the maximum OD was achieved by BTH01 in the presence of up to 0.6% bile concentration in growth media. RHO01 was also somewhat bile tolerant reaching 35% of maximum OD in the presence of 0.4% bile. EHA01 was sensitive to bile and exhibited growth inhibition even in the presence of 0.2% bile.

TABLE 1

Taxonomic Identities and Phenotypic Characteristics of C1 Bacterial Strains

| Strain Name | Genus Species (WGS) | Gram Stain | Oxygen Tolerance | Carbon Sources Utilized[1] | Nitrogen Sources Utilized | Bile Tolerance (%)[2] | Optimal pH Range |
|---|---|---|---|---|---|---|---|
| BTH01 | *Bacteroides thetaiotaomicron* | N | obligate anaerobe | 34 | 4 | 0.6[3] | 6.75-8.0 |

TABLE 1-continued

Taxonomic Identities and Phenotypic Characteristics of C1 Bacterial Strains

| Strain Name | Genus Species (WGS) | Gram Stain | Oxygen Tolerance | Carbon Sources Utilized[1] | Nitrogen Sources Utilized | Bile Tolerance (%)[2] | Optimal pH Range |
|---|---|---|---|---|---|---|---|
| EHA01 | Eubacterium hallii | P | obligate anaerobe | 8 | 3 | 0[3] | 6.0-7.25 |
| RHO01 | Roseburia hominis | N | obligate anaerobe | 16 | NA[5] | 0.4[4] | 6.0-6.75 |

N = Gram negative; P = Gram positive; WGS = whole genome sequencing
[1] 190 unique carbon sources were tested
[2] Physiological concentrations of bile salts in human intestine are typically between 0.1 to 1.3% (Pumbwe et al., 2007)
[3] 85% of the maximum OD was observed with a lag of eight hours to exponential phase in the presence of 0.6% bile in cultivation media
[4] 35% of the maximum OD was observed with a lag of five hours to exponential phase in the presence of 0.4% bile in cultivation media
[5] RHO01 growth was not supported by the minimal media used for the nitrogen source utilization assay Literature indicates all three of the C1 representative species to be non-sporulating. Using two distinct sporulation-inducing methods (i.e., heat-shock and chemical-shock), none of the C1 bacterial strains were found to sporulate. A positive control *Clostridium butyricum* (ATCC 19398) strain obtained from ATCC produced spores with both test methods as shown in Table 2.

TABLE 2

Assessment of Sporulation

| Test strain | Percent Sporulation with Heat-Shock Method | Percent Sporulation with Ethanol-Shock Method |
|---|---|---|
| C. butyricum | 2.68 | 24.49 |
| BTH01 | 0.0 | 0.0 |
| EHA01 | 0.0 | 0.0 |
| RHO01 | 0.0 | 0.0 |

Each bacterial strain from research cell banks (RCB) was tested for its susceptibility/resistance to a panel of clinically relevant antibiotics using an agar dilution minimal inhibitory concentration method (MIC), and each strain (RCB) was shown to be susceptible to at least two clinically relevant antibiotics (Table 3A).

TABLE 3A

Phenotypic Antibiotic Susceptibility Results for Research Cell Banks

| Compound | Class | Concentration Range (µg/mL) Max | Concentration Range (µg/mL) Min | Determined MIC (µg/mL), Interpretation BTH01 | Determined MIC (µg/mL), Interpretation EHA01 [1] | Determined MIC (µg/mL), Interpretation RHO01 [1] |
|---|---|---|---|---|---|---|
| Ampicillin | Penicillins | 128 | 0.06 | 32 (R) | 0.06 (S) | ≤0.016 (S) |
| Cefotetan | Cephalosporins (2nd generation) | 256 | 0.12 | 256 (R) | N/T | N/T |
| Clindamycin | Lincosamides | 32 | 0.016 | >32 (R) | 0.03 (S) | ≤0.016 (S) |
| Imipenem | Carbapenems | 32 | 0.016 | 0.5 (S) | 0.008 (S) | 0.12 (S) |
| Metronidazole | Other | 128 | 0.06 | 2 (S) | 0.06 (S) | 0.03 (S) |
| Moxifloxacin | Quinolones | 8 | 0.004 | 2 (S) | 2 (S) | 32 (R) |
| Vancomycin | Glycopeptides | 128 | 0.06 | 64 (N/A) | 0.12 (N/A) | 0.25 (N/A) |

N/A = no interpretive criteria available; N/T = not tested R = resistant; S = susceptible
[1] No growth on required CLSI agar; testing executed using Etests Example 3—Whole Genome Sequencing (WGS) Analysis of C1 Bacterial Strains Illumina® WGS of each bacterial strain genome (BTH01, EHA01 and RHO01) was performed to confirm taxonomic identity, and to evaluate the genomic evidence for the presence of antibiotic resistance genes, virulence factors and toxins, including evidence of associated mobile genetic elements.

Example 3.1—Genomic Analytical Methods

Taxonomic identity was assessed using the Joint Genome Institute's Microbial Species Identifier, which compares the average nucleotide identity (ANI) to a database of curated genomes and assigns taxonomy if ANI exceeds 96.5% and an alignment length of >70% between the query and reference genomes (Varghese et al., *Nucleic Acids Research*, 43 (14): 6761-6771 (2015)).

The presence of putative virulence factors, including toxins, was determined by comparing candidate bacterial strain genomes to three curated databases using BLAST: VFDB (Chen et al., *Nucleic Acids Res.* 2005 Jan. 1; 33 (2005)), PATRIC (Mao et al., *Bioinformatics*, 31 (2): 252-258 (2015)) and PHIDIAS (Xiang et. al., *Genome Biol.* 8 (7): R150 (2007)). Hits exceeding an e-value of 1e-7 with 70% identity over 70% of the reference sequence of the database hits were retained (Mao et al., 2015).

Putative antibiotic resistance genes were identified using the Resistance Gene Identifier/CARD package (Jia et al., *Nucleic Acids Res.* 45 (Database issue): D566-D573 (2017)).

Mobile genetic elements (MGE) within candidate bacterial strain genomes were predicted using IslandViewer 4

(Bertelli et al., *Nucleic Acids Res*. 45 (W1): W30-W35 (2017)) and Virsorter (for bacteriophage; Roux et al., eLife. 2015; 4: e08490 (2015)) to assess the theoretical potential for gene transfer. Default thresholds for MGE detection were used for Island Viewer 4 and phage predictions classified as "Confident" by Virsorter were retained.

Example 3.2—Results and Interpretation

Taxonomic assignments for candidate bacterial species exceeded the 96.5% ANI threshold for BTH01 (ANI=99.8%), EHA01 (ANI=97.5%), and RHO01 (ANI=98.1%).

While sequence analysis indicated the presence of antibiotic resistance in BTH01 and RHO01, no genomic evidence for antibiotic resistance was detected in EHA01. To confirm the clinical relevance of these data, empirical testing for antibiotic resistance/susceptibility was conducted on C1 research cell banks; results are presented in Table 3A. Selection of antibiotics was based on relevant antibiotic susceptibility patterns for the bacterial taxa under consideration. Importantly, all three candidate bacterial strains were shown to be susceptible to the majority of the antibiotics tested. While nucleic-acid-based techniques may become useful tools in the future for predicting antibiotic resistance, presently, there is little evidence to support the use of WGS to inform antibiotic susceptibility; concerns remain related to method standardization, accuracy and clinical interpretability (Ellington et al., *Clin Microbiol Infect*. 23 (1): 2-22 (2017)).

In our assessment of virulence factors, no genes directly associated with host mortality (e.g. genes specifically coding for toxins or secretion systems) were detected. Virulence factors identified were related to metabolic function or tolerance to physiological conditions within the host, which when impaired in pathogens through in vitro mutagenesis reduces their virulence by impairing growth or survival. It is thus not unexpected that genomes of host-associated commensal bacteria contain homologs of these genes and thus these data are not considered a clinically relevant safety risk.

In our assessment of MGE, no regions of the genomes of any strain were identified as derived from prophage using our criteria. Additionally, the bacterial candidate strains have been tested for the presence of bacteriophage and prophage via EM analyses (±mitomycin C induction). No bacteriophage or inducible prophage were detected. While other signatures of MGE were detected as shown in Table 3B, many types of MGE are not transmissible among bacteria (e.g. intracellular MGE; Siguier et al., *FEMS Microbiology Reviews*, 38 (5): 865-891 (2013)).

TABLE 3B

Presence of Predicted Antimicrobial Resistance Genes and Flanking Putative Mobile Genetic Elements (MGE)

| Strain Name | Gene | Antibiotic | Mechanism | MGE |
|---|---|---|---|---|
| BTH01 | ErmB | macrolide; lincosamide; streptogramin | antibiotic target alteration | Y |
|  | adeF | fluoriquinolone; tetracycline | antibiotic efflux | N |
|  | tetQ | tetracycline | antibiotic target protection | Y |
| EHA01 | None | N/A | N/A | N/A |
| RHO01 | tetW | tetracycline | antibiotic target protection | Y |

Example 4—Short-Chain Fatty Acid (SCFA) Production Profile of C1 Bacterial Strains Grown Individually or as a Consortium Short-Chain Fatty Acids (SCFAs) produced by human gut microbes include butyrate, acetate and propionate, all three of which are found to contribute to the maintenance of intestinal homeostasis through multiple mechanisms (Lee and Hase, *Nat Chem Biol* 10 (6): 416-424 (2014); Hoeppli et al., *Front Immunol* 6:61 (2015); Koh et al., *Cell* 165 (6): 1332-1345 (2016)). Butyrate is mainly produced by *Clostridium* cluster IV and XIVa species that include EHA01 and RHO01. On the other hand, *Bacteroides* species are major producers of acetate and propionate. The SCFA production profile of each of the C1 bacterial strain was evaluated after 72 hours of growth in batch culture in YCFAC media. As seen in FIG. 1A, acetate and propionate are the most abundant SCFA produced by BTH01. On the other hand, acetate and butyrate are the most abundant SCFA produced by EHA01 and RHO01, as expected (FIG. 1B, C). None of the three C1 bacterial strains produce a high amount of lactate. When grown as a consortium in batch cultures, acetate and butyrate are the most abundant SCFA produced (FIG. 1D).

Figure 2:
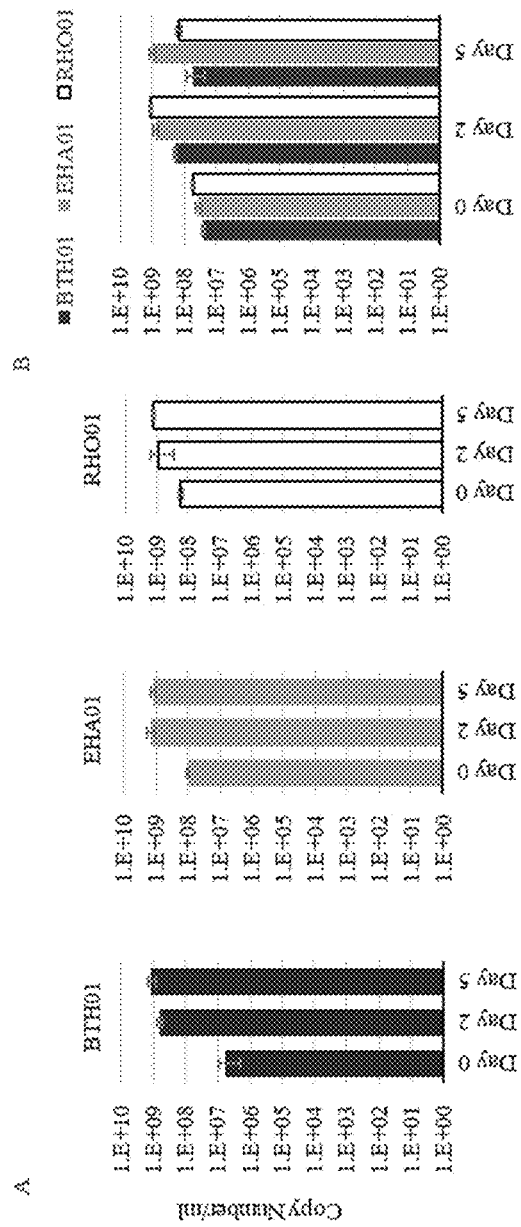
FIGS. 2A-2B depict the abundance of each of the C1 bacterial strains in individual as well as consortium fed-batch cultures. C1 bacterial strains were grown in replicate either individually or in consortium.

Certain microbial strains are known to produce compounds or toxins that inhibit growth of other microbes. There are examples of such antimicrobial compounds produced by strains belonging to gut microbiota (Spinler et al., *Anaerobe*. 14 (3): 166-71 (2008); Arief et al., *Benef Microbes*. 6 (4): 603-13 (2015); Renye Jr. et al., *Biotechnol Lett*. (11): 1947-1954 (2016)). In each of these examples, production of an antimicrobial compound results in significant growth inhibition of the susceptible strains within a short period of time (18 to 48 hours). Therefore, to rule out any antagonistic relationship between C1 bacterial strains, fed-batch culturing experiments were performed. Each of the C1 bacterial strains were grown either individually or in a consortium after normalizing inoculation cell counts. Cultures were transferred to fresh media after about 48 hours for 5 consecutive days. The 48-hour fed-batch transfer time was chosen based on previously determined growth rates of the individual strains in the YCFAC medium (data not shown), with the rationale of allowing enough time for each strain to reach to a maximum OD. Samples from replicate cultures at day 0 (right after inoculation), day 2 and day 5 were analyzed by qPCR to assess abundance of each of the C1 strains. As seen in FIG. 2A, all three C1 strains grew to a similar extent over time in individual cultures. When grown in consortium, abundance of all three C1 strains was maintained at or above the levels of inoculation over 5-day fed-batch cultures (FIG. 2B) indicating absence of any toxic/growth inhibitory relationship among C1 strains. EHA01 levels were higher compared to the BTH01 and RHO01 levels in day 5 samples, which is most likely resulting from higher growth rate of EHA01 compared to BTH01 and RHO01 in the YCFAC medium used for this experiment.

Example 5—Demonstration of Cross-Feeding Between C1 Bacterial Strains

The stability and function of a microbial community depends on nutritional interactions between community members such as the cross-feeding of essential small molecules synthesized by a subset of the population (Seth and Taga, 2014). Starches (polymers of glucose) are the most abundant polysaccharides in the human diet and occur in many foods, including cereal grains, legumes, and potatoes (Diet and Health: Implications for Reducing Chronic Disease Risk, National Academies Press (US), 1989)). In a typical Western diet, 33 to 50% of the caloric intake is in the form of carbohydrate. Approximately 17 to 25% of this total carbohydrate is represented by starch (britannica.com/science/carbohydrate/Role-in-human-nutrition, available on the world wide web).

To investigate if C1 bacterial strains exhibit cross-feeding, metabolic traits of the individual strains were identified that might allow these strains to cross-feed each other. For example, *Bacteroides* species encode an elaborate starch utilization system (Wexler et al., *Microb Genom.* 3 (11) (2017)). This includes extracellular secreted enzymes that generate starch digestion products such as oligomers, trimers (Maltotriose), dimers (maltose) and glucose monomers. From the experiments listed above to determine carbon source utilization of C1 strains, it was evident that EHA01 could utilize starch digestion products. However, based on the literature and available sequenced genomes, *Eubacterium hallii* species are not expected to express starch degradation enzymes.

Figure 3:
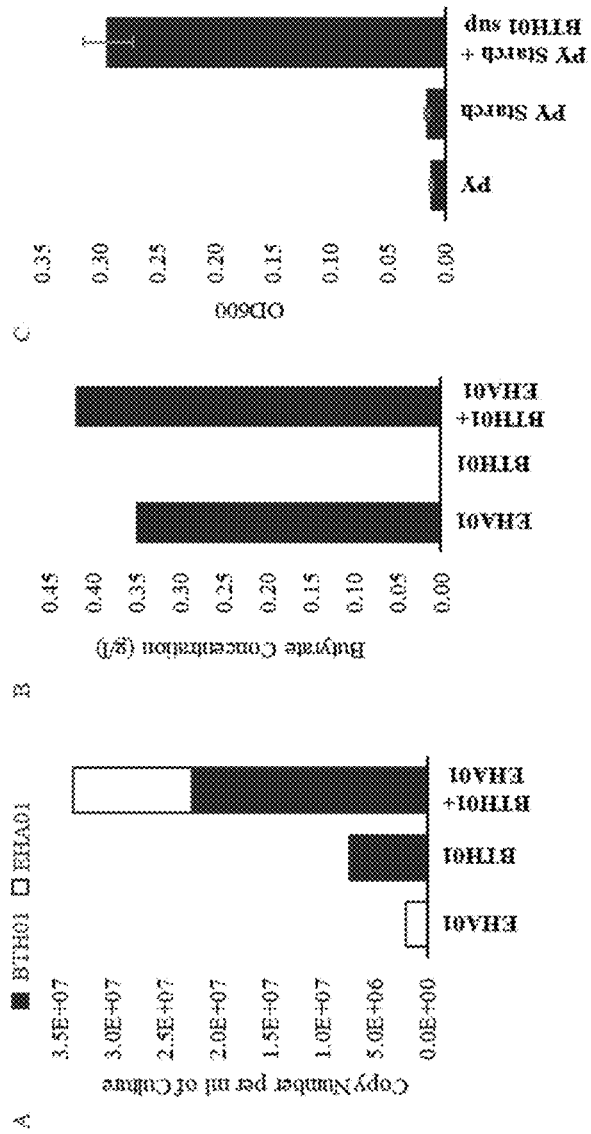
FIGS. 3A-3C depicts cross-feeding between EHA01 and BTH01. The EHA01 and BTH01 strains were grown individually or in co-culture in the presence of starch supplemented as a sole carbon source in the growth medium. After 48 hours of batch culture, the copy number of each strain was determined by species-specific qPCR (3A) and spent medium from each culture was analyzed for production of butyrate using HPLC (3B). In another experiment, the EHA01 strain was grown in Peptone-Yeast extract (PY) growth medium lacking any carbon source, PY medium supplemented with starch (PY starch) and PY medium supplemented with starch and 50% filter sterilized spent medium from a BTH01 culture previously grown for 48 hours. ODs of each of the three cultures are shown (3C).

As seen in FIG. 3A, qPCR-based copy number calculations showed that EHA01 exhibited poor growth compared to BTH01 in presence of starch as a sole carbon source provided in the growth medium. The copy number of EHA01 increased when grown in co-culture with BTH01 (FIG. 3A). A concomitant 25% increase in butyrate production by EHA01 was also observed when grown in co-culture with BTH01 in presence of starch as a sole carbon source (FIG. 3B).

To determine whether products secreted by BTH01 (including the starch degradation enzymes) could be responsible for boosting the growth of EHA01 in the presence of starch as a sole carbon source in the growth media, EHA01 culture media was supplemented with filtered supernatant from spent media in which BTH01 was previously grown. As seen in FIG. 3C, EHA01 growth in media containing starch as a sole carbon source was promoted only when BTH01 supernatant was added.

*Eubacterium hallii* species are reported to produce and secrete vitamin B12 which is essential for growth of other gut microbes including *Bacteroides thetaiotaomicron* species that sequester vitamin B12 from the extracellular milieu (Engels et al., *Front Microbiol.* 7:713 (2016)). Consequently, vitamin B12-mediated cross-feeding may be boosting the growth of BTH01 in co-culture with EHA01, as indicated by an increase in BTH01 copy number in co-culture compared to BTH01 grown in individual culture (FIG. 3A).

Taken together, these results indicate cross-feeding and mutually beneficial effects of co-culture between BTH01 and EHA01. *Roseburia* species are also able to utilize starch as sole carbon source. RHA01 and EHA01 showed similar cross-feeding when growth on starch as sole carbon source (data not shown).

Example 6—In Vitro and In Vivo Functional Activity of C1 Bacterial Strains and C1

This example describes studies of the activity of C1 bacterial strains separately, and as a consortium, in several in vitro and in vivo models, which may provide mechanistic insight to the potential clinical benefits.

Example 6.1—Preparation of Freshly Cultured Bacterial Strains and Consortium Working Stock Solutions for Cell Culture Assays Freshly cultured bacteria from overnight cultures were prepared in anaerobic conditions. EHA01 and RHO01 were grown using a rotator to allow mixing whereas BTH01 was grown without mixing. Bacteria were centrifuged at 4300×g for four minutes. Bacteria were washed once with pre-reduced anaerobic PBS (Gibco). Working stock solutions were prepared by resuspending washed bacteria with anaerobic PBS to the optical density of OD600=0.3 (~$10^8$ CFU/ml). 10-fold serial dilutions were made using anaerobic PBS for specific assays. The consortium of three bacteria was prepared by mixing working stock solutions of three individual bacteria 1:1:1 by volume. Lyophilized bacteria were prepared in anaerobic conditions using the same method of preparation as used to manufacture C1 drug substances. Working stock solutions of lyophilized bacteria were prepared by resuspending lyophilized bacteria in pre-reduced anaerobic PBS as described above.

Example 6.2—HT29-MTX-E12 Human Epithelial Barrier In Vitro Assay

The HT29-MTX-E12 human epithelial cell line (Sigma Aldrich cat #12040401-1VL) was cultured in 37° C. and 5% $CO_2$ using high glucose DMEM containing 4.00 mM L-glutamine, 4500 mg/L and sodium pyruvate (HyClone™) supplemented with 10% FBS (Tissue Culture Biologicals), 100 I·U/mL Penicillin, 100 µg/mL Streptomycin and 0.292 mg/mL L-glutamine (Corning). Passage number was restricted to 6 passages. Apical compartments of HTS 96-well Transwell plates with 0.4 µm microscopically transparent polyester membrane (Corning) were coated with Type 1 Collagen from rat tail (Sigma Aldrich). The HT29-MTX-E12 human cell line was cultured until 70-80% confluent in T-175 tissue culture flasks. Cells were removed with 0.25% Trypsin 2.21 mM EDTA and counted. 30,000 cells were plated onto the apical compartments of pre-coated transwell plates with DMEM culture medium as above and basal reservoirs of transwell plates were filled with the same medium. Cells were cultured in 37° C. and 5% $CO_2$ for 18 days until a confluent monolayer was formed as described previously (Hall et al., *Journal of Pediatric Surgery* 48:353-358 (2013)). Media in the apical compartment and basal reservoir were replaced with new media every two days. One day before the experiment, apical compartment inserts containing the confluent monolayer of HT29-MTX-E12 were transferred to HTS Transwell-96 well receiver plates (Corning). Cells were washed and resuspended with DMEM culture media without antibiotics and basal compartments of the transwell receiver plates were filled with the same.

A working solution of the indicated individual freshly cultured or lyophilized bacteria, consortium or anaerobic PBS control at 10% v/v was added onto the apical compartment of the transwell plates containing confluent HT29-MTX-E12 monolayers. Test articles were centrifuged down to the monolayer at 515×g for four minutes. HT29-MTX-E12 monolayers were co-incubated with test articles for one hour in 37° C. and 5% $CO_2$. 100 ng/ml TNF-α (InvivoGen) was added to the basal compartment of the transwell plate. Trans-epithelial electrical resistance (TEER) across the cell barrier was measured at 0 and 24 hours after addition of TNF-α using the STX100C electrode attached to EVOM2 Volt/Ohm (TEER) Meter (World Precision Instruments).

Example 6.3—Human Macrophage and Monocyte In Vitro Cytokine and Chemokine Assay

The THP-1 human monocyte cell line (ATCC cat #TIB-202) was cultured in 37° C. and 5% $CO_2$ using RPMI 1640 containing 2.05 mM L-glutamine (Corning) supplemented with 10% heat-inactivated FBS (Tissue Culture Biologicals), 100 I·U/mL Penicillin, 100 g/mL Streptomycin and 0.292 mg/mL L-glutamine (Corning). Passage number was restricted to 8 passages. The THP-1 human monocyte cell line was grown until 70-80% confluent. Cells were counted and resuspended in culture media. 100,000 cells were plated per well onto 96 well plates. THP-1 human macrophages were made by culturing the THP-1 human monocyte cells with 10 ng/mL phorbol 12-myristate 13-acetate (PMA) (InvivoGen) for 24 hours followed by 20 ng/mL IL-4 (R&D Systems) and 20 ng/ml IL-13 (R&D Systems) for 48 hours in 37° C. and 5% $CO_2$ as described previously (Genin et al., *BMC Cancer.*15:577 (2015)). One day before the experiment, cells were washed and resuspended in RPMI culture media without antibiotics containing 20 ng/ml IL-4 and 20 ng/ml IL-13.

A working stock solution of the indicated individual freshly cultured or lyophilized bacteria, consortium or anaerobic PBS control was added onto THP-1 macrophages at 10% v/v and centrifuged down onto the THP-1 cells at 515×g for four minutes. 100 ng/ml LPS (InvivoGen) was added at the same time as the test articles. The test articles, LPS and THP-1 macrophages were co-incubated for 24 hours in 37° C. and 5% $CO_2$. THP-1 cell supernatants were collected and analyzed by ELISA. IL-10 and CCL-18 levels in culture supernatants were quantified by using commercial enzyme-linked immunosorbent assay (ELISA) kits from Biolegend or R&D Systems with TMB detection according to manufacturer's specifications.

Example 6.4—Human PBMC In Vitro Cytokine Assay

Trima residual blood product containing concentrated blood mononuclear cells was obtained from anonymous donors through Blood Centers of the Pacific (San Francisco, CA) and processed within 24 hours of collection. Blood samples were tested negative for HIV, HBV. HCV, HTLV, Syphilis, West Nile Virus and Zika Virus. PBMC were isolated using a ficoll gradient as described previously (Sim et al., *J. Vis. Exp.* (112), e54128 (2016)). Briefly, 50 mL of Trima residual was diluted with 50 mL of sterile PBS (Gibco) and 25 mL was overlaid on 15 mL Ficoll-Paque Plus (GE Healthcare) in 50 mL conical tubes. The samples were centrifuged at 450×g for 30 min at room temperature and allowed to stop without brake. The PBMC interphase was collected, washed with PBS and resuspended in RPMI 1640 containing 2.05 mM L-glutamine (Corning) supplemented with 10% heat-inactivated FBS (Tissue Culture Biologicals) and 0.292 mg/mL L-glutamine (Corning). The cells were maintained by incubation in 37° C. and 5% $CO_2$ and used for assay evaluation within 24 h or frozen for later use. Cells were cryopreserved in RPMI 1640 supplemented with 50% FBS and 10% DMSO (Sigma Aldrich) at a concentration of $5\times10^7$ cells/mL and stored in liquid nitrogen until ready for use.

Human PBMC, used immediately after isolation or thawed from cryo-storage, were diluted to $1\times10^6$ cells/mL in RPMI 1640 containing L-glutamine (Corning) supplemented with 10% heat-inactivated FBS (Tissue Culture Biologicals) and 0.292 mg/mL L-glutamine (Corning). A 100 μL aliquot of the $1\times10^6$ cells/mL cell suspension was added to each well within a flat-well 96 well plate and cultured for 24 hours at 37° C. and 5% $CO_2$ before addition of test articles.

Test articles were prepared and added as described for other assays. After 24 hours of incubation in 37° C. with 5% $CO_2$, the plates containing cocultures were centrifuged (515×g; four minutes) and supernatant was collected and analyzed by ELISA as per above.

Example 6.5—Freshly Cultured C1 in HT29-MTX-E12 Human Epithelial Barrier Assay

Figure 4:
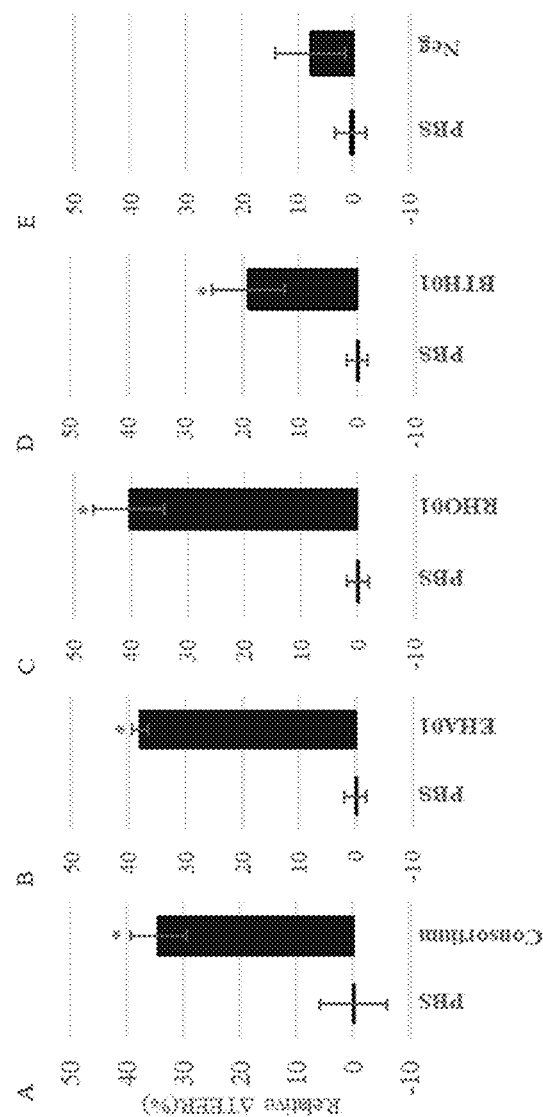
FIGS. 4A-E depicts the effect of freshly cultured C1 bacterial strains and consortium on HT29-MTX-E12 barrier integrity. The % change in TEER (ohms×cm$^2$) between time 0 and 24 hour following basal compartment addition of TNF-α was plotted for 10% v/v of freshly cultured (4A) consortium of BTH01, EHA01 and RHO01, (4B) EHA01, (4C) RHO01, (4D) BTH01 and (4E) an unrelated bacterial strain negative control with no protective effect. The PBS control was set as baseline. Each test article was evaluated in 6 replicates and results are representative of at least two independent experiments. *p value≤0.05 student t-test.

Human ulcerative colitis (UC) patients develop symptoms of increased intestinal permeability which can be reversed by reducing the levels of an inflammatory cytokine TNF-α with anti-TNF-α therapy (Michiclan et al., *Mediators Inflamm.* 2015:628157 (2015)). Finding novel therapeutics that can reduce gut permeability and barrier disruption remains an important goal in developing treatments for colitis. The functional activity of each C1 bacterial strain (BTH01, EHA01 and RHO01) and the consortium of three strains was evaluated on human epithelial cells in the presence of TNF-α, as a model of gut barrier damage and permeability. The confluent HT29-MTX-E12 human epithelial cell line forms a polarized monolayer and produces mucin which are two major characteristics of primary human intestinal epithelial cells (Dolan et al., *PLoS One.* 7 (10): c47300 (2012)). FIG. 4 shows a significant increase in TEER (measurement of cell monolayer integrity) when the three freshly cultured C1 bacterial strains were incubated individually and as a consortium with the HT29-MTX-E12 monolayer in the presence of TNF-α compared to the PBS controls. This indicates that C1 bacterial strains individually and as a consortium can protect human epithelial cells from cytokine-induced barrier damage and can reduce intestinal barrier permeability.

Figure 5:
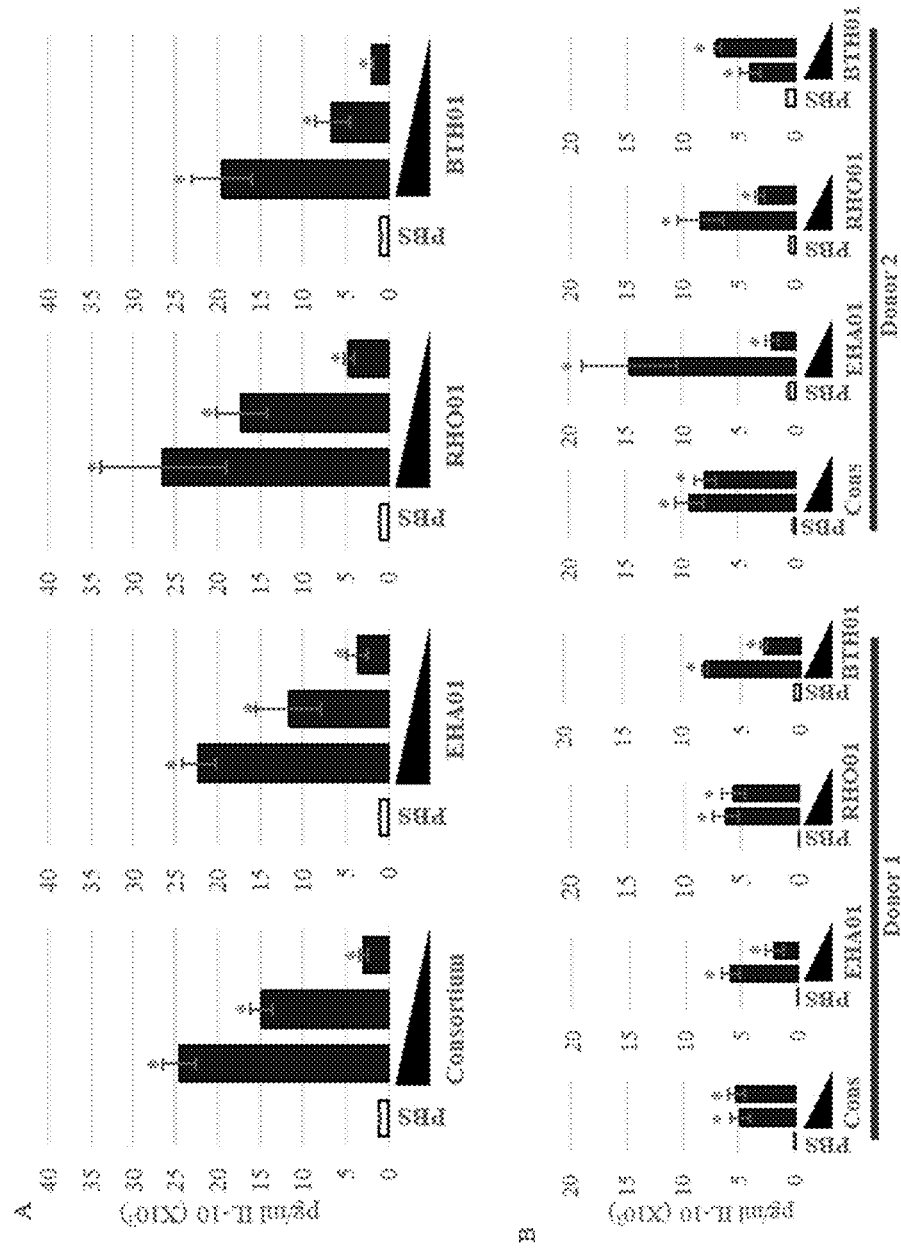
FIG. 5 depicts the effect of freshly cultured C1 bacterial strains and consortium on human THP-1 macrophage and PBMC IL-10 production. THP-1 macrophage supernatants were collected after the assay was completed and (5A) IL-10 concentrations in culture supernatant were plotted for 10%, 3.3% and 1.0% v/v working solution of each individual strain (BTH01, EHA01 and RHO01), the consortium of three strains or PBS (LPS-only) control. Each test article was evaluated in 4 replicates and results are representative of at least two independent experiments. Primary human PBMC supernatants were collected after the assay was completed and (5B) IL-10 concentrations in culture supernatants from PBMC donor 1 and PBMC donor 2 were plotted for 10% or 1% v/v working solution of individual strains or the consortium. Each test article was evaluated in 4 replicates and results are representative of at least two independent experiments. *p value≤0.05 student t-test.

Example 6.6—Freshly Cultured C1 Bacterial Strains and Consortium in Human Macrophage and Monocyte In vitro Cytokine and Chemokine Assay IL-10 is an anti-inflammatory cytokine released by immune cells vital to intestinal homeostasis (Kole et al., *Curr Top Microbiol Immunol.* 380:19-38 (2014)). Mice with genetic deletion of IL-10 (Wilson et al., *PLoS* Pathog. (8): c1002171 (2011)) and humans with IL-10 loss of function mutations (Bisborough et al., *Am J Gastroenterol* Suppl 3:27-37 (2016)) have increased susceptibility to UC development. IL-10-producing intestinal macrophages are protective against infections by the colitis-inducing intestinal pathogen *C. rodentium* (Krause et al., *Nature Communications* 6:7055 (2015)). Therapies targeting mechanisms to increase IL-10 levels have shown promise but lack sufficient efficacy (Li and He, *World J Gastroenterol.* 10 (5): 620-5 (2004)). Improvement in IL-10 promoting therapies remains an attractive strategy for therapeutics against colitis. Each individual bacterial strain and all three together as a consortium were evaluated for the ability to induce IL-10 production by human THP-1 macrophages, in the presence of LPS, and primary human PBMCs. FIG. 5 shows a significant, dose-dependent increase in the production of the anti-inflammatory cytokine IL-10 by (A) THP-1 macrophages and (B) primary human PBMCs induced by each individual freshly cultured bacterial strain or the consortium of three strains. The results indicate that C1 bacterial strains can induce anti-inflammatory IL-10 production in human THP-1 macrophages and primary human monocytes.

Figure 6:
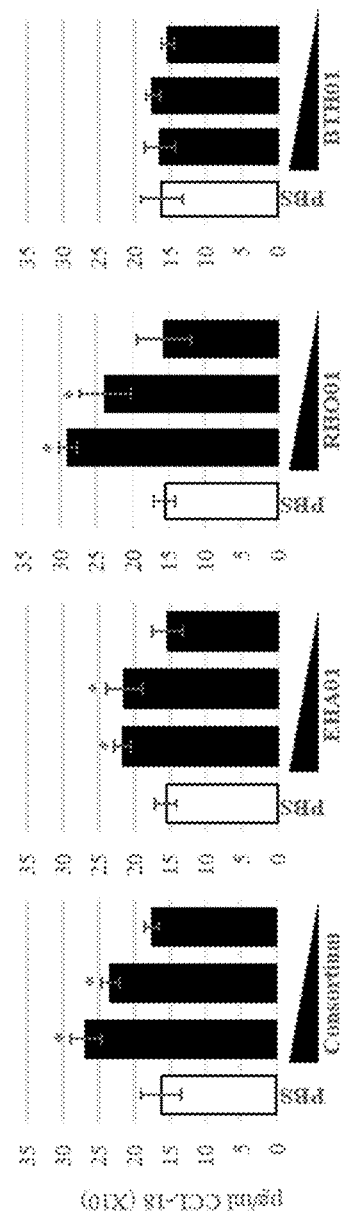
FIG. 6 depicts the effect of freshly cultured C1 bacterial strains and consortium on human THP-1 macrophage CCL-18 production. THP-1 macrophage supernatants were collected after the assay was completed and CCL-18 concentrations in culture supernatant were plotted for 10%, 3.3% and 1.0% v/v working solution of each individual strain (BTH01, EHA01 and RHO01), the consortium of three strains or PBS control. Each test article was evaluated in 4 replicates and results are representative of at least two independent experiments. *p value≤0.05 student t-test.

Each freshly cultured individual C1 bacterial strain or consortium of three strains was evaluated for the ability to induce CCL-18, an M2-macrophage-associated chemokine, by THP-1 macrophages. Induction and polarization of M2 macrophages has previously been reported to be a critical mechanism of protection against inflammatory bowel disease and colonic inflammation (Sco et al., *Sci. Rep* 7 (1): 851 (2017); Steinbach et al., *Inflamm Bowel Dis.* 20 (1): 166-175 (2014)). CCL-18 is a validated marker for M2 macrophages (Genin et al., *BMC Cancer* 15:577 (2015)). FIG. 6 shows a significant, dose-dependent increase in the production of CCL-18 when individual strains EHA01 and RHO01, and the consortium of three strains, EHA01, RHO01 and BTH01 were co-cultured with THP-1 macrophages compared to PBS controls; BTH01 alone did not induce CCL-18. These data indicate that two of three C1 bacterial strains and the consortium can increase the production of CCL-18 from human macrophages which indicates the induction and polarization of anti-inflammatory M2 macrophages.

Example 6.7—Lyophilized C1 in HT29-MTX-E12 Human Epithelial Barrier Assay

Figure 7:
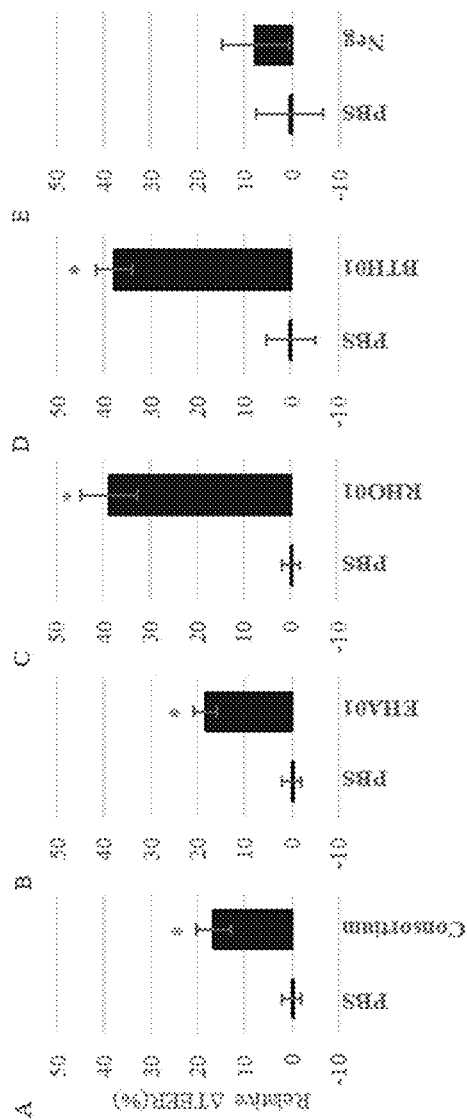
FIG. 7 depicts the effect of lyophilized C1 bacterial strains and consortium on HT29-MTX-E12 barrier integrity. The % change in TEER (ohms×cm$^2$) between time 0 and 24 hour following basal compartment addition of TNF-α was plotted for 10% v/v working solution of lyophilized (7A) consortium of BTH01, EHA01 and RHO01, (7B) EHA01, (7C) RHO01, (7D) BTH01 and (7E) an unrelated bacterial strain negative control with no protective effect. The PBS control was set as baseline. Each test article was evaluated in 6 replicates and results are representative of at least two independent experiments. *p value≤0.05 student t-test.

Results using freshly cultured C1 bacterial strains showed that strains individually and as a consortium can protect human intestinal epithelial cells from TNF-α-induced barrier damage. Since C1 bacterial strains are prepared as a lyophilized drug substance for oral delivery as a therapeutic, the lyophilized forms of C1 bacterial strains were tested to ensure that they retain barrier protective effects. Individual C1 strains were prepared as lyophilized powder using the same methods as used to manufacture C1 drug substances. FIG. 7 shows that individual lyophilized C1 bacterial strains or the consortium of all 3 significantly increased TEER when incubated with the HT29-MTX-E12 monolayer in the presence of TNF-α, compared to the PBS controls. This indicates that a lyophilized form of C1 bacterial strains retains protective effects and reduces intestinal epithelial permeability when tested on human epithelial cells in the presence of TNF-α-induced barrier damage.

Figure 8:
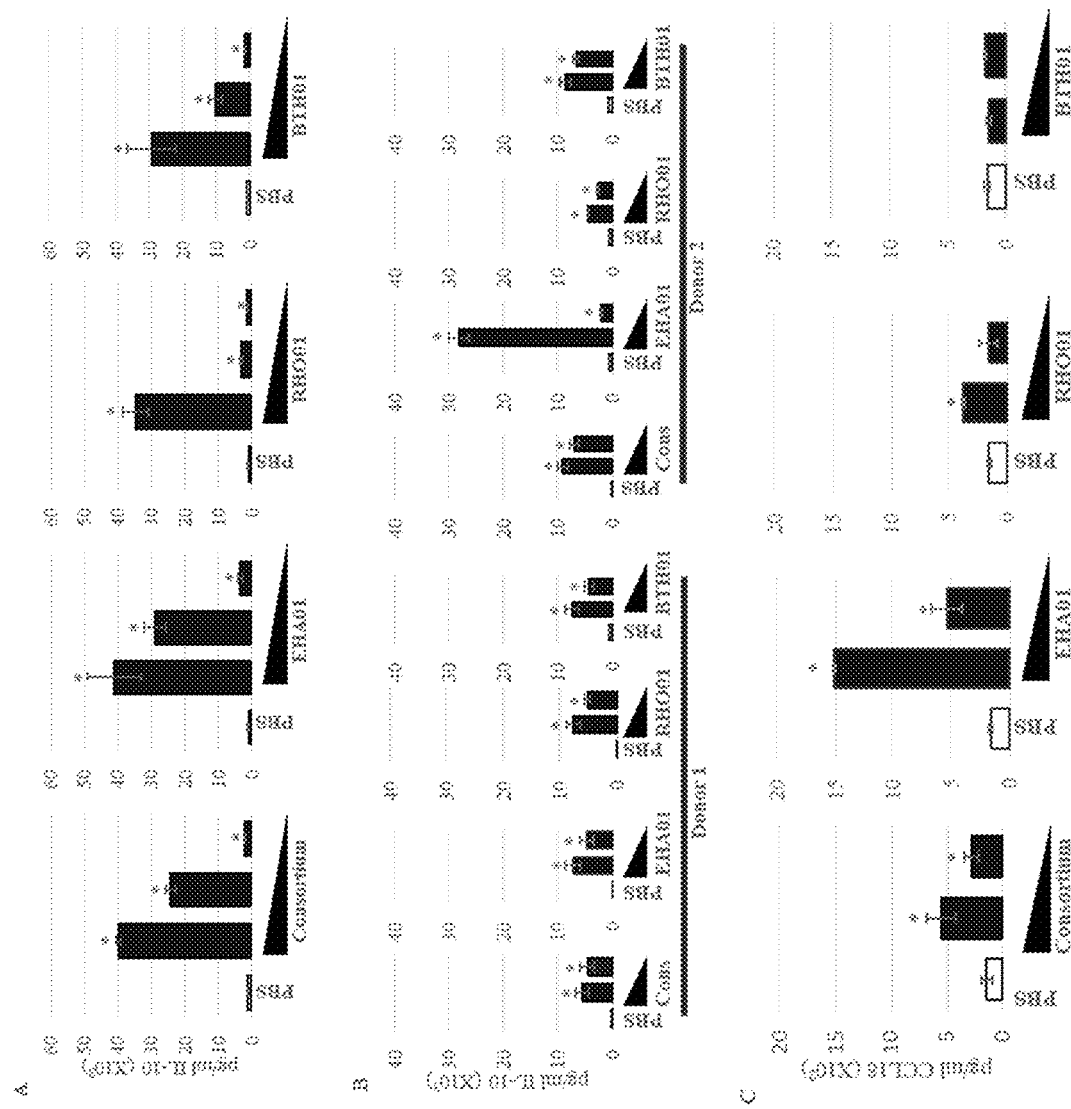
FIGS. 8A-8D depicts the in vitro effects of lyophilized individual C1 bacterial strains or consortium on IL-10 cytokine and CCL-18 chemokine production in THP-1 human macrophage model and IL-10 production in human PBMC model. THP-1 macrophage supernatants were collected at the conclusion of the assay and (8A) IL-10 concentrations in culture supernatant were plotted for 10%, 3.3% and 1.0% v/v working solution of each individual lyophilized strain (BTH01, EHA01 and RHO01), the consortium of three strains or PBS (LPS-only) control. Primary human PBMC supernatants were collected at conclusion of the assay and (8B) IL-10 concentrations in culture supernatants from PBMC donor 1 and PBMC donor 2 were plotted for 10% or 1% v/v working solution of individual lyophilized strains or the consortium. THP-1 macrophage supernatants were collected at conclusion of the assay and (8C) CCL-18 concentrations in culture supernatant were plotted for 10% and 1.0% v/v working solution of each individual lyophilized strain (BTH01, EHA01 and RHO01), the consortium of three strains or PBS control. Each test article was evaluated in 4 replicates and results are representative of at least two independent experiments.

Example 6.8—Lyophilized C1 Bacterial Strains in Human Macrophage and Monocyte In vitro Cytokine and Chemokine Assays Similar to the results in the human intestinal epithelial barrier assay, the lyophilized forms of C1 individual strains and all three together as a consortium retained the ability to induce the anti-inflammatory cytokine IL-10 and M2 macrophage-associated chemokine CCL-18 in human THP-1 macrophages (FIG. 8A, IL-10 and FIG. 8C, CCL-18). The lyophilized forms of C1 also retained the ability to induce IL-10 in primary human PBMC (FIG. 8B).

Example 6.9—UC Fecal Microflora in HT29-MTX-E12 Human Epithelial Barrier In vitro Assay and in Human THP-1 Macrophage In vitro Cytokine Assay Aliquots of glycerol stocks including 50% glycerol: 50% UC fecal sample were prepared. A working stock solution was prepared by thawing a glycerol stocks on the day of the experiment in anaerobic conditions, followed by washing and resuspending with pre-reduced anaerobic PBS to the optical density of OD600-0.3 (~$10^8$ CFU/ml). This working stock solution of the UC microflora was added to the apical compartment of transwell plates containing confluent HT29-MTX-E12 monolayers (10% v/v) along with either working stock solutions of freshly cultured C1 consortium (10% v/v), or anaerobic PBS control (10% v/v). The TEER assay was conducted as described, without added TNFα. Similarly, the UC microflora working stock solution was added to THP-1 macrophages (10% v/v), with or without freshly cultured C1 consortium working stock solution (10% v/v) or anaerobic PBS control. After four hours of co-incubation in 37° C. and 5% $CO_2$, THP-1 macrophages were washed and resuspended with RPMI culture media supplemented with Pen/Strep to remove excess bacteria. THP-1 macrophages were incubated for 24 hours in 37° C. and 5% $CO_2$. THP-1 cell supernatants were collected and analyzed for IL-10 using ELISA.

Figure 9:
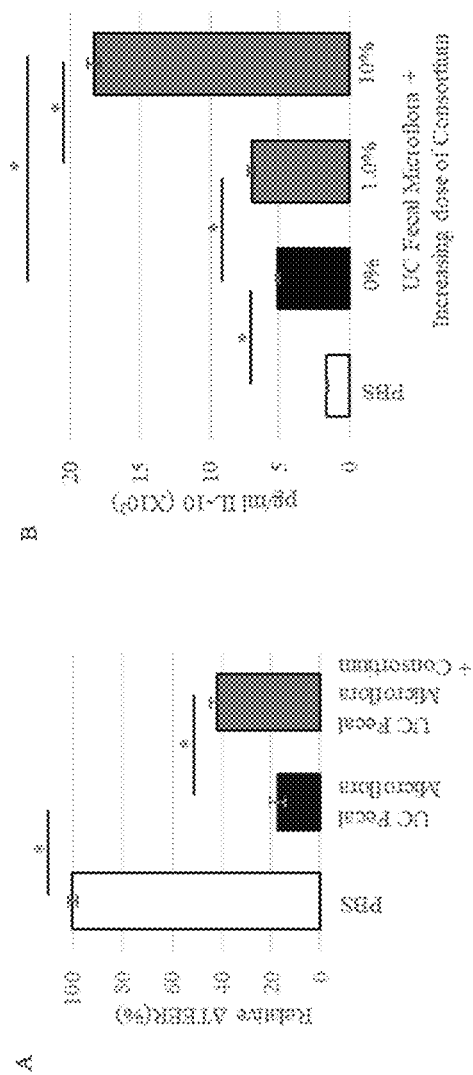
FIGS. 9A-9B depicts the effect of freshly cultured C1 consortium in HT29-MTX-E12 human epithelial barrier in vitro assay and in human THP-1 macrophage in vitro cytokine assay in the presence of UC fecal microflora. (9A) The % change in TEER (ohms×cm$^2$) between time 0 and 24 hour are plotted for the indicated test articles. The PBS control was set as the relative maximum. Each test article was evaluated in 6 replicates and results are representative of at least two independent experiments. (9B) THP-1 macrophage supernatants were collected at the end of the assay and IL-10 concentrations in culture supernatant were plotted for the PBS control, UC fecal microflora added with the indicated v/v amount of C1 consortium. Each test article was evaluated in 4 replicates and results are representative of at least two independent experiments. * p value≤0.05 student t-test.

The C1 consortium was tested for ability to protect against barrier damage induced by UC fecal microflora in the HT29-MTX-E12 human intestinal epithelial barrier assay. FIG. 9A demonstrates that addition of the UC fecal microflora alone reduced the TEER of the HT29-MTX-E12 monolayer suggesting that microbes in the UC fecal microflora can damage the monolayer and increase its permeability. When the HT29-MTX-E12 monolayer was co-incubated with the UC fecal microflora and freshly cultured C1 consortium, the reduction in TEER by the UC fecal microflora is significantly inhibited (FIG. 9A). This indicates that the C1 consortium can protect human intestinal epithelial cells from UC fecal microflora induced damage and reduce barrier permeability.

The C1 consortium was tested for ability to induce the anti-inflammatory cytokine IL-10 in THP-1 macrophages in the presence of UC fecal microflora. FIG. 9B shows that UC fecal microflora alone can induce IL-10 from THP-1 macrophages, but addition of C1 consortium significantly enhanced IL-10 production which was dose-dependent. This indicates that the C1 consortium can increase the induction of IL-10 in human macrophages in the presence of a UC microflora.

Example 6.10—C1 Bacterial Strains in Human Macrophage Autophagy and IL-10 Assays Autophagy is an intracellular process whereby unwanted or damaged cytoplasmic constituents (such as proteins and organelles) are degraded within lysosomes (Doria et al., *N Engl J Med* 368 (19): 1845 (2013)). This process plays an important role in innate and adaptive immunity and maintenance of homeostasis, and acts as a defense mechanism against invading pathogens. Autophagy dysfunction can have various pathological consequences, including tumor progression, pathogen hyper-virulence, and neurodegeneration, and has been suggested to be associated with the pathogenesis of several autoimmune and inflammatory disorders, such as systemic lupus erythematosus, psoriasis, rheumatoid arthritis, inflammatory bowel disease, and multiple sclerosis (Yin et al., *Front Immunol.* 2018; 9:1512 (2018)). The inhibition of autophagy accelerates the progress of some inflammatory and autoimmune diseases via promotion of inflammatory cytokine production (Yin et al., 2018). Modulation of autophagy has shown promise in the treatment of Crohn's disease (Nys et al., *Nat Rev Gastroenterol Hepatol.* (7): 395-401 (2013)), and several approved treatments for Crohn's disease act through the induction of autophagy, including 5-ASA (mesalamine/suffasalazine; see Wu et al., *PLoS ONE* 7: e37572 (2012); and Fiorucci et al., *Br. J. Pharmacol.* 150:996-1002 (2007)); and anti-TNF-α (Infliximab, Adalimumab, Certolizumab pegol; see Nys et al., 2013). C1 bacterial strains, EHA01, RHO01 and BTH01, were tested individually, in pair-wise combinations and together in a single consortium for the ability to induce autophagy as well as production of IL-10 in human THP-1 macrophages.

For assessing autophagy, M2 macrophages were prepared as follows. The THP-1 human monocyte cell line (ATCC cat #TIB-202) was cultured in 37° C. and 5% $CO_2$ using RPMI 1640 containing 2.05 mM L-glutamine (Corning) supplemented with 10% heat-inactivated FBS (Tissue Culture Biologicals), 100 I·U/mL Penicillin, 100 μg/mL Streptomycin and 0.292 mg/mL L-glutamine (Corning). Passage number was restricted to 8 passages. The THP-1 human monocyte cell line was grown until 70-80% confluent. Cells were counted and resuspended in culture media. 100,000 cells were plated per well onto 96 well plates. THP-1 human macrophages were made by culturing the THP-1 human monocyte cells with 10 ng/ml phorbol 12-myristate 13-acetate (PMA) (InvivoGen) for 24 hours, washed then incubated with RPMI with 20 ng/ml IL-4 (R&D Systems) and 20 ng/ml IL-13 (R&D Systems) for 48 hours in 37° C. and 5% $CO_2$ as described previously (Genin et al., *BMC Cancer* 15:577 (2015)).

For assessing IL-10, M1 macrophages were prepared as follows. The THP-1 human monocyte cell line (ATCC cat #TIB-202) was cultured in 37° C. and 5% $CO_2$ using RPMI 1640 containing 2.05 mM L-glutamine (Corning) supplemented with 10% heat-inactivated FBS (Tissue Culture Biologicals), 100 I·U/mL Penicillin, 100 μg/mL Streptomycin and 0.292 mg/mL L-glutamine (Corning). Passage number was restricted to 8 passages. The THP-1 human monocyte cell line was grown until 70-80% confluent. Cells were counted and resuspended in culture media. 100,000 cells were plated per well onto 96 well plates. THP-1 human macrophages were made by culturing the THP-1 human monocyte cells with 10 ng/ml phorbol 12-myristate 13-acetate (PMA) (InvivoGen) for 24 hours, washed then incubated with RPMI without antibiotics for 48 hours in 37° C. and 5% $CO_2$.

For both the autophagy and IL-10 assays, working stock solutions of individual freshly cultured or frozen bacteria (100% of EHA01, RHO01 or BTH01), consortia (1:1 for a 2-strain consortium (EHA01: RHO01; RHO01: BTH01; and EHA01: BTH01) and 1:1:1 for the 3-strain consortium (EHA01: RHO01: BTH01)) and anaerobic PBS control, respectively, were prepared, and each working stock of bacteria was normalized by surface area to $10^8$ μm²/ml using a Coulter Counter. Each test article was added onto THP-1 macrophages at 10% v/v and centrifuged down onto the THP-1 cells at 515×g for four minutes. 500 ng/ml LPS (InvivoGen) was added at the same time as the test articles. The test articles, LPS and THP-1 macrophages were co-incubated for 3 hours in 37° C. and 5% $CO_2$. The co-culture media was replaced with fresh RPMI with 100 I·U/mL Penicillin, 100 μg/mL Streptomycin. The cells were incubated overnight in 37° C. and 5% $CO_2$. M1 macrophage supernatants were collected and analyzed by ELISA. IL-10 in culture supernatants were quantified by using commercial enzyme-linked immunosorbent assay (ELISA) kits from Biolegend or R&D Systems with TMB detection according to manufacturer's specifications. M2 macrophage cells were lifted, processed and analyzed for autophagy levels using the CYTO-ID® Autophagy Detection Kit (Enzo).

To perform comparisons of the amount of autophagy or IL-10 production induced by a consortium to the total induction by each single strain of the consortium acting individually, assay values for the single strain test articles were normalized for biomass, since these test articles contained roughly two times (2×) or three times (3×) more biomass of a particular strain relative to that in a two-strain or three-strain consortium, respectively. Biomass normalizations were performed as follows. For purposes of comparisons to 2-strain consortia, assay values for each of the two corresponding single strain test articles were added and divided by two (i.e., averaged). For purposes of comparisons to 3-strain consortia, assay values for each of the three corresponding single strain test articles were added and divided by three (i.e., averaged). The assay value for each consortium was then compared to its corresponding single strain average (see "% increase (consortium vs single strain average)" in Tables 4 and 5).

Figure 10:
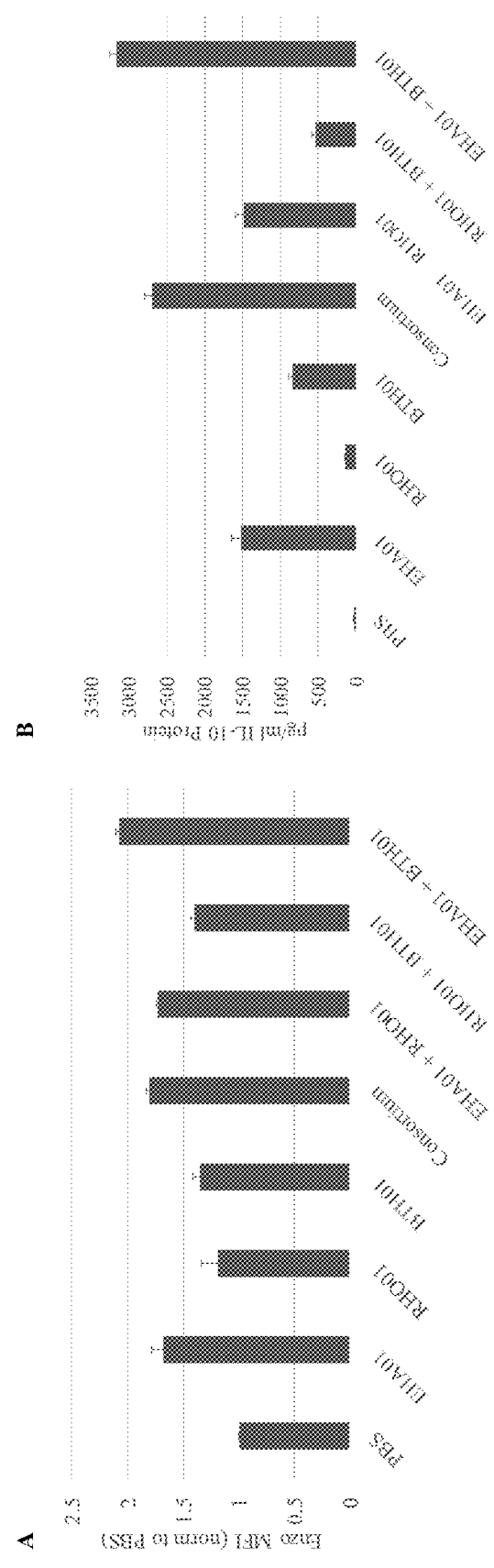
FIGS. 10A-10B depicts the in vitro effects of individual C1 bacterial strains or consortia (2-strain and 3-strain) on induction of autophagy and IL-10 cytokine production in a THP-1 human macrophage model. Following incubation with 10% v/v working solution of each test article, THP-1 human macrophage cells and supernatants were collected, processed and analyzed. (10A) Mean fluorescence intensity (MFI) corresponding to degree of autophagy induction in THP-1 M2 macrophages is shown for each individual lyophilized strain (EHA01, RHO01 and BTH01), pairwise combinations of the three strains (EHA01+RHO01, RHO01+BTH01 and EHA01+BTH01), the consortium of three strains together, or PBS (LPS-only) control. The PBS control was set as baseline. Each test article was evaluated in 4 replicates and results are representative of at least two independent experiments. (10B) IL-10 concentrations in culture supernatant from THP-1 M1 macrophages are shown for each individual lyophilized strain (EHA01, RHO01 and BTH01), pairwise combinations of the three strains (EHA01+RHO01, RHO01+BTH01 and EHA01+BTH01), the consortium of three strains together, or PBS (LPS-only) control. Each test article was evaluated in 4 replicates and results are representative of at least two independent experiments.

As shown in FIG. 10A and presented in tabular form below, autophagy was induced in THP-1 macrophages by the addition of EHA01, RHO01 and BTH01 strains individually (Table 4A); each pairwise combination of the three strains (EHA01+RHO01 in Table 4B; RHO01+BTH01 in Table 4C; and EHA01+BTH01 in Table 4D); and a consortium of all three strains combined (EHA01+RHO01+BTH01 in Table 4A), relative to the addition of PBS. Notably, each pairwise combination as well as the three-strain combination induced autophagy to a greater degree as a consortium, compared to the combined induction of each respective member strain individually, normalized for biomass (see "% increase (consortium vs single strain average)" in Tables 4A-D).

TABLE 4A

Induction of autophagy with 3-strain consortium:
*E. hallii* + *R. hominis* + *B. thetaiotaomicron*

| Test article | Enzo MFI (avg) |
|---|---|
| PBS | 1.00 |
| 100% EHA01 | 1.68 |
| 100% RHO01 | 1.19 |
| 100% BTH01 | 1.35 |
| 3-strain consortium: | 1.81 |
| 33% EHA01, 33% RHO01, 33% BTH01 | |
| single strain average (normalization for biomass) | 1.41 |
| % increase (consortium vs single strain avg.) | 28.68 |

TABLE 4B

Induction of autophagy with 2-strain consortium:
*E. hallii* + *R. hominis*

| Test article | Enzo MFI (avg) |
|---|---|
| PBS | 1.00 |
| 100% EHA01 | 1.68 |
| 100% RHO01 | 1.19 |
| 2-strain consortium: | 1.73 |
| 50% EHA01, 50% RHO01 | |
| single strain average (normalization for biomass) | 1.43 |
| % increase (consortium vs single strain avg.) | 20.61 |

TABLE 4C

Induction of autophagy with 2-strain consortium:
R. hominis + B. thetaiotaomicron

| Test article | Enzo MFI (avg) |
|---|---|
| PBS | 1.00 |
| 100% RHO01 | 1.19 |
| 100% BTH01 | 1.35 |
| 2-strain consortium: 50% RHO01, 50% BTH01 | 1.40 |
| single strain average (normalization for biomass) | 1.27 |
| % increase (consortium vs single strain avg.) | 10.24 |

TABLE 4D

Induction of autophagy with 2-strain consortium:
E. hallii + B. thetaiotaomicron

| Test article | Enzo MFI (avg) |
|---|---|
| PBS | 1.00 |
| 100% EHA01 | 1.68 |
| 100% BTH01 | 1.35 |
| 2-strain consortium: 50% EHA01, 50% BTH01 | 2.08 |
| single strain average (normalization for biomass) | 1.52 |
| % increase (consortium vs single strain avg.) | 36.99 |

As shown in FIG. 10B and presented in tabular form below, production of IL-10 was also induced in THP-1 macrophages by the addition of EHA01, RHO01 and BTH01 strains individually (Table 5A); each pairwise combination of the three strains (EHA01+RHO01 in Table 5B; RHO01+BTH01 in Table 5C; and EHA01+BTH01 in Table 5D); and a consortium of all three strains combined (EHA01+RHO01+BTH01 in Table 5A), relative to the addition of PBS. Similar to the results seen for induction of autophagy, each pairwise combination as well as the three-strain combination induced IL-10 production to a greater degree as a consortium, compared to the combined induction of each respective member strain individually, normalized for biomass (see "% increase (consortium vs single strain average)" in Tables 5A-D).

TABLE 5A

Induction of IL-10 with 3-strain consortium:
E. hallii + R. hominis + B. thetaiotaomicron

| Test article | pg/ml IL-10 protein (avg) |
|---|---|
| PBS | 1.00 |
| 100% EHA01 | 1517.12 |
| 100% RHO01 | 147.85 |
| 100% BTH01 | 835.33 |
| 3-strain consortium: 33% EHA01, 33% RHO01, 33% BTH01 | 2692.00 |
| single strain average (normalization for biomass) | 833.43 |
| % increase (consortium vs single strain avg.) | 223.00 |

TABLE 5B

Induction of IL-10 with 2-strain consortium: E. hallii + R. hominis

| Test article | pg/ml IL-10 protein (avg) |
|---|---|
| PBS | 1.00 |
| 100% EHA01 | 1517.12 |
| 100% RHO01 | 147.85 |
| 2-strain consortium: 50% EHA01, 50% RHO01 | 1484.24 |
| single strain average (normalization for biomass) | 832.48 |
| % increase (consortium vs single strain avg.) | 78.29 |

TABLE 5C

Induction of IL-10 with 2-strain consortium:
R. hominis + B. thetaiotaomicron

| Test article | pg/ml IL-10 protein (avg) |
|---|---|
| PBS | 1.00 |
| 100% RHO01 | 147.85 |
| 100% BTH01 | 835.33 |
| 2-strain consortium: 50% RHO01, 50% BTH01 | 532.66 |
| single strain average (normalization for biomass) | 491.59 |
| % increase (consortium vs single strain avg.) | 8.36 |

TABLE 5D

Induction of IL-10 with 2-strain consortium:
E. hallii + B. thetaiotaomicron

| Test article | pg/ml IL-10 protein (avg) |
|---|---|
| PBS | 1.00 |
| 100% EHA01 | 1517.12 |
| 100% BTH01 | 835.33 |
| 2-strain consortium: 50% EHA01, 50% BTH01 | 3160.89 |
| single strain average (normalization for biomass) | 1176.22 |
| % increase (consortium vs single strain avg.) | 168.73 |

These results demonstrate the ability of each C1 bacterial strain to individually induce autophagy and IL-10 production in THP-1 macrophages. Additionally, the unexpected increase in these inductions observed for each two-strain and three-strain consortia, compared to the combined inductions of each member strain individually, indicates that EHA01, RHO01 and BTH01 interact synergistically within these consortia to effect their biological activities.

Figure 11:
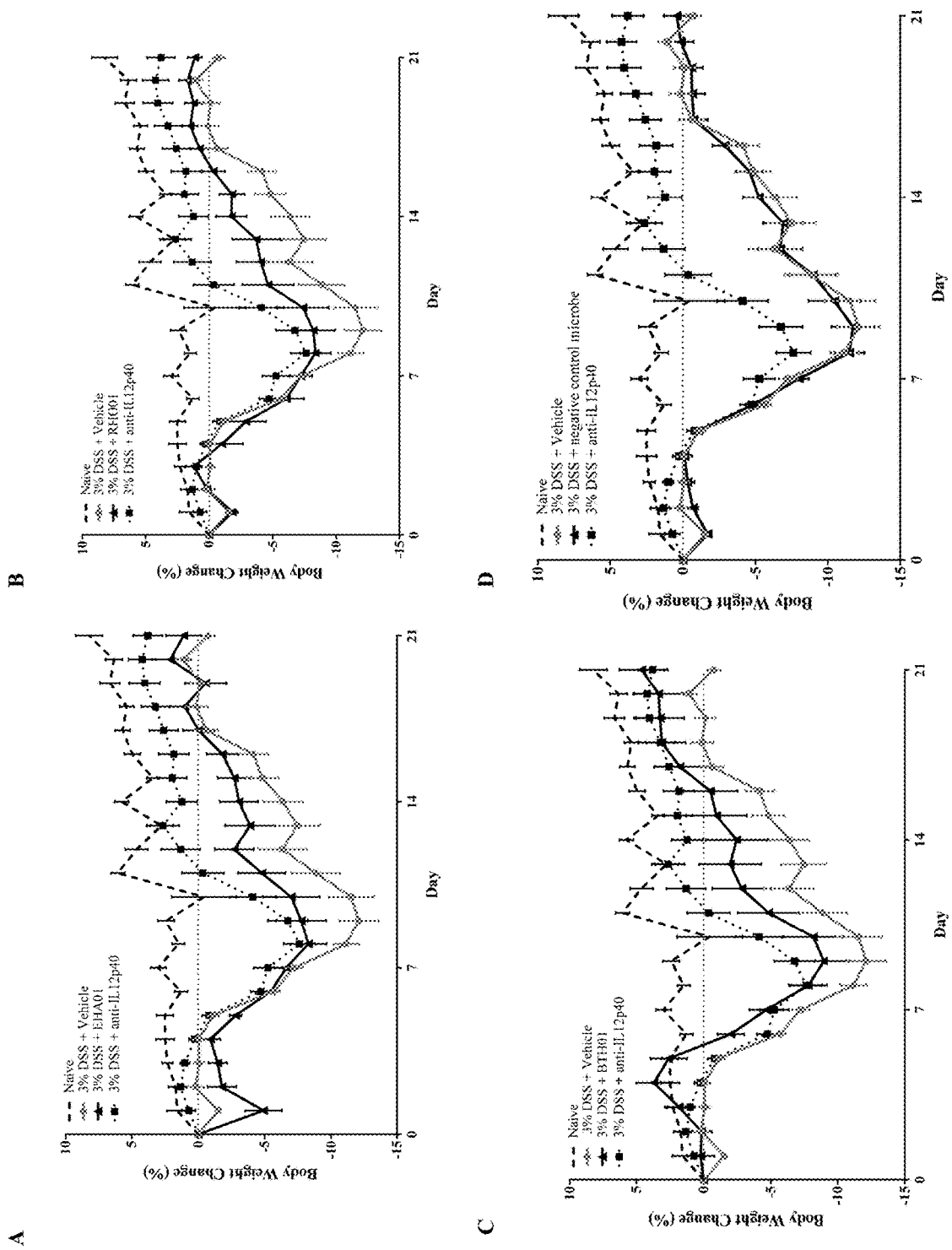
FIGS. 11A-11D depicts the effect of C1 individual bacterial strains on percent body weight change in a DSS-induced colitis mouse model. Groups of mice for naïve (N=5), test articles (N=12) and vehicle control (N=20) were used in a standard DSS-induced colitis model. Mice were treated with 3% DSS from days 0-5. Groups of mice were treated from days-1-21 daily with an oral dose at 1×10$^9$ VCC of each of the three C1 bacterial strains or with a negative control bacterial strain that did not show in vitro activity. Groups of mice were administered PBS as a vehicle control or an antibody against IL-12p40 (Q3D IP) as a positive control for efficacy. A plot of daily body weight change over time (d0-21) for each test group is shown alongside naïve mice (dashed black), vehicle control (grey, circle) and anti-IL-12p40 (dotted black, square). (11A) EHA01, (11B) RHO01, (11C) BTH01, and (11D) negative control microbe. Error bars are shown as SEM.

Example 6.11—Individual C1 Bacterial Strains Reduce Disease Severity in DSS-induced Colitis Model C1 bacterial strains, EHA01, RHO01 and BTH01 in lyophilized form, were tested individually in a well-validated DSS-induced colitis mouse model (Chassaing et al., Curr Protoc Immunol.; 104: Unit 15.25 (2014)) to evaluate efficacy under conditions of chemically-induced intestinal damage. Mice were treated with 3% DSS in drinking water for 5 days to induce gut mucosal damage followed by DSS removal for the remainder of the 21-day study. A daily dose of $1 \times 10^9$ VCC of lyophilized bacterial strain resuspended in PBS was administered by oral gavage throughout the 21-day study duration (FIG. 11). An antibody against IL-12p40 was administered parenterally as a positive control for efficacy.

Three efficacy endpoints were evaluated: body weight-loss over time, colitis severity score and stool consistency score measured by endoscopy at day 12 and day 21 of the study. Each of the three individual C1 strains and the anti-IL-12p40 antibody led to a reduction in DSS-induced body weight-loss compared to the vehicle control, whereas a microbe with no activity in promoting the intestinal barrier in vitro did not (FIG. 11A-D, Table 6). Similar effects of the three C1 strains and the anti-IL-12p40 positive control were observed on colitis severity score and stool consistency score (Table 8).

Example 6.11.1—Individual C1 Bacterial Strains Protect Against Weight Loss in DSS-induced Colitis Model All groups administered the three C1 bacterial strains, EHA01, RHO01 and BTH01 demonstrated marked improvement in weight loss compared to vehicle and negative microbe controls (FIG. 11A-C). These differences in weight loss severity are most notably seen on days 7-16 which mark the peak of intestinal damage and recovery period within the colitis model. At day 21, animals administered test article BTH01 recovered weight similar to the benchmark positive control group given anti-IL-12p40 (FIG. 11C). The negative control microbe did not demonstrate any positive effect on weight loss compared to vehicle control (FIG. 11D). These observations are also reflected in the quantified AUC which sums the weight percent change from Day 0 of the study (Table 6). The protection conferred by the individual strains reached statistical significance on several days between day 8 to 21.

TABLE 6

Evaluation of Weight Change Area Under the Curve in DSS Colitis Model

| Test Group | Weight Change Mean AUC |
|---|---|
| Naïve | 74.03 ± 11.4 |
| 3% DSS + Vehicle | −88.11 ± 16.64 |
| 3% DSS + EHA01 | −62.20 ± 16.42 |
| 3% DSS + RHO01 | −52.07 ± 16.42 |
| 3% DSS + BTH01 | −22.6 ± 29.8 |
| 3% DSS + Negative control microbe | −87.38 ± 16.42 |
| 3% DSS + Anti-IL-12p40 | −1.348 ± 18.66 |

AUC was calculated using Prism's area under the curve algorithm which applies the trapezoid rule to a nonlinear regression of % weight change. Error is represented as SEM.

The full compilation of daily weight loss percentage and statistics for each test group is depicted in Table 7, which shows mean weight loss percent±SEM by day of individual test articles (N=12), vehicle negative control (N=20) and Anti-IL-12p40 positive control (N=12). Q value≤0.05 is considered statistically significant using the Kruskal-Wallis test to concurrently compare all test articles included in table to the vehicle control with Two-stage step-up method of Bejamini, Keieger and Yekutieli to correct for multiple comparison by controlling False Discovery Rate. Results were similar when analyzed using the one-way ANOVA test.

TABLE 7

Mean Weight Loss Percent and Statistical Analysis from DSS-induced Colitis Study

| | Vehicle | EHA01 | | RHO01 | | BTH01 | | Anti-IL-12p40 | |
|---|---|---|---|---|---|---|---|---|---|
| Days | Mean | Mean | Q value | Mean | Q value | Mean | Q value | Mean | Q value |
| 0 | 0 ± 0.0 | 0 ± 0.0 | NA | 0 ± 0.0 | NA | 0 ± 0.0 | NA | 0 ± 0.0 | NA |
| 1 | −2 ± .19 | −5 ± 1.4 | 0.0224 | −2 ± .42 | 0.3444 | 0.2 ± 1.0 | 0.0561 | 0.7 ± .51 | 0.0108 |
| 2 | 0.2 ± .63 | −2 ± 1.1 | 0.4073 | 0.2 ± .34 | 0.6396 | 0.2 ± .78 | 0.6396 | 1 ± .46 | 0.4672 |
| 3 | −0.1 ± .36 | −1.5 ± .71 | 0.1732 | 1 ± .64 | 0.1732 | 2 ± 1.1 | 0.1700 | 1 ± .35 | 0.1700 |
| 4 | 0.0 ± .45 | −0.9 ± .73 | 0.9862 | −1 ± 1.7 | 0.9862 | 4 ± 1.3 | 0.0826 | .3 ± .43 | 0.9862 |
| 5 | −1 ± .40 | −3 ± .46 | 0.0747 | −3 ± 1.6 | 0.4865 | 3 ± 1.4 | 0.0747 | −0.8 ± .51 | 0.8386 |
| 6 | −6 ± .43 | −5 ± .68 | 0.7672 | −6 ± 1.4 | 0.7672 | −2 ± .99 | 0.0172 | −5 ± .78 | 0.7335 |
| 7 | −7 ± .65 | −7 ± .88 | >0.9999 | −7 ± .89 | >0.9999 | −5 ± 1.3 | 0.0753 | −5 ± 1.1 | 0.1791 |
| 8 | −11 ± 10 | −8 ± 1.4 | 0.1043 | −8 ± 1.2 | 0.1043 | 8 ± 1.4 | 0.0797 | −8 ± 1.2 | 0.0797 |
| 9 | −12 ± 1.5 | −8 ± 1.9 | 0.1364 | −8 ± 1.7 | 0.1364 | −9 ± 1.9 | 0.2034 | 7 ± 1.5 | 0.1364 |
| 10 | −12 ± 1.7 | −7 ± 2.1 | 0.1899 | −7 ± 2.0 | 0.1899 | −8 ± 2.2 | 0.2425 | −4 ± 1.7 | 0.0590 |
| 11 | −9 ± 1.9 | −5 ± 1.8 | 0.1634 | −5 ± 2.0 | 0.1634 | −5 ± 2.3 | 0.1634 | −0.4 ± 1.6 | 0.0084 |
| 12 | −6 ± 1.8 | 3 ± 1.5 | 0.3948 | −4 ± 1.9 | 0.5028 | −3 ± 2.2 | 0.3948 | 1 ± 1.5 | 0.0188 |
| 13 | −7 ± 1.7 | −4 ± 1.9 | 0.2242 | −4 ± 1.9 | 0.2242 | −2 ± 1.3 | 0.1069 | 3 ± 1.2 | 0.0005 |
| 14 | −6 ± 1.5 | −3 ± 1.4 | 0.2440 | −2 ± 1.2 | 0.1502 | −2 ± 2.3 | 0.1593 | 1 ± 1.2 | 0.0049 |
| 15 | −5 ± 1.2 | −3 ± 1.3 | 0.3843 | −2 ± 1.0 | 0.2269 | −0.9 ± 2.3 | 0.1986 | 2 ± 1.1 | 0.0015 |
| 16 | −4 ± 1.1 | −2 ± 1.2 | 0.3126 | −0.3 ± .90 | 0.0716 | −0.5 ± 2.0 | 0.2083 | 2 ± 1.1 | 0.0015 |
| 17 | −0.1 ± .86 | −0.0 ± 1.2 | 0.9912 | 0.8 ± .68 | 0.9812 | 2 ± 1.9 | 0.9812 | 2.6 ± 1.1 | 0.1336 |
| 18 | 0.1 ± .83 | 1 ± 1.1 | 0.7923 | 1 ± .61 | 0.7923 | 3 ± 1.8 | 0.7923 | 3 ± 1.1 | 0.2250 |
| 19 | −4 ± .93 | −3 ± .63 | 0.3149 | −2 ± .72 | 0.1610 | −1 ± .85 | 0.0145 | 0.0 ± .74 | 0.0008 |
| 20 | 1 ± .57 | 2 ± 1.3 | 0.8091 | 2 ± .68 | 0.8091 | 3 ± 1.8 | 0.8091 | 4 ± 1.0 | 0.0549 |
| 21 | −0.8 ± .50 | 1 ± 1.3 | 0.0544 | 1 ± .57 | 0.0551 | 5 ± 1.7 | 0.0007 | 4 ± 1.1 | 0.0002 |

Example 6.11.2—C1 Bacterial Strains Improve Endoscopy Colitis Score and Stool Consistency in DSS-induced Colitis Model On Days 12 and 21, endoscopy was performed on all groups to assess colitis severity and stool consistency, which are markers of intestinal inflammation. Colitis severity was scored using a 0-4 scale (0=normal; 1=loss of vascularity; 2=loss of vascularity and friability; 3=friability and erosions; 4=ulcerations and bleeding). Additionally, stool consistency was scored during endoscopy using the parameters defined in Table 8.

TABLE 8

Stool Consistency

| Score | Description |
|---|---|
| 0 | Normal, well-formed pellet |
| 1 | Loose stool, soft, staying in shape |
| 2 | Loose stool, abnormal form with excess moisture |
| 3 | Watery or diarrhea |
| 4 | Bloody diarrhea |

As shown in Table 9, mean endoscopy scores were reduced in animals administered EHA01 and RHO01 on Day 12 and in all animals administered test articles on Day 21 relative to the vehicle control. Mean stool consistency scores were also reduced in animals administered EHA01 and RHO01 on Day 12 and in all animals administered test articles on Day 21 as compared to those treated with vehicle control.

TABLE 9

Summary of Effects of C1 Strains and Controls on Endoscopy Score and Stool Consistency Measured on Day 12 and Day 21 of Study

| Test Group | Mean Endoscopy Score at Day 12 | Stool Consistency Score at Day 12 | Mean Endoscopy Score at Day 21 | Stool Consistency Score at Day 21 |
|---|---|---|---|---|
| Naïve | 0 ± 0 | 0 ± 0 | 0 ± 0 | 0 ± 0 |
| Vehicle | 2.20 ± 0.16 | 2.0 ± 0.15 | 2.05 ± 0.15 | 1.44 ± 0.2 |
| EHA01 | 1.92 ± 0.15 | 1.33 ± 0.24 | 1.82 ± 0.18 | 0.90 ± 0.10 |
| RHO01 | 1.75 ± 0.18 | 1.58 ± 0.23 | 1.33 ± 0.14 | 0.75 ± 0.18 |
| BTH01 | 2.08 ± 0.08 | 2.1 ± 0.23 | 1.67 ± 0.19 | 1.17 ± 0.21 |
| Negative Control Microbe | 2.25 ± 0.13 | 2.1 ± 0.18 | 1.75 ± 0.18 | 1.18 ± 0.18 |
| Anti-IL-12p40 | 1.92 ± 0.15 | 1.36 ± 0.24 | 1.75 ± 0.18 | 0.58 ± 0.15 |

Stool consistency and colitis severity was scored as described. Error is represented as SEM.

Figure 12:
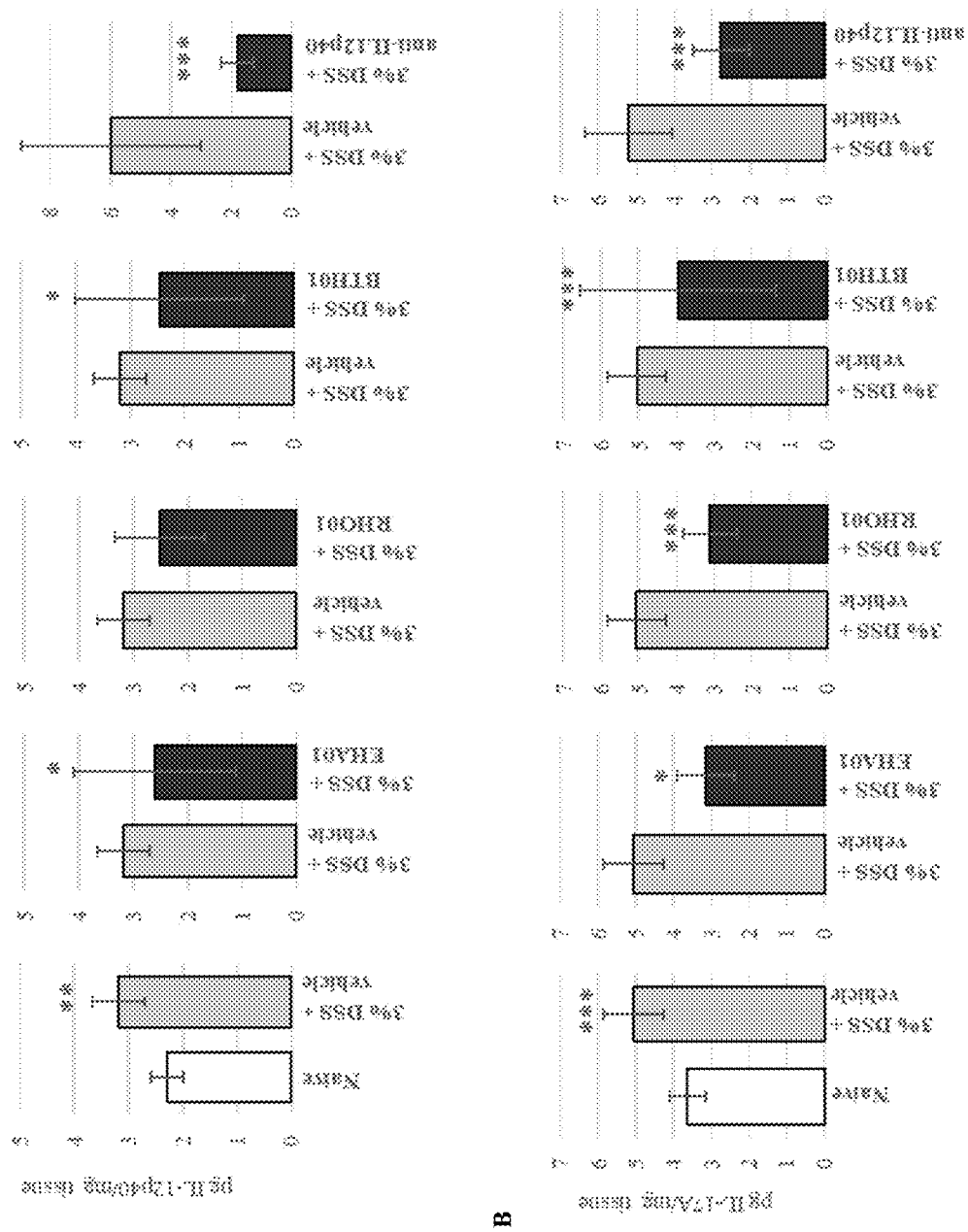
FIGS. 12A-12B depicts cytokine levels in colon tissue on Day 21 of DSS-induced colitis. Cytokine levels were evaluated by ELISA after colon tissue homogenization in lysis buffer. Levels were normalized to mg of tissue analyzed. Each test article was evaluated in N=12 animals. *p value≤0.05; p value≤0.001; *p value≤0.005; Mann-Whitney non-parametric test.

Example 6.11.3—C1 Individual Bacterial Strains Reduce Colon Tissue IL-17A and IL-12p40 in DSS-Induced Colitis Model DSS-induced colitis is characterized by intestinal inflammation associated with an increase in tissue proinflammatory cytokines which include IL-12p40 and IL-17A. In addition to disease scores, the levels of inflammatory cytokines were also evaluated in colonic tissue at the study termination on Day 21 (FIG. 12). Evaluation of colonic tissue levels of these cytokines in the groups administered the three individual C1 bacterial strains, EHA01, RHO01, and BTH01 as well as the anti-IL-12p40 positive control demonstrated a reduction in IL-12p40 (FIG. 12A) and IL-17A (FIG. 12B) relative to vehicle control. Each of the three individual C1 strains significantly protected from the DSS-induced increase in IL-17A and strains EHA01 and BTH01 also significantly lowered colonic tissue IL-12p40, with RHO01 showing a trend.

Example 6.12—Bacterial Consortium Reduces Disease Severity in DSS-Induced Colitis Model Mice were treated with drinking water containing 3% DSS for five days to induce gut mucosal damage followed by DSS removal for the remainder of the 19-day study. The C1 consortium, including $1\times10^9$ VCC of each of the individual C1 strains in re-hydrated lyophilized form, was administered by oral gavage daily for the entire study duration. Individual bacterial strains, EHA01, RHO01 and BTH01, in lyophilized form were also tested at a daily dose of $3\times10^9$ VCC for the entire duration of the study. The C1 consortium, including $1\times10^9$ VCC of each of the individual C1 strains in re-hydrated lyophilized form, was also administered in combination with anti-IL-12p40 antibody (at 10 mg/kg in PBS, dosed Q3D starting on Day 6 by IP) (FIG. 13). An antibody against IL-12p40 was administered parenterally as a positive control for efficacy. The primary efficacy endpoint in this study was body weight loss over time.

The full compilation of daily weight loss percentage and statistics is depicted in Table 10, which shows mean weight loss percent±SEM by day of individual test articles (N=12), consortium (N=24), vehicle negative control (N=20) and Anti-IL-12p40 positive control (N=12). Q value≤0.05 is considered statistically significant using the Kruskal-Wallis test to concurrently compare all test articles included in table to the vehicle control with Two-stage step-up method of Bejamini, Keieger and Yekutieli to correct for multiple comparison by controlling False Discovery Rate. Results were similar when analyzed using the one-way ANOVA test.

TABLE 10

Mean Weight Loss Percent and Statistical Analysis from DSS-induced Colitis Study

| | Vehicle | EHA01 | | RHO01 | | BTH01 | | Consortium | | Anti-IL-12p40 | |
|---|---|---|---|---|---|---|---|---|---|---|---|
| Days | Mean | Mean | Q value | Mean | Q value | Mean | Q value | Mean | Q value | Mean | Q value |
| 0 | 0 ± 0.0 | 0 ± 0.0 | NA | 0 ± 0.0 | NA | 0 ± 0.0 | NA | 0 ± 0.0 | NA | 0 ± 0.0 | NA |
| 1 | −1 ± .33 | −1 ± .44 | 0.4226 | −0.5 ± .64 | 0.2842 | 0.5 ± .48 | 0.0067 | −1 ± .42 | 0.4226 | 1 ± .47 | 0.0024 |
| 2 | −0.8 ± .29 | −1.0 ± .32 | 0.3207 | 0.6 ± .70 | 0.036 | 1.2 ± .43 | 0.0019 | 0.5 ± .55 | 0.0093 | 1.4 ± .52 | 0.0018 |
| 3 | −1.9 ± .41 | −0.7 ± .40 | 0.062 | 1.3 ± .85 | 0.0008 | 0.6 ± .64 | 0.0025 | 0.1 ± .55 | 0.0011 | 2.1 ± .56 | <0.0001 |
| 4 | −0.0 ± .40 | −0.2 ± .44 | −0.952 | 2 ± 1.1 | 0.1866 | 2 ± .90 | 0.1704 | 0.0 ± .65 | 0.952 | 0.6 ± .62 | 0.5897 |
| 5 | −3 ± .58 | −2 ± .59 | 0.8271 | 0.08 ± 1.1 | 0.1838 | −3 ± .84 | 0.8271 | −2 ± .78 | 0.8271 | −3 ± .86 | 0.8289 |
| 6 | −9 ± .51 | −9 ± .93 | 0.9826 | −8 ± 1.7 | 0.9826 | −9 ± 1.3 | 0.9826 | −8 ± .71 | 0.9826 | −9 ± 1.2 | >0.9999 |

TABLE 10-continued

Mean Weight Loss Percent and Statistical Analysis from DSS-induced Colitis Study

| | Vehicle | EHA01 | | RHO01 | | BTH01 | | Consortium | | Anti-IL-12p40 | |
|---|---|---|---|---|---|---|---|---|---|---|---|
| Days | Mean | Mean | Q value | Mean | Q value | Mean | Q value | Mean | Q value | Mean | Q value |
| 7  | −15 ± .71 | −15 ± 1.1 | >0.9999 | −13 ± 1.6 | 0.4719 | −15 ± .84 | >0.9999 | −14 ± .58 | 0.4719 | −13 ± 1.4 | 0.5332 |
| 8  | −18 ± .54 | −18 ± .96 | >0.9999 | −16 ± 1.5 | 0.1029 | −17 ± 1.1 | 0.4343 | −17 ± .58 | 0.2334 | −16 ± 1.7 | 0.1029 |
| 9  | −19 ± .66 | −18 ± 1.2 | 0.4645 | −13 ± 2.0 | 0.0141 | −17 ± 1.5 | 0.3571 | −17 ± .87 | 0.0849 | −14 ± 2.2 | 0.0366 |
| 10 | −20 ± .75 | −18 ± 1.2 | 0.0403 | −13 ± 1.8 | 0.001  | −18 ± 1.7 | 0.0403 | −17 ± .93 | 0.0058 | −15 ± 2.2 | 0.0058 |
| 11 | −20 ± .91 | −17 ± 1.7 | 0.2112 | −11 ± 2.1 | 0.0024 | −19 ± 2.0 | 0.3578 | −16 ± 1.1 | 0.0557 | −15 ± 2.6 | 0.0557 |
| 12 | −20 ± 1.0 | −16 ± 1.8 | 0.0787 | −11 ± 2.4 | 0.0028 | −18 ± 1.9 | 0.1642 | −14 ± 1.2 | 0.0049 | −15 ± 2.7 | 0.0358 |
| 13 | −19 ± 1.2 | −15 ± 1.9 | 0.0706 | −9 ± 2.1  | 0.0015 | −17 ± 2.1 | 0.1065 | −13 ± 1.2 | 0.0036 | −12 ± 2.4 | 0.0043 |
| 14 | −16 ± 1.1 | −12 ± 1.7 | 0.0298 | −9.6 ± 2.6 | 0.0053 | −14 ± 2.1 | 0.092 | −11 ± 1.1 | 0.0032 | −10 ± 2.8 | 0.0032 |
| 15 | −13 ± 1.2 | −12 ± 2.1 | 0.033  | −7 ± 2.3  | 0.0088 | −13 ± 2.1 | 0.1722 | −8 ± 1.0  | 0.0044 | −7 ± 2.9  | 0.0034 |
| 16 | −10 ± 1.2 | −6 ± 1.6  | 0.0214 | −4 ± 2.5  | 0.0095 | −9 ± 2.2  | 0.1606 | −4 ± 1.0  | 0.0019 | −4 ± 2.7  | 0.0019 |
| 17 | −11 ± 1.1 | −6 ± 1.4  | 0.0061 | −3 ± 2.1  | 0.0005 | −9 ± .2   | 0.0476 | −4 ± 1.0  | 0.0001 | −5 ± 2.4  | 0.0014 |
| 18 | −9 ± 1.2  | −6 ± 1.6  | 0.0815 | −2 ± 1.8  | 0.0043 | −8 ± 1.6  | 0.3138 | −4 ± 1.3  | 0.0077 | −3 ± 2.1  | 0.0077 |
| 19 | −7 ± 1.0  | −4 ± 1.1  | 0.0555 | −.4 ± 1.6 | 0.0027 | −5 ± 1.5  | 0.1079 | −3 ± 1.0  | 0.008  | −2 ± 1.7  | 0.0052 |

Example 6.12.1—C1 Bacterial Consortium Protects Against Weight Loss in DSS-Induced Colitis Model The C1 consortium demonstrated protection against DSS-induced weight loss, similar to that seen with the anti-IL-12p40 antibody, compared to the vehicle control (FIG. 13D). The protection observed with the C1 consortium and anti-IL-12p40 was statistically significant from the peak of gut damage on day 10 until the termination of the study on day 19. The individual strains, EHA01, RHO01 and BTH01, also demonstrated protection against weight loss compared to vehicle control (FIG. 13A-C). The individual strain protection reached statistical significance on days 10 and 17 with all treatment groups except for BTH01 reaching statistically significant weight loss protection on days 14-17. Administration of the C1 consortium in combination with anti-IL-12p40 demonstrated protection against DSS-induced weight loss compared to the vehicle control, C1 consortium alone, and anti-IL-12p40 alone (FIG. 13E), as reflected in the AUC which sums the weight percent change from Day 0 of the study (FIG. 13F).

Example 6.12.2—C1 Bacterial Consortium Reduces Colon Tissue IL-17A, TNF-α and IL-6 in DSS-Induced Colitis Model Evaluation of cytokines in colon tissue from mice administered the C1 consortium demonstrated a reduction in the proinflammatory cytokines IL-17A, TNF-α and IL-6 relative to vehicle control (FIG. 14). The anti-IL-12p40 positive control also demonstrated protection against DSS-induced increase in these proinflammatory cytokines which was statistically significant for IL-17A.

Example 6.12.3—C1 Bacterial Consortium Reduces Plasma Lipocalin-2/NGAL Levels in DSS-Induced Colitis Model Evaluation of Lipocalin-2, a disease activity biomarker in inflammatory bowel disease (Stallhofer et al., *Inflamm Bowel Dis* 21 (10): 2327-2340 (2015)), was performed on plasma from mice administered the individual strains, EHA01, RHO01 and BTH01, the C1 consortium, anti-IL-12p40 alone and anti-IL-12p40 in combination with the C1 consortium (FIG. 15). Administration of each of the individual strains, EHA01, RHO01 and BTH01, the C1 consortium alone, and the C1 consortium combined with anti-IL-12p40 resulted in a reduction in plasma levels of Lipocalin-2 compared to vehicle control, with the C1 consortium combined with anti-IL-12p40 showing a reduction greater than that observed for either the C1 consortium alone or anti-IL-12p40 alone (FIG. 15A). Differences between groups of experiments were statistically determined by using one-factor ANOVA with a Tukey post hoc test. FIG. 15B shows that the reduction in Lipocalin-2 plasma levels correlated with the % change in body weight, with greater reductions in Lipocalin-2 corresponding to reduced body weight loss in the DSS model. (r=−0.5129; 95% confidence interval=− 0.6502 to −0.3432; $R^2$=0.2631; P value: P (two-tailed)=<0.0001; significant (alpha=0.05)).

Example 7—Clinical Study

A first-in-human study is conducted to investigate the safety/tolerability, pharmacokinetics and pharmacodynamics of the investigational drug C1. C1 includes commensal gut bacterial strains derived (purified and mono-cultured) from the stool of healthy human donors. Bacterial strains were selected for their potential to modulate mucosal inflammation and barrier function, which are dysregulated in patients with UC, as described in the foregoing Examples herein.

The study is an adaptive design, two-cohort, dose-ascending study to evaluate the safety and efficacy of 1 to 5 C1 capsules orally administered once daily for 8 weeks. C1 is administered as a monotherapy or in combination with oral mesalamine (standard-of-care) to subjects with mildly-to-moderately active UC with evidence of an inadequate response to ongoing mesalamine treatment. An inadequate response to mesalamine is defined as the presence of signs and/or symptoms of active UC despite receiving treatment with ≥2.4 g/day of oral mesalamine with or without concomitant topical (rectal) mesalamine (mesalamine suppository 1000 mg PR QHS or mesalamine enema 4 g PR QHS) for >4 weeks from screening visit.

The study will enroll 44 subjects across two sequential, non-overlapping dose cohorts (Cohort A and Cohort B). The first cohort (Cohort A) will randomize 20 subjects, allocated 1:1 to treatment with one capsule per day of C1 or Placebo. The second cohort (Cohort B) will randomize 24 subjects, allocated 3:1 to once-a-day treatment with up to 5 capsules per day of C1 or Placebo.

Inclusion criteria include the following. 1) Men or women, 18 to 70 years of age. 2) Established diagnosis of UC for at least 3 months prior to screening, based on clinical history, exclusion of infectious causes, and characteristic endoscopic and histologic findings. 3) Active UC with disease involving the colon and rectum, with at least 15 cm of involved colon; subjects with isolated ulcerative proctitis (disease that does not extend beyond 15 cm of the anal verge) will be excluded. 4) Modified Mayo Score 3-8, with score of ≤2 points in each individual category of the modified Mayo scoring system and endoscopy score activity of ≥1 point at the most affected area, based on a sigmoidoscopy or full colonoscopy (if colonoscopy not done within the past 24 months), at ≤2 weeks from subject randomization. Only the sigmoid should be scored up to approximately 30-40 cm, although the extent of disease beyond this level will be documented for subjects receiving full colonoscopy or sigmoidoscopy. 5) Subjects with active disease (defined per clinical and endoscopy criteria) despite ongoing treatment with oral mesalamine ≥2.4 g/day with or without concomitant topical (rectal) mesalamine (mesalamine suppository 1000 mg PR QHS or mesalamine enema 4 g PR QHS) for ≥4 weeks from screening visit. 6) Treatment with stable dosage of oral mesalamine and concomitant topical (rectal) mesalamine (if applicable) during study screening and treatment phases. 7) Treatment with a stable oral corticosteroid dose of ≤15 mg prednisone/day or equivalent during study screening and treatment phase.

Study drug will be unit dose packaged inside a plastic tube with screw cap. The capsule-containing tube and a 1-g silica-gel desiccant sachet will be placed inside a heat-scaled aluminum foil pouch.

Seven (7) unit dose foil pouches of study drug will be placed into an outer carton to form a weekly pack. Eight (8) Weekly packs of study drug will be provided to each patient in two separate kits. The first kit [1 of 2] contains five (5) weekly packs of study drug in an outer carton. The second kit [2 of 2] contains three (3) weekly packs of study drug in an outer carton.

Study drug must be stored refrigerated (2-8° C.) in a secure location at the study site. Study drug storage conditions (e.g., temperature and other requirements) will be identified on the study drug label and in the investigator site file. Study drug must not be frozen.

Each non-placebo capsule is targeted to contain $1 \times 10^9$ viable organisms per bacterial strain. Subjects in Cohort A will be administered 1 capsule per day for 8 weeks. Subjects in Cohort B with be administered up to 5 capsules per day for 8 weeks. Subjects will be instructed to swallow intact study drug capsules at one time every day, in the morning after overnight fast, with a full glass of water. They will wait for at least 60 minutes after ingesting study drug before consuming the first solid or liquid meal of the day (excluding water).

Safety is assessed based on the incidence of treatment emergent adverse events graded for severity, including serious adverse events.

A primary efficacy assessment is the percentage of subjects in clinical remission at end of the 8-week treatment duration using the modified Mayo score (MMS).

The Mayo scoring system for assessment of ulcerative colitis activity is described in Rutgeerts et al., *N Engl J Med.* 353 (23): 2462-76 (2005). The Mayo scoring system includes stool frequency, rectal bleeding. findings on endoscopy, and physician's global assessment. Stool frequency has a subscore of 0 to 3, with 0=normal number of stools for this patient, 1=1-2 stools more than normal, 2=3-4 stools more than normal, and 3=5 or more stools more than normal. Each patient serves as his or her own control to establish the degree of abnormality of the stool frequency. Rectal bleeding has a subscore of 0 to 3, with 0=no blood seen, 1=streaks of blood with stool less than half the time, 2=obvious blood with stool most of the time, and 3=blood alone passes. The daily bleeding score represents the most severe bleeding of the day. Findings on endoscopy has a subscore of 0 to 3, with 0=normal or inactive disease, 1=mild disease (erythema, decreased vascular pattern), 2=moderate disease (marked erythema, lack of vascular pattern, friability, erosions), and 3=severe disease (spontaneous bleeding, ulceration). Physician's global assessment has a subscore of 0 to 3, with 0=normal, 1=mild disease, 2=moderate disease, 3=severe disease. The physician's global assessment acknowledges the three other criteria, the patient's daily recollection of abdominal discomfort and general sense of well-being, and other observations, such as physical findings and the patient's performance status.

The Modified Mayo Score (MMS) excludes the PGA component of the Mayo Score. The modified Mayo score ranges from 0 to 9, with higher scores indicating more severe disease. Clinical remission will be measured using the modified Mayo score (MMS), based on attaining a sub-score of '0' points for rectal bleeding and sub-scores of 0 or 1 points for endoscopic mucosal appearance and stool frequency, with at least a 1-point decrease from baseline in stool frequency.

A primary efficacy assessment is endoscopic improvement at end of the 8-week treatment duration using the Ulcerative Colitis Endoscopic Index of Severity (UCEIS). Improvement in endoscopic disease severity will be assessed using change from baseline in UCEIS score. The UCEIS includes 3 descriptors of endoscopic severity, each with specific definitions and scored on a simple visual analog scale with a score of 0 representing normality. The descriptors are vascular pattern (3 levels), bleeding (4 levels), and erosions and ulcers (4 levels). The final score, calculated from a simple sum of individual scores, ranges from 0 to 8, with higher scores indicating more severe disease.

The study also collects patient reported outcome data relevant to underlying disease state using UC PRO2. In addition to the above-mentioned clinical assessments, the study includes acquisition of longitudinal stool samples, and baseline and end-of-study mucosal biopsy samples to understand and potentially correlate changes in gut microbiota composition (taxonomy and phenotype) with clinical outcomes.

Concomitant treatments/medications, those administered between the date of study randomization and the end-of-study treatment visit, are administered only as medically necessary. Examples of such medications include rescue medications for exacerbation of UC disease activity, systemic antibiotics for treatment of intercurrent infections, or gastric acid reducers such as H2 blockers or proton pump inhibitors. These include: increase in dose of oral corticosteroids; introduction of oral corticosteroids; introduction of topical corticosteroids; increase in dose of oral mesalamine; introduction of topical mesalamine; and introduction of other oral 5-ASA formulations and prodrugs, including sulfasalazine, olsalazine or balsalazide. Rescue medications include parenteral corticosteroids, 6-MP, azathioprine, low dose methotrexate, intravenous immunoglobulins (IVIG), anti-TNF agents, natalizumab, vedolizumab, cyclosporin, tacrolimus, tofacitinib, other commercially available biologic agents, or experimental medications.

Example 8—Manufacture of Bacterial Strain Compositions: Fermentation, Harvest and Lyophilization A flow chart of an exemplary GMP process is provided in FIG. 15. One or more vials of each bacterial strain MCB is used to prepare an inoculum. The resulting culture is used to inoculate a fermenter. After fermentation, the cells are harvested by tangential flow filtration (TFF) and/or centrifugation, blended with selected cryopreservatives as detailed in Table 11 and then dispensed into trays, frozen (−70±10° C.), and subsequently lyophilized.

TABLE 11

Cryopreservatives Used for Each C1 Component

| Bacterial Strain Composition | Components of Cryopreservative Blend |
|---|---|
| BTH01 | Sucrose |
| EHA01 | Raftilose ®, Maltodextrin, Alginate, Trehalose, Sucrose |
| RHO01 | Raftilose ®, Maltodextrin, Alginate, Trehalose |

Example 9—Capsule-In-Capsule

Figure 16:
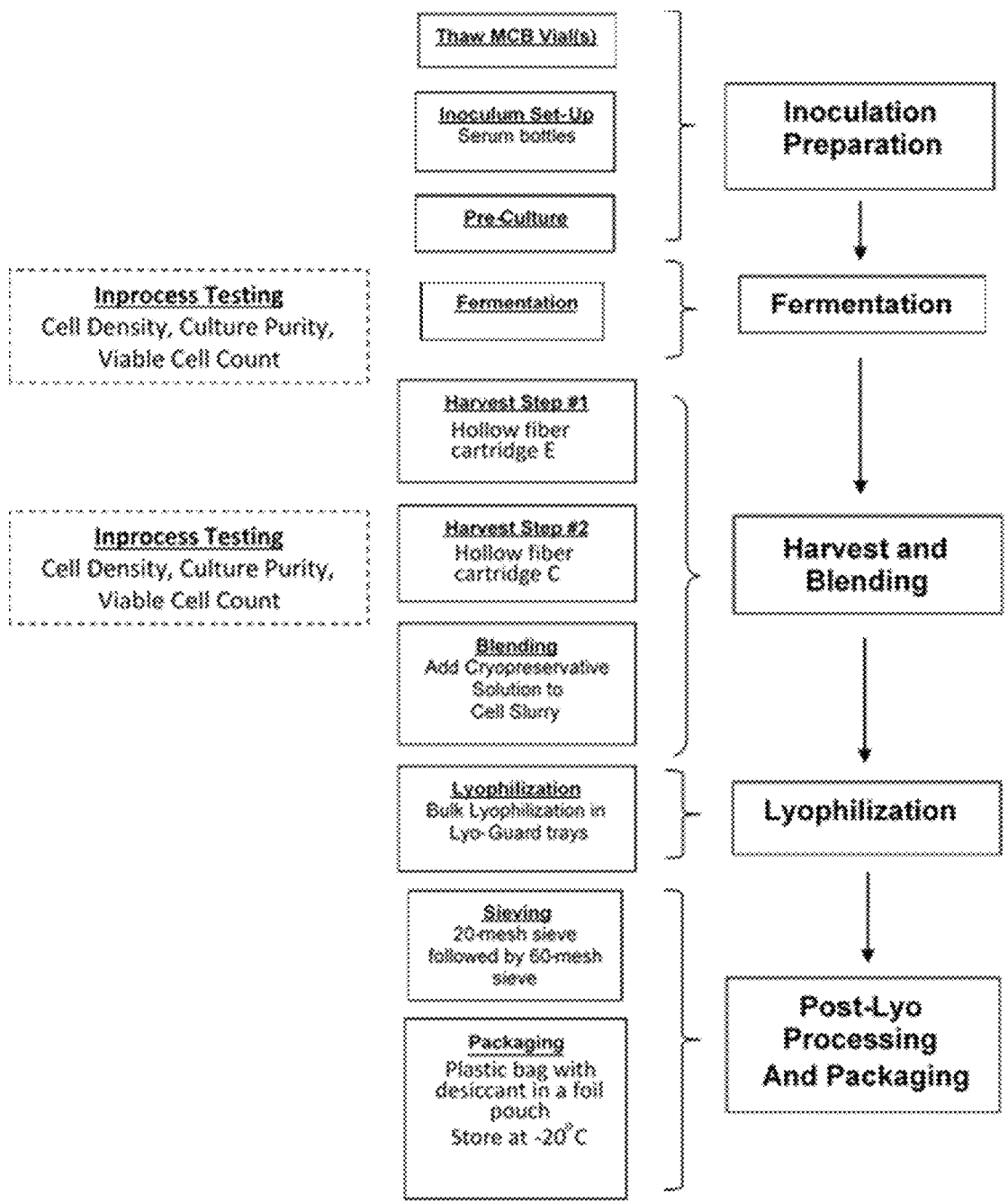
FIG. 16 depicts a process flow diagram for the manufacture of a lyophilized powder form of a bacterial strain.

In this example, C1 is formulated for oral administration as a capsule-in-capsule dosage form (e.g., Gemicel®). FIG. 16 shows a schematic representation of a Gemicel® design. In this example, both the inner and the outer capsules are filled with the same C1 formulation, and both the inner and the outer capsules are banded prior to coating. The drug release characteristics are provided by functional coatings, as follows:

(a) An outer enteric-coated capsule, which provides gastric resistance in the stomach and proximal small intestine, then releases its contents of the powder fill formulation and the coated inner capsule into the distal ileum. The enteric polymer is designed to dissolve as intestinal pH increases to a critical pH for dissolution of the enteric polymer; and (b) An inner reverse enteric-coated capsule, which is intended to release its contents of powder fill formulation in the proximal colon. The reverse enteric polymer is designed to dissolve as intestinal pH decreases to a critical pH for dissolution of the reverse enteric polymer. The reverse enteric polymer exploits the pH drop in the ileocecal region of the intestine.

A human scintigraphy study was previously performed, which demonstrated that release was achieved at the expected anatomic targets.

Figure 17:
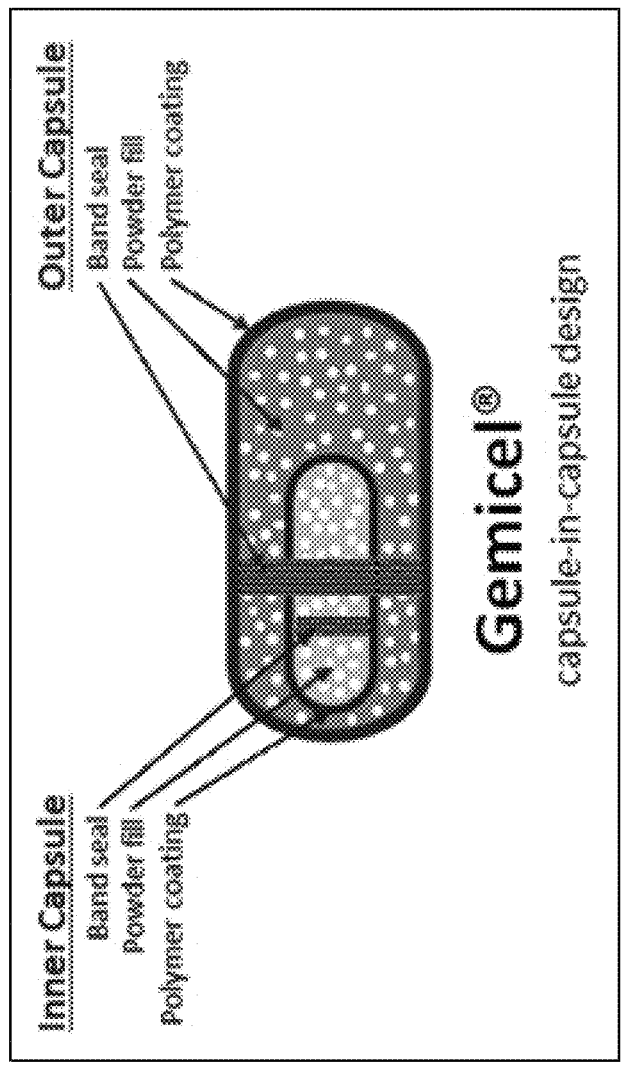
FIG. 17 depicts a schematic representation of the Gemicel® capsule-in-capsule.
Figure 18:
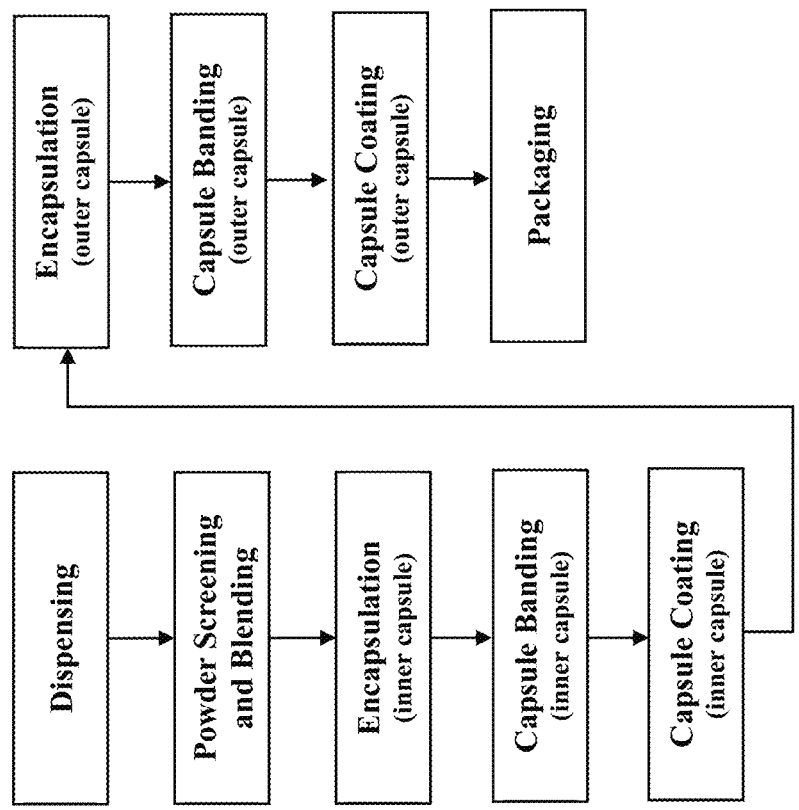
FIG. 18 depicts a manufacturing flow chart for a capsule-in-capsule.

For the example depicted in FIG. 17, the powder fill formulation includes three individually lyophilized bacterial compositions. The formulated concentration of each bacterial strain is targeted to be between about $3 \times 10^8$ and about $3 \times 10^{10}$ viable organisms in each C1 Gemicel® capsule-in-capsule dose (i.e., total of both the inner and the outer capsules in a single C1 Gemicel®). The powder fill formulation also contains other typical pharmaceutical excipients (e.g., filler, disintegrant, glidant, and lubricant).

Unit dose packaging includes a single Gemicel® capsule inside a heat-sealed foil pouch containing a desiccant pouch. As an added precaution during early studies, the capsule is inserted into a protective plastic sleeve prior to placing in the foil pouch.

Example 10—Composition

The components used for C1 in an exemplary capsule-in-capsule formulation are shown in Table 12. In this example, the powder fill formulation includes three individually lyophilized bacterial strain compositions. The powder fill formulation also contains other typical pharmaceutical excipients (e.g., filler, disintegrant, glidant, and lubricant). The inner and outer capsules are composed of hydroxypropyl methylcellulose (HPMC) with the inner capsule being a smaller size than the outer capsule. The banding polymer is also composed of HPMC, which is used to seal each capsule and provides a suitable surface across the seam prior to coating. The coating polymers determine the functional performance of the capsule-in-capsule. The outer capsule is coated with a prescribed blend of enteric polymers (poly(methacrylic acid-co-methyl methacrylate) 1:1 and poly(methacrylic acid-co-methyl methacrylate) 1:2), which provide gastric resistance in the stomach and proximal small intestine, then releases its contents of powder fill formulation and the coated inner capsule into the distal ileum. The inner capsule is coated with a reverse enteric polymer (amino methacrylate copolymer (2:1:1)), which releases its contents of powder fill formulation into the proximal colon.

TABLE 12

Components of an Exemplary C1 Capsule-in-Capsule Formulation

| | Function |
|---|---|
| Powder Fill Components | |
| Lyophilized Bacterial Strains[1] | Actives |
| Microcrystalline Cellulose | Filler |
| Crospovidone (polyvinyl pyrrolidone) | Disintegrant |
| Silicon Dioxide | Flow aid, glidant |
| Sodium Stearyl Fumarate | Lubricant |
| Capsule Shell | |
| Hydroxypropyl methylcellulose (HPMC) Capsules | Capsule shell |
| Banding Polymer | |
| Hydroxypropyl methylcellulose (HPMC) | Banding polymer |
| Purified water[2] | Banding solvent |
| Ethanol[2] | Banding solvent |
| Inner Capsule Coating Polymer | |
| Amino Methacrylate Copolymer (2:1:1) | Reverse enteric coating polymer |
| Sodium Lauryl Sulfate | Surfactant |
| Silicon Dioxide | Flow aid, glidant |
| Stearic Acid | Lubricant |
| Talc | Anti-tacking agent |
| Purified water[2] | Coating solvent |
| Outer Capsule Coating Polymer | |
| Poly (methacrylic acid-co-methyl methacrylate) 1:1 | Enteric coating polymer |
| Poly (methacrylic acid-co-methyl methacrylate) 1:2 | Enteric coating polymer |
| Triethyl Citrate | Plasticizer |
| Talc | Anti-tacking agent |
| Ammonia Solution (1N)[2] | pH adjuster |
| Purified Water[2] | Coating solvent |
| Isopropyl alcohol[2] | Coating solvent |

[1]C1 bacterial strains, BTH01, EHA01 and RHO01, including cryoprotectants, will be used in the powder fill formulation of C1 Gemicel ® capsules.
[2]These solvents are removed during processing.

Example 11—Manufacture of an Exemplary C1 Capsule-In-Capsule Formulation

A manufacturing flow chart for example C1 Gemicel® capsules is shown in FIG. 16. Exemplary steps include the following:

Dispensing

Lyophilized bacterial strain compositions are removed from frozen storage and allowed to equilibrate to room temperature prior to dispensing. Active and inactive materials are accurately weighed.

Powder Screening and Blending

Powders may be screened to remove lumps, then blended in a conventional bin-type blender (e.g., V-blender). Glidant and lubricant excipients may be separately pre-blended with an appropriate quantity of filler prior to adding into the blender.

Encapsulation (Inner Capsule)

The inner HPMC capsules are separated manually or using semi-automatic equipment. The prescribed amount of powder blend is accurately filled manually or using semi-automatic equipment into the body of each capsule, then each capsule is closed.

Capsule Banding (Inner Capsule)

The inner capsules are band sealed using a hydroalcoholic HPMC solution followed by drying. Banding is performed circumferentially at the capsule seam using semi-automatic or automatic equipment.

Capsule Coating (Inner Capsule)

The inner capsule is coated with a reverse enteric polymer (amino methacrylate copolymer) solution using conventional pan coating equipment. Capsules are coated until the target weight gain is achieved.

Encapsulation (Outer Capsule)

The outer HPMC capsules are separated manually or using semi-automatic equipment. A banded/coated inner capsule is placed into the body of each capsule. The prescribed amount of powder blend is then accurately filled manually or using semi-automatic equipment into the same body of each capsule, then each capsule is closed.

Capsule Banding (Outer Capsule)

The outer capsules are band sealed using a hydroalcoholic HPMC solution followed by drying. Banding is performed circumferentially at the capsule seam using semi-automatic or automatic equipment.

Capsule Coating (Outer Capsule)

The outer capsule is coated with an enteric polymer (poly(methacrylic acid-co-methyl methacrylate) solution using conventional pan coating equipment. Capsules are coated until the target weight gain is achieved.

Packaging

Each capsule-in-capsule unit dose is packaged inside a heat-sealed foil pouch containing a silica gel desiccant pouch. In addition, the capsule may be inserted into a protective plastic sleeve prior to placing in the foil pouch. Packaged capsule-in-capsule is stored at 5° C.

INCORPORATION BY REFERENCE

The entire disclosure of each of the patent and scientific documents referred to herein is incorporated by reference for all purposes.

EQUIVALENTS

The disclosure may be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

SEQUENCE LISTING

The patent contains a lengthy sequence listing. A copy of the sequence listing is available in electronic form from the USPTO web site (https://seqdata.uspto.gov/?pageRequest=docDetail&DocID=US12144834B2). An electronic copy of the sequence listing will also be available from the USPTO upon request and payment of the fee set forth in 37 CFR 1.19(b)(3).

What is claimed is:

1. A pharmaceutical composition comprising an effective amount of a bacterial mixture, the mixture comprising an isolated *Bacteroides thetaiotaomicron* strain, an isolated *Eubacterium hallii* strain, and an isolated *Roseburia hominis* strain, and a pharmaceutically acceptable excipient, wherein the bacterial mixture is capable of one or more of
    (a) increasing production of IL-10;
    (b) increasing production of CCL-18;
    (c) increasing gut barrier integrity;
    (d) increasing autophagy; and
    (e) reducing or attenuating production of plasma Lipocalin-2/NGAL; and
wherein the *Bacteroides thetaiotaomicron* strain is the live BTH01 (P118-A12a) strain comprising the 16s rRNA sequence of SEQ ID NO: 2; the *Eubacterium hallii* strain is the live EHA01 (P168-F1a) strain comprising the 16s rRNA sequence of SEQ ID NO: 3; and the *Roseburia hominis* strain is the live RHO01 (P127-H9a) strain comprising the 16s rRNA sequence of SEQ ID NO: 1, wherein the BTH01 strain is deposited at the DSMZ with the accession number DSM-32919, the EHA01 strain is deposited at the DSMZ with the accession number DSM 32920, and the RHO01 strain is deposited at the DSMZ with the accession number of DSM 32921.

2. The pharmaceutical composition of claim 1, wherein the bacterial mixture is capable of increasing production of IL-10 and/or CCL-18 in a human THP-1 macrophage and/or peripheral blood mononuclear cell.

3. The pharmaceutical composition of claim 1, wherein the bacterial mixture is capable of increasing gut barrier integrity of HT29MTX-E12 cell monolayer.

4. The pharmaceutical composition of claim 1, wherein the bacterial mixture is capable of increasing gut barrier integrity of a HT29MTX-E12 cell monolayer treated with TNF-alpha.

5. The pharmaceutical composition of claim 1, wherein the bacterial mixture is capable of increasing autophagy in a human THP-1 macrophage.

6. The pharmaceutical composition of claim 1, wherein the bacterial mixture is capable of reducing or attenuating the production of Lipocalin-2/NGAL in a cell or a tissue.

7. The pharmaceutical composition of claim 1, wherein the bacterial strains of the bacterial mixture are capable of acting synergistically compared to each of the bacterial strains acting individually.

8. The pharmaceutical composition of claim 1, wherein each of the bacterial strains of the bacterial mixture is in lyophilized form and wherein the pharmaceutical composition has at least $1 \times 10^8$ viable colony forming units of each of the bacterial strains.

9. The pharmaceutical composition of claim 1, wherein the bacterial mixture comprises at least about $1 \times 10^9$ viable colony forming units of the *Bacteroides thetaiotaomicron* strain, at least about $1 \times 10^9$ viable colony forming units of the *Eubacterium hallii* strain, and at least about $1 \times 10^9$ viable colony forming units of the *Roseburia hominis* strain.

10. The pharmaceutical composition of claim 1, wherein the bacterial mixture further comprises a cryoprotectant selected from the group consisting of a fructooligosaccharide, trehalose, and a mixture thereof.

11. The pharmaceutical composition of claim 1, wherein the composition is comprised in a capsule.

12. The pharmaceutical composition of claim 11, wherein the capsule is a dual component capsule.

13. The pharmaceutical composition of claim 12, wherein the dual component capsule is a capsule-in-capsule.

14. The pharmaceutical composition of claim 12, wherein the capsule-in-capsule comprises:
an inner capsule comprising the bacterial mixture in a lyophilized form, wherein the inner capsule further comprises a reverse enteric polymeric coating; and
an outer capsule encapsulating the inner capsule, the outer capsule comprising the bacterial mixture in a lyophilized form, wherein the outer capsule further comprises an enteric polymeric coating.

15. The pharmaceutical composition of claim 1, wherein upon storage for 6 months at 4° C., the pharmaceutical composition loses at most 3 log colony forming units of each of the bacterial strains.

16. The pharmaceutical composition of claim 15, wherein upon storage for 12 months at 4° C., the pharmaceutical composition loses at most 3 log colony forming units of each of the bacterial strains.

17. The pharmaceutical composition of claim 16, wherein upon storage for 24 months at 4° C., the pharmaceutical composition loses at most 3 log colony forming units of each of the bacterial strains.

18. A method of treating an immune mediated inflammatory gastrointestinal disorder in a mammalian subject in need thereof, the method comprising orally administering to the subject an effective amount of the pharmaceutical composition of claim 1.

19. The method of claim 18, wherein the inflammatory gastrointestinal disorder is ulcerative colitis or Crohn's disease.

20. The method of claim 19, wherein the inflammatory gastrointestinal disorder is ulcerative colitis.

21. The method of claim 20, wherein the subject has had an inadequate response to prior oral administration of ≥2.4 g/day of mesalamine for at least 8 weeks.

22. The method of claim 18, wherein the mammalian subject is selected from a human, a companion animal, or a livestock animal.

23. The method of claim 22, wherein the mammalian subject is a human.

24. A method of treating dysbiosis in a mammalian subject in need thereof, the method comprising orally administering to the subject an effective amount of the pharmaceutical composition of claim 1.

* * * * *